United States Patent
Tahari et al.

(10) Patent No.: US 9,981,976 B2
(45) Date of Patent: May 29, 2018

(54) PIPERIDINE SUBSTITUTED PYRAZOLO[1,5-A]PYRIMIDINE DERIVATIVES WITH INHIBITORY ACTIVITY ON THE REPLICATION OF THE RESPIRATORY SYNCYTIAL VIRUS (RSV)

(71) Applicant: JANSSEN SCIENCES IRELAND UC, Little Island,

PIPERIDINE SUBSTITUTED PYRAZOLO[1,5-A]PYRIMIDINE DERIVATIVES WITH INHIBITORY ACTIVITY ON THE REPLICATION OF THE RESPIRATORY SYNCYTIAL VIRUS (RSV)

CROSS-REFERENCE TO RELATED APPLICATIONS

This application is a national phase entry of International Application No. PCT/EP2015/078762, filed on Dec. 7, 2015, which claims priority to EP Patent Application No. 14196782.8, filed on Dec. 8, 2014, each of which is incorporated herein in its entirety.

FIELD OF THE INVENTION

The invention concerns novel substituted bicyclic pyrazolo pyrimidine compounds having antiviral activity, in particular, having an inhibitory activity on the replication of the respiratory syncytial virus (RSV). The invention further concerns the preparation of such novel compounds, compositions comprising these compounds, and the compounds for use in the treatment of respiratory syncytial virus infection.

BACKGROUND

Human RSV or Respiratory Syncytial Virus is a large RNA virus, member of the family of Paramyxoviridae, subfamily pneumoviridae together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. A first one is ribavirin, a nucleoside analogue that provides an aerosol treatment for serious RSV infection in hospitalized children. The aerosol route of administration, the toxicity (risk of teratogenicity), the cost and the highly variable efficacy limit its use. The other two drugs, RespiGam® (RSV-IG) and Synagis® (palivizumab), polyclonal and monoclonal antibody immunostimulants, are intended to be used in a preventive way. Both are very expensive, and require parenteral administration.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication. It would be particularly preferred to provide drugs against RSV replication that could be administered perorally.

Compounds that exhibit anti-RSV activity are disclosed in WO-2011/163518, WO-2013/096681 and WO-2013/158776.

SUMMARY OF THE INVENTION

The present invention relates to a compound of formula (I), including any stereochemically isomeric form thereof, wherein

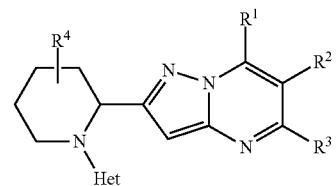

(I)

$R^1$ is hydrogen, hydroxy, $C_{1-4}$alkyl, mono- or di($C_{1-4}$alkyl)amino, or Heterocyclyl$^1$;

$R^2$ is hydrogen or $C_{1-4}$alkyl;

$R^3$ is $C_{1-4}$alkyl, halo, $C_{3-6}$cycloalkyl, mono- or di($C_{1-4}$alkyl)amino, or Heterocyclyl$^2$;

$R^4$ is hydrogen, $C_{1-6}$alkyl, hydroxy, or halo;

Heterocyclyl$^1$ is azetidinyl, pyrrolidinyl, piperidinyl, piperazinyl, or morpholinyl; wherein each Heterocyclyl$^1$ is optionally substituted with one or two substituents selected from $C_{1-4}$alkyl, hydroxy, halo, polyhalo $C_{1-4}$alkyl, $C_{1-4}$alkyloxycarbonyl, amino, $C_{1-4}$alkylaminocarbonyl, or $C_{1-4}$alkylsulfonyl;

Heterocyclyl$^2$ is azetidinyl, pyrrolidinyl, piperidinyl, piperazinyl, or morpholinyl; wherein each Heterocyclyl$^2$ is optionally substituted with one or two substituents selected from $C_{1-4}$alkyl, hydroxy, halo, polyhalo $C_{1-4}$alkyl, $C_{1-4}$alkyloxycarbonyl, amino, $C_{1-4}$alkyloxycarbonylamino, or $C_{1-4}$alkylsulfonyl;

Het is selected from furanyl, thiophenyl, pyrazolyl, oxazolyl, thiazolyl, pyridyl, pyridazinyl, pyrimidinyl, pyrazinyl, quinolyl, isoquinolyl, cinnolinyl, quinazolinyl, quinoxalinyl, 1,5-naphthyridinyl, 1,6-naphthyridinyl, 1,7-naphthyridinyl, 1,8-naphthyridinyl, pyrido[2,3-d]pyrimidinyl, pyrido[3,2-d]pyrimidinyl, 9H-purinyl, thiazolo[5,4-d]pyrimidinyl, 7H-pyrrolo[2,3-d]pyrimidinyl, oxazolo[5,4-d]pyrimidinyl, thieno[2,3-d]pyrimidinyl, or thieno[3,2-d]pyrimidinyl; wherein each Het is optionally substituted with one, two or three substitutents each independently selected from halo, $C_{1-4}$alkyl, $C_{1-4}$alkyloxy, $C_{1-4}$alkylthio, hydroxy, amino, mono- or di($C_{1-4}$alkyl)amino, hydroxycarbonyl, $C_{1-4}$alkyloxycarbonyl, $C_{1-4}$alkylsulfonylamino, aminocarbonyl, trifluoromethyl, $C_{1-4}$alkyloxycarbonylamino, di($C_{1-4}$alkyloxycarbonyl)amino, $C_{1-4}$alkylsulfonylaminocarbonyl, $C_{1-4}$alkylamino carbonyl, $C_{1-4}$alkyloxy $C_{1-6}$alkyl-oxycarbonylamino, di($C_{1-4}$alkyl)aminosulfonylaminocarbonyl, $C_{3-6}$cycloalkyl-sulfonylaminocarbonyl, HO—NH—(C═NH)—; oxazolyl or triazolyl each optionally substituted with one or two $C_{1-4}$alkyl;

or a pharmaceutically acceptable acid addition salt thereof.

As used in the foregoing definitions:
halo is generic to fluoro, chloro, bromo and iodo;
$C_{1-4}$alkyl defines straight and branched chain saturated hydrocarbon radicals having from 1 to 4 carbon atoms such as, for example, methyl, ethyl, propyl, butyl, 1-methyl-ethyl, 2-methylpropyl and the like;

$C_{1-6}$alkyl is meant to include $C_{1-4}$alkyl and the higher homologues thereof having 5 or 6 carbon atoms, such as, for example, 2-methylbutyl, pentyl, hexyl and the like;

$C_{3-6}$cycloalkyl is generic to cyclopropyl, cyclobutyl, cyclopentyl, and cyclohexyl;

polyhalo$C_{1-4}$alkyl is defined as polyhalosubstituted $C_{1-4}$alkyl, in particular $C_{1-4}$alkyl (as hereinabove defined) substituted with 2 to 6 halogen atoms such as difluoromethyl, trifluoromethyl, trifluoroethyl, and the like.

The term "compounds of the invention" as used herein, is meant to include the compounds of formula (I), and the salts and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the terms "compound of formula (I)" and "intermediates of synthesis of formula (I)" are meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers. Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light. When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

Some of the compounds according to formula (I) may also exist in their tautomeric form. Such forms in so far as they may exist, although not explicitly indicated in the above formula (I) are intended to be included within the scope of the present invention.

It follows that a single compound may exist in both stereoisomeric and tautomeric form.

For the avoidance of doubt, compounds of formula (I) may contain the stated atoms in any of their natural or non-natural isotopic forms. In this respect, embodiments of the invention that may be mentioned include those in which (a) the compound of formula (I) is not isotopically enriched or labelled with respect to any atoms of the compound; and (b) the compound of formula (I) is isotopically enriched or labelled with respect to one or more atoms of the compound. Compounds of formula (I) that are isotopically enriched or labelled (with respect to one or more atoms of the compound) with one or more stable isotopes include, for example, compounds of formula (I) that are isotopically enriched or labelled with one or more atoms such as deuterium, $^{13}C$, $^{14}C$, $^{14}N$, $^{15}O$ or the like.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) may exist in both unsolvated and solvated forms. The term 'solvate' is used herein to describe a molecular association comprising a compound of the invention and one or more pharmaceutically acceptable solvent molecules, e.g. water or ethanol. The term 'hydrate' is used when said solvent is water. Interesting compounds of formula (I) are those compounds of formula (I) wherein one or more of the following restrictions apply:

a) $R^1$ is hydrogen; or
b) $R^1$ is $C_{1-4}$alkyl, mono- or di($C_{1-4}$alkyl)amino, or Heterocyclyl$^1$; or
c) $R^1$ is Heterocyclyl$^1$; or
d) $R^2$ is hydrogen; or
e) $R^2$ is $C_{1-4}$alkyl; or
f) $R^3$ is $C_{3-6}$cycloalkyl; or
g) $R^3$ is $C_{1-4}$alkyl, mono- or di($C_{1-4}$alkyl)amino; or
h) $R^3$ is Heterocyclyl$^2$; or
i) $R^4$ is hydrogen; or
j) Heterocyclyl$^1$ is piperazinyl optionally substituted with one substituent selected from $C_{1-4}$alkyl, hydroxy, halo, polyhalo$C_{1-4}$alkyl, $C_{1-4}$alkyloxycarbonyl, amino, $C_{1-4}$alkylaminocarbonyl, or $C_{1-4}$alkylsulfonyl; or
k) Heterocyclyl$^1$ is morpholinyl optionally substituted with one substituent selected from $C_{1-4}$alkyl, hydroxy, halo, polyhalo$C_{1-4}$alkyl, $C_{1-4}$alkyloxycarbonyl, amino, $C_{1-4}$alkylaminocarbonyl, or $C_{1-4}$alkylsulfonyl; or l) Het is quinazolinyl optionally substituted with one, two or three substitutents each independently selected from halo, $C_{1-4}$alkyl, $C_{1-4}$alkyloxy, $C_{1-4}$alkylthio, hydroxy, amino, mono- or di($C_{1-4}$alkyl)amino, hydroxycarbonyl, $C_{1-4}$alkyloxycarbonyl, $C_{1-4}$alkylsulfonylamino, aminocarbonyl, trifluoromethyl, $C_{1-4}$alkyloxycarbonylamino, di($C_{1-4}$alkyloxycarbonyl)amino, $C_{1-4}$alkylsulfonylaminocarbonyl, $C_{1-4}$alkylaminocarbonyl, $C_{1-4}$alkyloxy $C_{1-6}$alkyloxycarbonylamino, di($C_{1-4}$alkyl)aminosulfonylaminocarbonyl, $C_{3-6}$cycloalkylsulfonylaminocarbonyl, HO—NH—(C=NH)—; oxazolyl or triazolyl each optionally substituted with one or two $C_{1-4}$alkyl.

In a first embodiment the present invention concerns compounds of formula (I), including any stereochemically isomeric form thereof, wherein
$R^1$ is hydrogen, $C_{1-4}$alkyl, mono- or di($C_{1-4}$alkyl)amino, or Heterocyclyl$^1$;
$R^2$ is hydrogen or $C_{1-4}$alkyl;
$R^3$ is $C_{3-6}$cycloalkyl or Heterocyclyl$^2$;
$R^4$ is hydrogen;
Heterocyclyl$^1$ is piperazinyl or morpholinyl; wherein each Heterocyclyl$^1$ is optionally substituted with one substituent selected from $C_{1-4}$alkyloxycarbonyl, $C_{1-4}$alkylaminocarbonyl, or $C_{1-4}$alkylsulfonyl;
Heterocyclyl$^2$ is azetidinyl, or pyrrolidinyl; wherein each Heterocyclyl$^2$ is optionally substituted with one substituent selected from hydroxy or amino;
Het is selected from quinazolinyl, pyrido[2,3-d]pyrimidinyl, thiazolo[5,4-d]-pyrimidinyl, 7H-pyrrolo[2,3-d]pyrimidinyl, oxazolo[5,4-d]pyrimidinyl, or thieno[2,3-d]pyrimidinyl; wherein each Het is optionally substituted with one, two or three substituents each independently selected from halo, $C_{1-4}$alkyl, $C_{1-4}$alkyloxy, $C_{1-4}$alkylthio, hydroxy, hydroxycarbonyl, $C_{1-4}$alkyloxycarbonyl, $C_{1-4}$alkylsulfonylamino, aminocarbonyl, trifluoromethyl, $C_{1-4}$alkyloxy-carbonylamino, di($C_{1-4}$alkyloxycarbonyl)amino, $C_{1-4}$alkylsulfonylamino-carbonyl, $C_{1-4}$alkylaminocarbonyl, $C_{1-4}$alkyloxy$C_{1-6}$alkyloxycarbonylamino, di($C_{1-4}$alkyl)aminosulfonylaminocarbonyl, $C_{3-6}$cycloalkylsulfonylamino-carbonyl, HO—NH—(C=NH)—; oxazolyl or triazolyl each optionally substituted with one or two $C_{1-4}$alkyl;
or a pharmaceutically acceptable acid addition salt thereof.

A first group of compounds of formula (I) are those compounds of formula (I) wherein $R^1$ is Heterocyclyl$^1$, $R^2$ is hydrogen, and $R^3$ is Heterocyclyl$^2$.

A second group of compounds of formula (I) are those compounds of formula (I) wherein $R^1$ is hydrogen, $R^2$ is $C_{1-4}$alkyl, and $R^3$ is Heterocyclyl$^2$.

A third group of compounds of formula (I) are those compounds of formula (I) wherein $R^1$ is hydrogen, $R^2$ is hydrogen, and $R^3$ is Heterocyclyl$^2$.

A fourth group of compounds of formula (I) are those compounds of formula (I) wherein $R^1$ is $C_{1-4}$alkyl, $R^2$ is hydrogen, and $R^3$ is Heterocyclyl$^2$.

A 5$^{th}$ group of compounds of formula (I) are those compounds of formula (I) wherein $R^1$ is hydrogen, $R^2$ is hydrogen, and $R^3$ is $C_{1-4}$alkyl.

A 6$^{th}$ group of compounds of formula (I) are those compounds of formula (I) wherein $R^1$ is hydrogen, $R^2$ is hydrogen, and $R^3$ is $C_{3-6}$cycloalkyl.

A 7$^{th}$ group of compounds of formula (I) are those compounds of formula (I) wherein Het is quinazolinyl.

Compounds of formula (I), or their pharmaceutically acceptable salts, can be prepared according to the reaction schemes discussed herein below using synthetic methods known in the art of organic chemistry, or modifications and derivatisations that are familiar to those skilled in the art. The starting materials used herein are commercially available or may be prepared by routine methods known in the art such as those methods disclosed in standard reference books. Preferred methods include, but are not limited to, those described below.

During any of the following synthetic sequences it may be necessary and/or desirable to protect sensitive or reactive groups on any of the molecules concerned. This can be achieved by means of conventional protecting groups well known the skilled person.

Unless otherwise indicated, the substituents in the schemes are defined as above. Isolation and purification of the products is accomplished by standard procedures, which are known to a chemist of ordinary skill.

General schemes 1-3 describe methods that were used to prepare compounds of the invention. The general methods described in these schemes can also be used to prepare additional compounds of the invention.

The starting material I is a protected (PG) piperidine bearing a carboxyl group on the carbon atom adjacent to the ring nitrogen that preferably has the (S) stereochemistry. This piperidine can also be substituted with different groups. Protecting groups on the piperidine ring nitrogen are preferably BOC or CBZ and can be introduced or removed during the synthesis using methods described in; Green and Wutts, protecting groups in Organic Synthesis 3$^{rd}$ Edition. In scheme 1 the carboxylic acid group on the N-protected cyclic aminoheterocycle I is first activated with a leaving group. Typical leaving groups are alkyl ester (e.g. methyl or ethyl ester) and these are generated by treatment of the carboxylic acid with the appropriate alcohol under non- or low-aqueous acidic conditions or by treatment with methyl iodide in the presence of a base like cesium carbonate or a like. Alternatively the acid can be activated as the Weinreb amide using standard peptide coupling procedures e.g. EDCI/HOBT, HATU, DCC, etc. Once the acid is activated as the ester or Weinreb amide II, the addition of an acetonitrile anion is performed. The anion generated from acetonitrile and a strong base e.g. lithium or sodium haxamethyldisilazide (LiHMDS) or alkyl lithium bases e.g. nBuLi, and when reacted with the ester or Weinreb amide generates the cyano ketone III. Reaction of the cyano ketone with hydrazine acetate salt then generates the aminopyrrazole intermediate IV. This is a key intermediate in the formation of the bicyclic heterocycles VI with different side chains through different condensation reactions. Condensation of amino pyrrazole IV with the malonate V generates the bicyclic analog VI. Treatment of VI with neat POCl$_3$ under elevated temperature (in some cases organic bases like diisopropylethyl amine or triethylamine can improve the reaction) then affords the dichloride VII. Under the POCl$_3$ conditions acidic labile protecting groups e.g. BOC are typically removed but if this is partial further treatment with acid e.g. 4N HCl in dioxane can be used to remove the remaining BOC protected material. If other protecting groups are utilized then procedures described in Green and Wutts, Protecting groups in Organic Synthesis 3$^{rd}$ Edition can be used to remove the protecting group. Displacement of the chloride adjacent to the bridgehead nitrogen on VII can be effected with nucleophiles VIII, typically at room temperature to provide IX. A typical nucleophile VIII would be an amine that can be reacted in the absence or presence of a base such as triethylamine. The second and less reactive chloride is then displaced typically at elevated temperatures above 50° C. The result of these nucleophilic amine displacements are compounds of structure XI (scheme 1).

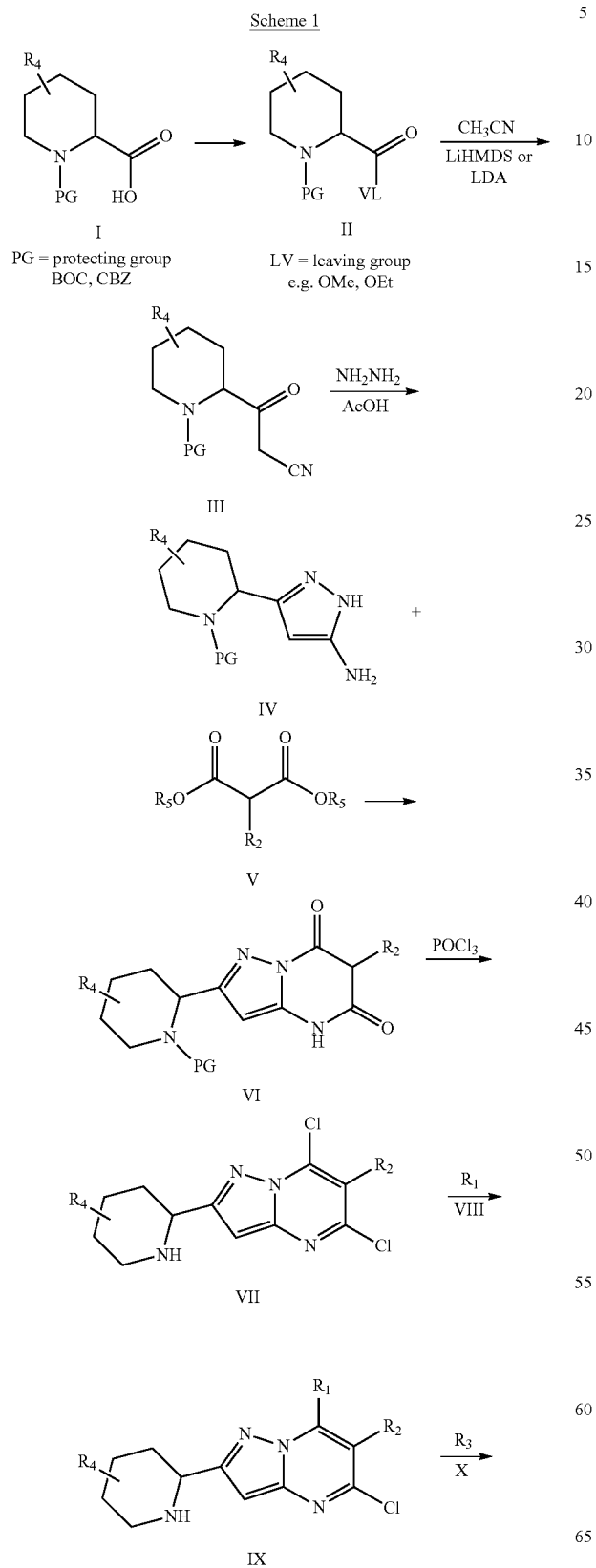

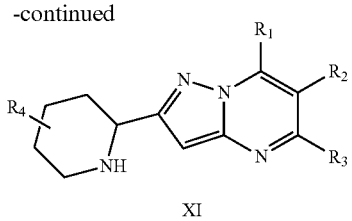

Compounds XIII may be synthesized according to embodiments disclosed herein from a compound having an amino group XI, and a heterocyclic halide compound XII. The reaction may be performed in the presence of a base and a Group 8-10 transition metal catalyst. One example of a reaction between a heterocyclic halide compound and an amine to produce an N-heterocyclic amine compound may be represented in scheme 2. Briefly, an heterocyclic halide XII compound is reacted with an amine compound XI in the presence of a base and a Group 8-10 transition metal (M) complex including a chelating ligand (LL) to form an N-aryl amine compound. The transition metal catalyst according to embodiments disclosed herein is a Group 8-10 transition metal complex. In certain embodiments, the Group 8-10 transition metal comprises at least one of palladium, platinum, and nickel. In some embodiments, the Group 8-10 transition metal is palladium.

The heterocyclic compound used in the process of the present invention may be any heterocyclic compound of formula XII:

Het-X                                    formula XII

Preferred heterocyclic groups in compound of formula XII:

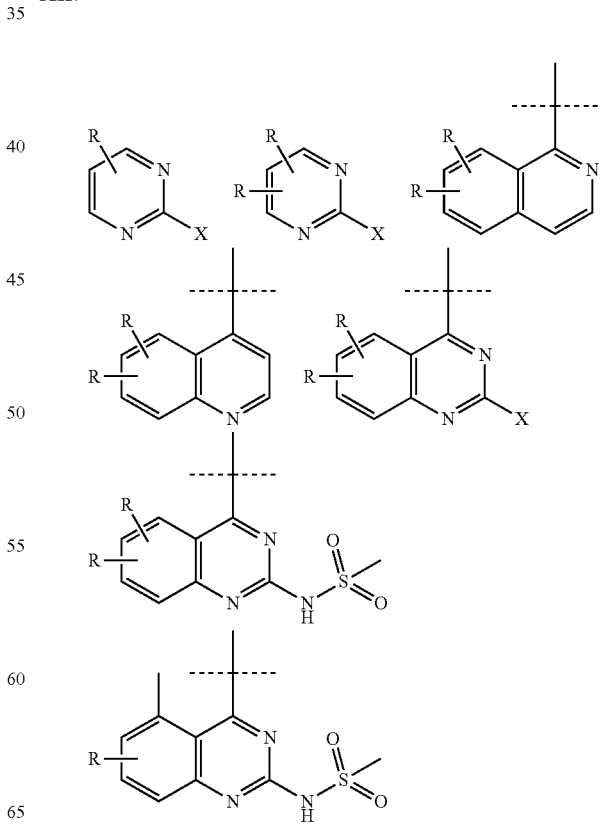

In formula XII, X may be any halide atom (F, Cl, Br, I), or any sulfur-containing leaving group (e.g., triflate, sulfonate, tosylate, and the like) known in the art. Chlorides are especially preferred in the process of the present invention.

Scheme 2

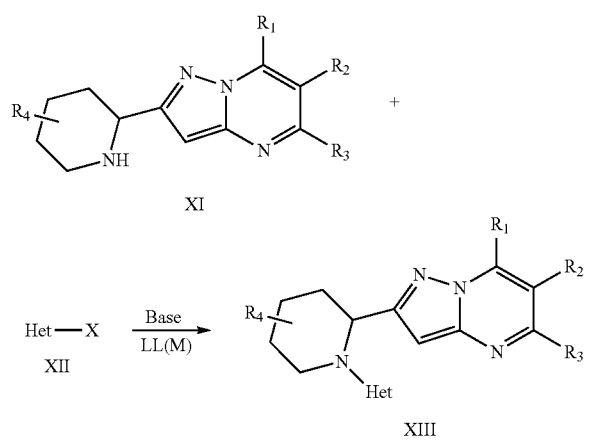

An alternative condensation of the aminopyrrazole IV using beta-keto esters VIX (e.g. 2-methylacetoacetate) in the presence of acid (acetic acid) at elevated temperature leads to the pyrrazo-pyrimidinone scaffold XV. Treatment of XV with neat POCl₃ under elevated temperature (in some cases hindered bases like diisopropylethyl amine can improve the reaction) then affords the dichloride XVI. Under the POCl₃ conditions acidic labile protecting groups e.g. BOC are typically removed but if this is partial further treatment with acid e.g. 4N HCl in dioxane can be used to remove the remaining BOC protected material. If other protecting groups are utilized then procedures described in Green and Wutts, Protecting groups in Organic Synthesis 3$^{rd}$ Edition can be used to remove the protecting group. Displacement of the chloride adjacent to the bridgehead nitrogen on XVI can be effected with nucleophiles VIII, typically at room temperature to provide compounds of type XVII. A typical nucleophile would be an amine that can be reacted in the absence or presence of a base such as triethylamine then allows the free amine XVII to be alkylated by a variety of heterocycles as described in scheme 2 to produces the final compounds XVIII scheme 3.

Scheme 3

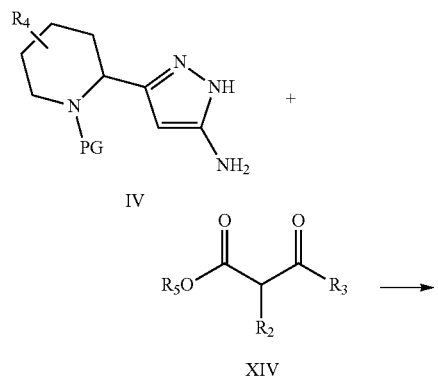

A further alternative cyclisation of the amino pyrrazole IV involves treatment with an acrylate e.g. XIX in the presence of base e.g. cesium carbonate, and heat to generate XX. Further treatment of XX to activate that OH as a leaving group can include conversion to a chloride XXI using POCl₃ and heat. Acidic protecting groups e.g. BOC can be removed under the POCl₃ conditions, or if not, following procedures outlined in Green and Wurtts, Protecting groups in Organic Synthesis 3$^{rd}$ Edition, any protecting groups can be removed. The chloride can be displaced by nucleophiles X to generate compounds XXII. Finally the free NH compound XXII is then alkylated as previously described in scheme 2 to give compounds of type XXIII (scheme 4).

Scheme 4

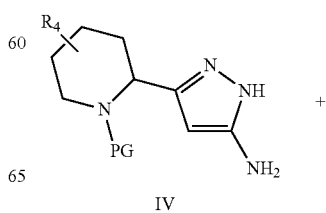

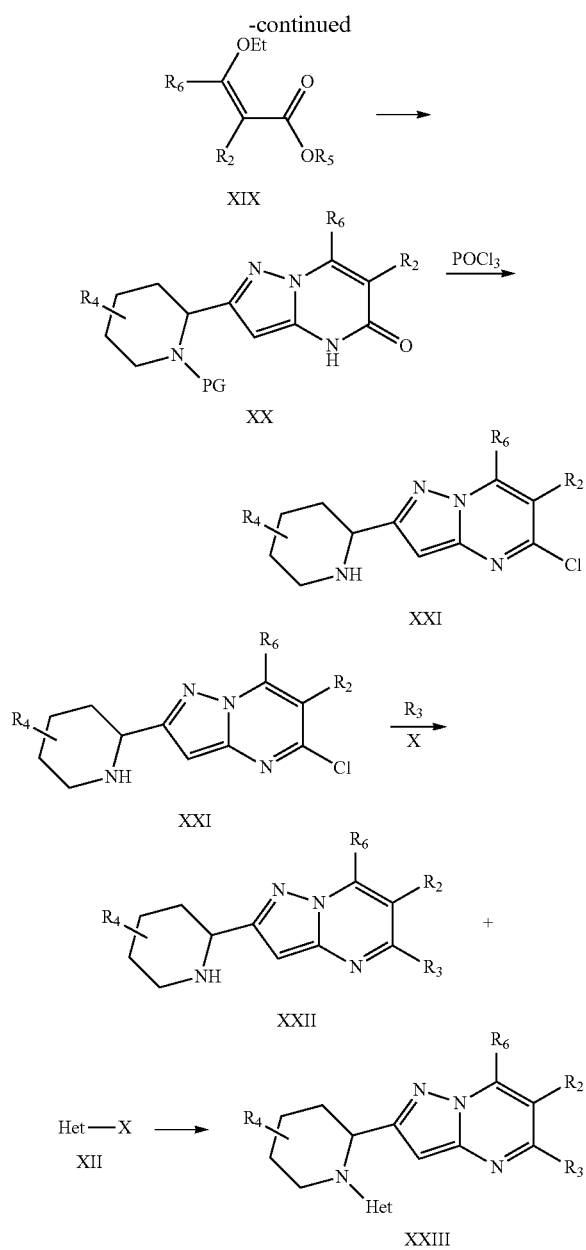

the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailabilty, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. in Antiviral Research, 38, p. 31-42 (1998).

Additionally the present invention provides pharmaceutical compositions comprising at least one pharmaceutically acceptable carrier and a therapeutically effective amount of a compound of formula (I).

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the The compounds of formula (I) may further be prepared by converting compounds of formula (I) into each other according to art-known group transformation reactions.

The starting materials and some of the intermediates are known compounds and are commercially available or may be prepared according to conventional reaction procedures generally known in the art.

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1',6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of formula (I) may also be formulated in rectal compositions such as suppositories or retention enemas, e.g. containing conventional suppository bases such as cocoa butter and/or other glycerides.

In general it is contemplated that an antivirally effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

The invention will hereinafter be illustrated with reference to the following, non-limiting examples.

EXPERIMENTAL PART

Abbreviations $(M+H)^+$ protonated molecular ion
aq. aqueous

Boc tert-butyloxycarbonyl
br broad
$CH_3Cl$ chloroform
$CH_3CN$ acetonitrile
$CH_3OH$ methanol
$CH_3ONa$ sodium methanolate
d doublet
DCM dichloromethane
DIEA N,N-diisopropylethylamine
DIPE diisopropylether
DMF dimethyl formamide
DMSO dimethyl sulfoxide
Et ethyl
eq. equivalent
EtOAc ethyl acetate
HOAc acetic acid
LiHMDS lithium bis(trimethylsilyl)amide
m/z: mass-to-charge ratio
Me methyl
MeCN acetonitrile
MeOH methanol
EtOH ethanol
MHz megahertz
min minute(s)
$N_2$ nitrogen
$Na_2SO_4$ sodium sulfate
NMR nuclear magnetic resonance (spectroscopy)
Pd(OAc)2 palladium (II) acetate
Ph phenyl
q quartet
RT room temperature
s singlet
sat saturated
t triplet
TEA triethyl amine
TFA trifluoroacetic acid
THF tetrahydrofuran
NMR For a number of compounds, $^1H$ NMR spectra were recorded on a Bruker DPX-400 spectrometer operating at 400 MHz or on a Bruker DPX-360 operating at 360 MHz using chloroform-d (deuterated chloroform, $CDCl_3$) or DMSO-$d_6$ (deuterated DMSO, dimethyl-d6 sulfoxide) as solvent. Chemical shifts (δ) are reported in parts per million (ppm) relative to tetramethylsilane (TMS), which was used as internal standard.

Optical Rotation:

The optical rotation was measured using a Perkin Elmer 341 polarimeter. [c]$D_{20}$ indicates the optical rotation measured with light at the wavelength of the D-line of sodium (589 nm) at a temperature of 20° C. The cell pathlength is 1 dm. Behind the actual value the concentration and solvent of the solution which was used to measure the optical rotation are mentioned.

Experimental Part

A. Chemical of Intermediates and Compounds of Formula (I)

Synthesis of 4-(5-(azetidin-1-yl)-2-(1-(6-chloroquinazolin-4-yl)piperidin-2-yl)-pyrazolo[1,5-a]pyrimidin-7-yl)morpholine P1

Scheme 5

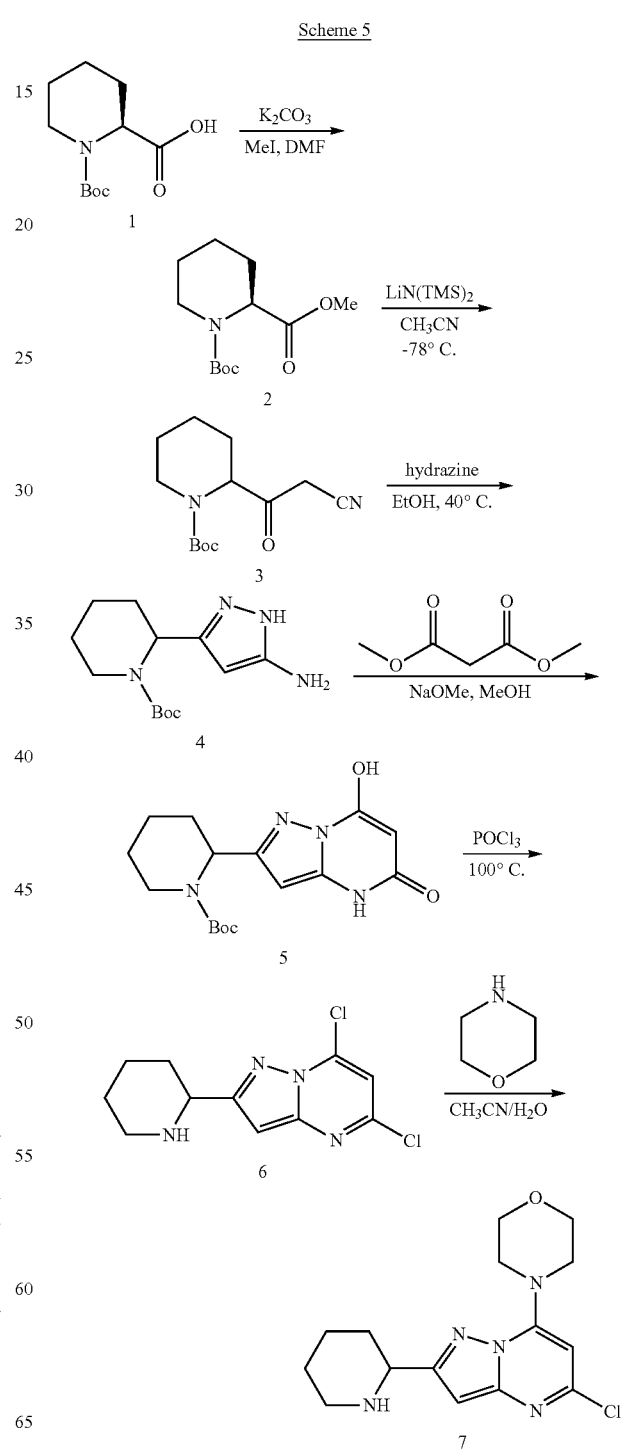

17
-continued

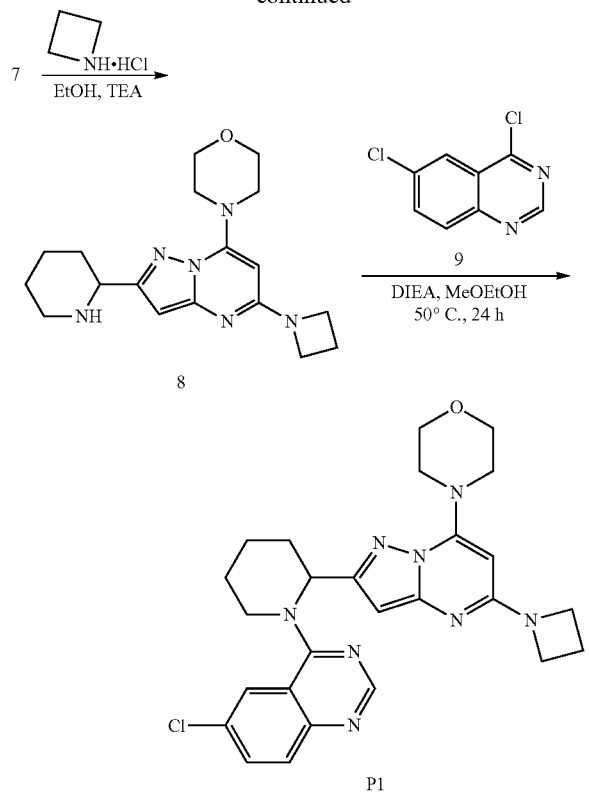

Step 1: Synthesis of (S)-1-tert-butyl 2-methyl piperidine-1,2-dicarboxylate 2

Potassium carbonate (108.50 g, 785.09 mmol) was added to a solution of (S)-1-(tert-butoxycarbonyl)piperidine-2-carboxylic acid 1 (90 g, 392.55 mmol) in DMF (900 ml). Iodomethane (83.58 g, 588.82 mmol) was added to the mixture. The mixture was stirred at room temperature overnight. Ethyl acetate was added to the reaction mixture. The resulting mixture was washed with water and brine. The organic layer was dried over $Na_2SO_4$, filtered and concentrated under vacuum to give intermediate 2 (90 g, yield: 85%).

m/z=244 (M+H)$^+$.

Step 2: synthesis of tert-butyl2-(2-cyanoacetyl)piperidine-1-carboxylate 3

To a solution of $CH_3CN$ (1.30 ml, 24.66 mmol) in dry THF (40 ml) was added dropwise LiHMDS (22.61 ml, 22.61 mmol) at −78° C. The solution was stirred for 20 minutes at −78° C. A solution of 2 (5 g, 22.55 mmol) in dry THF (10 ml) was added dropwise to the mixture. The resulting mixture was stirred for 2 hours. Then the mixture was cooled to −78° C. and a solution of HOAc (5 ml, 76.67 mmol) in THF (50 ml) was added dropwise to the mixture. The solution was warmed to room temperature. The solvent was removed under vacuum. The residue was dissolved in ethyl acetate and washed with brine, dried $Na_2SO_4$, filtered and concentrated under vacuum to give the crude intermediate 3 (4 g, yield: 69%).

m/z=253 (M+H)$^+$.

18

Step 3: tert-butyl2-(5-amino-1H-pyrazol-3-yl)piperidine-1-carboxylate 4

Hydrazine hydrate (100 ml) and ethanol (500 ml) were added to intermediate 3 (80 g, 317.70 mmol). The mixture was stirred at room temperature overnight. The solvent was removed under vacuum. The residue was dissolved in ethyl acetate, washed with brine.

The organic layer was dried over $Na_2SO_4$, filtered and concentrated under vacuum to give intermediate 4 (80 g, yield: 76%).

m/z=267 (M+H)$^+$.

Step 4: synthesis of tert-butyl 2-(7-hydroxy-5-oxo-4,5-dihydropyrazolo[1,5-a]-pyrimidin-2-yl)piperidine-1-carboxylate 5

Intermediate 4 (70 g, 262.82 mmol) was dissolved in methanol (700 ml), then Dimethyl malonate (85.19 g, 394.23 mmol) was added to the solution, followed by the addition of a solution of $CH_3ONa$ in $CH_3OH$ (25%, 85.19 g, 394.23 mmol). The reaction mixture was heated to reflux overnight. The solvent was removed under vacuum. Water was added to the residue, the pH was adjusted to 6-7 by addition of acetic acid, the mixture was extracted with ethyl acetate, the organic layer was washed with brine, dried over $Na_2SO_4$, filtered and concentrated under vacuum to give intermediate 5 (85 g, yield: 63%) which was used for the next reaction directly.

m/z=335 (M+H)$^+$.

Step 5: synthesis of 5,7-dichloro-2-(piperidin-2-yl)pyrazolo[1,5-a]pyrimidine 6

Intermediate 5 (25 g, 74.77 mmol)) was added to neat $POCl_3$ (100 ml). The reaction mixture was heated to 100° C. for 3 hours. The solvent was evaporated to yield intermediate 6 (15 g, yield: 63%) which was used for the next reaction directly.

m/z=272 (M+H)$^+$.

Step 6: synthesis of 4-(5-chloro-2-(piperidin-2-yl)pyrazolo[1,5-a]pyrimidin-7-yl)-morpholine 7

Intermediate 6 (35 g, 129.08 mmol) was added to $CH_3CN$ (100 ml) and $H_2O$ (100 ml). To the above mixture was added $NaHCO_3$ (21.69 g, 258.16 mmol) and morpholine (11.25 g, 129.08 mmol). The reaction mixture was stirred at room temperature for 1 hour, solvents were then evaporated, dichloromethane was added, the mixture was filtered and the filtrate was evaporated. The residue was purified by column chromatography over silica gel (eluent: dichloromethane: ethyl acetate from 1:0 to 0:1) to yield intermediate 7 (25 g, yield: 51%).

m/z=322 (M+H)$^+$.

Step 7: synthesis of 4-(5-(azetidin-1-yl)-2-(piperidin-2-yl)pyrazolo[1,5-a]pyrimidin-7-yl)morpholine 8

Azetidine hydrochloride (29.07 g, 310.75 mmol) and TEA (62.89 g, 621.49 mmol) were added to a solution of intermediate 7 (20 g, 62.15 mmol) in ethanol (1000 ml). The resulting mixture was heated to 80° C. for 2 hours. The solvent was evaporated. The resulting crude material was purified by column chromatography over silica gel (eluent: methanol/ethyl acetate 1/10). The collected fractions were concentrated under vacuum. The residue was dissolved in CH₃CN (200 ml). K₂CO₃ (100 g, 723.54 mmol) was added to the solution. The mixture was stirred overnight at room temperature. The resulting mixture was filtered and evaporated to remove the solvent in vacuum. The residue was lyophilized. Intermediate 8 was isolated (6 g, yield: 27%).
m/z=343 (M+H)⁺.

¹H NMR (400 MHz, CDCl₃) δ ppm 1.52-1.66 (m, 4H) 1.90 (m, 1H) 1.97 (m, 1H) 2.37-2.40 (m, 2H) 2.79 (m, 1H) 3.31 (m, 1H) 3.55-3.58 (m, 4H) 3.81 (m, 1H) 3.93-3.95 (m, 4H) 4.09-4.13 (m, 4H) 5.09 (s, 1H) 6.04 (s, 1H).

Step 8: synthesis of 4,6-dichloroquinazoline 9

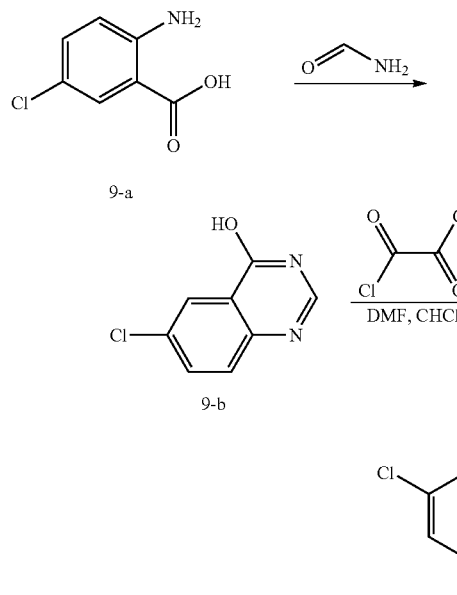

Synthesis of 6-chloroquinazolin-4-ol 9-b

2-Amino-5-chlorobenzoic acid 9-a (5 g, 29 mmol) was added to formamide (30 ml). The reaction mixture was heated to 100° C. for 3 hours. The solid was collected by filtration. The solid was washed several times with ethanol to yield intermediate 9-b (5 g, 86%). m/z=181 (M+H)⁺.

Synthesis of 4,6-dichloroquinazoline 9

Intermediate 9-b (3 g, 16.61 mmol) was dissolved in CHCl₃ (30 ml). Oxalyl chloride (2.8 g, 33.22 mmol) and DMF (0.1 ml) were added. The mixture was heated to 100° C. for 3 hours. Solvent was evaporated to get intermediate 9 (2.5 g, yield: 68%).
m/z=200 (M+H)⁺.

Step 9: synthesis of 4-(5-(azetidin-1-yl)-2-(1-(6-chloroquinazolin-4-yl)piperidin-2-yl)-pyrazolo[1,5-a]pyrimidin-7-yl)morpholine P1

Intermediate 8 TFA salt (400 mg, 0.87 mmol) was dissolved in methoxyethanol (20 mL), intermediate 9 (235 mg, 1.18 mmol) and diisopropyl ethylamine (0.6 mL, 3.5 mmol) were added. The resulting mixture was stirred at 50° C. for 24 hours. The mixture was poured in an iced watered solution and stirred for 15 minutes. The solid was successively filtered off, washed with water, dissolved in dichloromethane, dried over MgSO₄ and filtered. The resulting solution was concentrated and the solid was dried in the oven to yield a yellowish solid compound P1 (380 mg, 85%).
m/z=506 (M+H)⁺.

¹H NMR (400 MHz, DMSO-d6) δ ppm 1.66-1.86 (m, 5H), 1.99-2.12 (m, 1H), 2.25-2.37 (m, 3H), 3.47-3.58 (m, 6H), 3.63-3.75 (m, 5H), 3.96-4.07 (m, 5H), 4.21 (d, J=13.4 Hz, 1H), 5.25 (s, 1H), 5.81-5.86 (m, 1H), 5.89 (s, 1H), 7.72 (dd, J=9.0, 2.2 Hz, 1H), 7.78 (d, J=9.0 Hz, 1H), 8.07 (d, J=2.2 Hz, 1H), 8.57 (s, 1H)

Synthesis of (S)-4-(5-(azetidin-1-yl)-2-(1-(6-chloroquinazolin-4-yl)piperidin-2-yl)-pyrazolo[1,5-a]pyrimidin-7-yl)morpholine P2 and (R)-4-(5-(azetidin-1-yl)-2-(1-(6-chloroquinazolin-4-yl)piperidin-2-yl)pyrazolo[1,5-a]pyrimidin-7-yl)morpholine P3

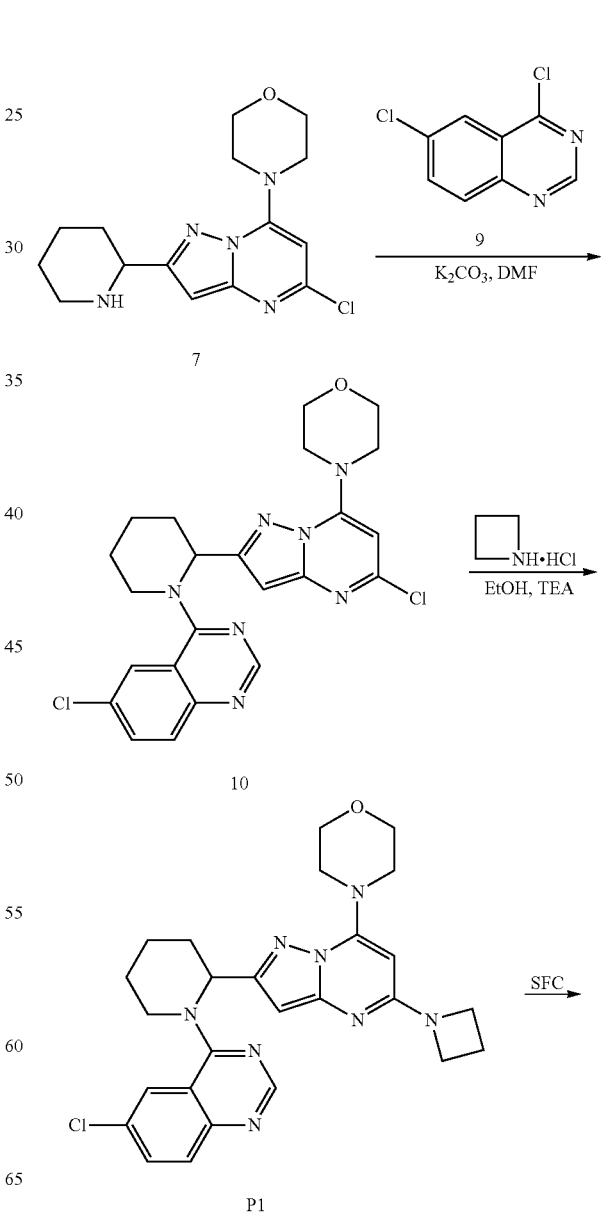

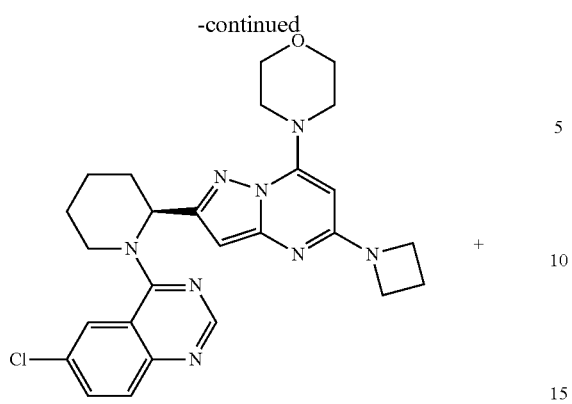

P2 m/z=506 (M+H)$^+$.

$^1$H NMR (400 MHz, CDCl$_3$) δ ppm 1.79-1.83 (m, 4H) 2.01-2.06 (m, 1H) 2.37-2.49 (m, 3H) 3.45-3.49 (m, 3H) 3.55-3.63 (m, 2H) 3.80-3.90 (m, 4H) 4.15 (m, 4H) 4.25 (m, 1H) 5.10 (s, 1H) 5.90 (s, 1H) 6.10 (s, 1H) 7.61 (dd, J1=9.2 Hz, J2=2.4 Hz, 1H) 7.80 (d, J=9.2 Hz, 2H) 8.03 (d, J=2.0 Hz, 1H) 8.68 (s, 1H).

P2: [α]$_D^{20}$=−280.83° (589 nm, c=0.24 w/v %, DMF, 20° C.)

P3: [α]$_D^{20}$=+270° (589 nm, c=0.24 w/v %, DMF, 20° C.)

Synthesis of 4-(5-(azetidin-1-yl)-2-(1-(6-methylquinazolin-4-yl)piperidin-2-yl)-pyrazolo[1,5-a]pyrimidin-7-yl)morpholine P4

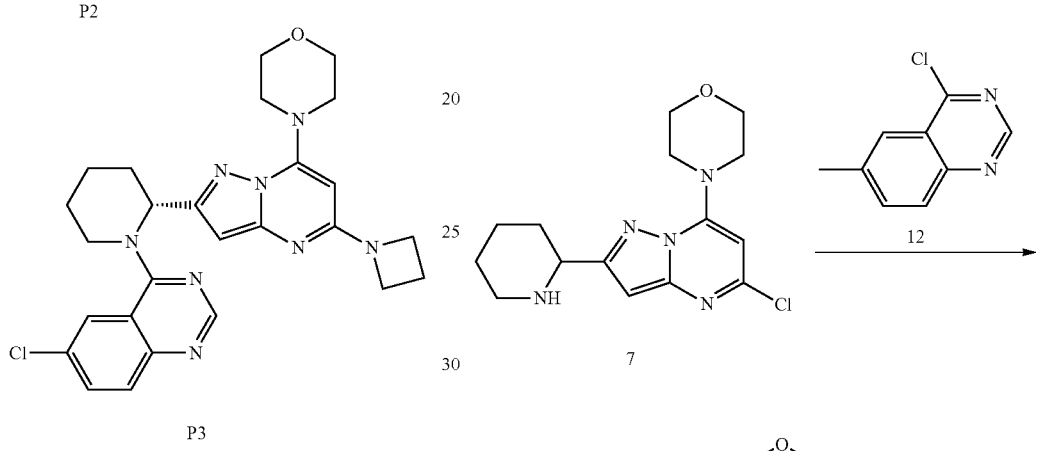

P3

Step 1: synthesis of 4-(5-chloro-2-(1-(6-chloroquinazolin-4-yl)piperidin-2-yl)-pyrazolo[1,5-a]pyrimidin-7-yl)morpholine 10

To a solution of intermediate 7 (1 g, 3.11 mmol) and intermediate 9 (0.62 g, 3.11 mmol) in DMF (20 ml) was added K$_2$CO$_3$ (2.15 g, 15.54 mmol). The resulting mixture was stirred overnight at room temperature. Water was added, the mixture was extracted with ethyl acetate, the organic layer was washed with brine, dried over Na$_2$SO$_4$, filtered and concentrated under vacuum. The residue was purified by column chromatography over silica gel (eluent: petroleum ether:ethyl acetate from 10:1 to 0:1) to yield intermediate 10 (450 mg, yield: 27%).

m/z=485 (M+H)$^+$.

Step 2: synthesis of (S)-4-(5-(azetidin-1-yl)-2-(1-(6-chloroquinazolin-4-yl)piperidin-2-yl)pyrazolo[1,5-a]pyrimidin-7-yl)morpholine P2 and (R)-4-(5-(azetidin-1-yl)-2-(1-(6-chloroquinazolin-4-yl)piperidin-2-yl)pyrazolo[1,5-a]pyrimidin-7-yl)morpholine P3

Azetidine hydrochloride (0.39 g, 4.13 mmol) and TEA (0.84 g, 8.26 mmol) were added to a solution of intermediate 10 (0.4 g, 0.83 mmol) in ethanol (50 ml). The solution was heated to 80° C. for 2 hours. The solvent was evaporated. The residue was purified by SFC. The desired fractions were collected and evaporated. The residue was lyophilized to yield compound P2 (44.10 mg, yield: 10%) and compound P3 (43.30 mg, yield: 10%).

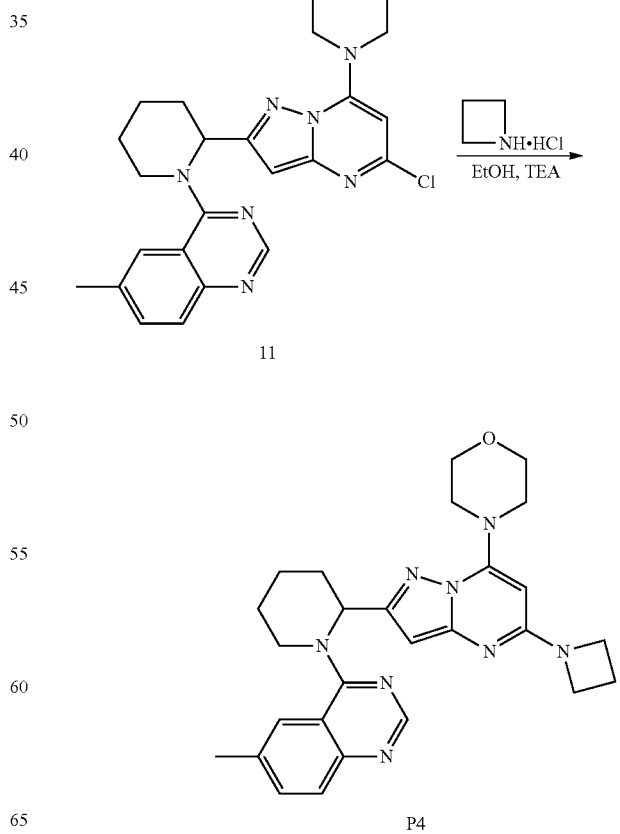

P4

Step 1: synthesis of 4-(5-chloro-2-(1-(6-methylquinazolin-4-yl)piperidin-2-yl)-pyrazolo[1,5-a]pyrimidin-7-yl)morpholine 11

Synthesis of 6-methylquinazolin-4-ol 12-b

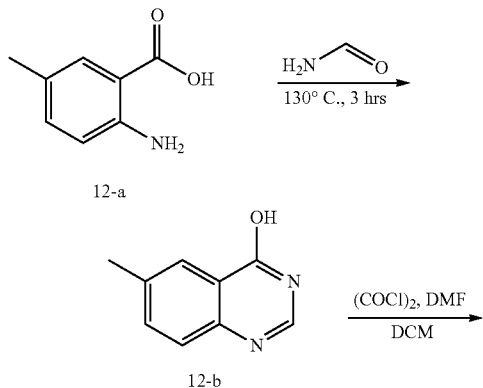

2-Amino-5-methylbenzoic acid 12-a (5 g, 33.08 mmol) was added to formamide (30 ml). The reaction mixture was heated to 100° C. for 6 hours. The solid was collected by filtration and washed several times with ethanol to give intermediate 12-b (4.5 g, 76%).

m/z=161 (M+H)$^+$.

Synthesis of 4-chloro-6-methylquinazoline 12

Intermediate 12-b (2.1 g, 13.11 mmol) was dissolved in CHCl$_3$ (30 ml). Oxalyl chloride (1.97 g, 23.26 mmol) and DMF (0.1 ml) were added. The mixture was heated to 100° C. for 3 hours. The solvent was evaporated to get intermediate 12 (1.5 g, 58%).

m/z=179 (M+H)$^+$.

To a solution of intermediate 7 (0.5 g, 1.55 mmol) and intermediate 12 (0.28 g, 1.55 mmol) in CH$_3$CN (10 ml) was added K$_2$CO$_3$ (1.07 g, 7.77 mmol). The resulting mixture was stirred for 72 hours at 50° C. The solvent was evaporated and the residue was dissolved in CH$_2$Cl$_2$. The resulting mixture was filtered and filtrate was evaporated. The residue was purified by column chromatography over silica gel (eluent: petroleum ether:ethyl acetate from 0:1 to 1:1) to yield intermediate 11 (350 mg, yield: 44%).

m/z=464 (M+H)$^+$.

Step 2: synthesis of 4-(5-chloro-2-(1-(6-methylquinazolin-4-yl)piperidin-2-yl)-pyrazolo[1,5-a]pyrimidin-7-yl)morpholine P4

Azetidine hydrochloride (0.30 g, 3.24 mmol) and TEA (0.66 g, 6.47 mmol) were added to a solution of intermediate 11 (0.3 g, 0.65 mmol) in ethanol (10 ml). The solution was heated to 80° C. for 2 hours. The solvent was evaporated. The residue was purified by HPLC. The desired fraction was collected and neutralized to pH=8-9 with NaHCO$_3$ solution and extracted with EtOAc. The organic layer was washed with brine, dried over Na$_2$SO$_4$ and filtered. The filtrate was concentrated under vacuum. The residue was lyophilized to yield compound P4 (111.00 mg, 35%).

m/z=485 (M+H)$^+$.

$^1$H NMR (400 MHz, CDCl$_3$) δ ppm 1.67-1.79 (m, 4H) 2.17 (m, 1H) 2.42 (m, 6H) 3.43-3.45 (m, 3H) 3.60-3.61 (m, 2H) 3.81 (m, 4H) 4.11 (m, 4H) 4.23 (m, 1H) 5.09 (s, 1H) 5.89 (s, 1H) 6.15 (s, 1H) 7.52 (d, J=9.2 Hz, 1H) 7.76-7.78 (m, 2H) 8.66 (s, 1H).

Synthesis of 4-(5-(azetidin-1-yl)-2-(1-(2-chloro-6-methylquinazolin-4-yl)piperidin-2-yl)pyrazolo[1,5-a]pyrimidin-7-yl)morpholine P5

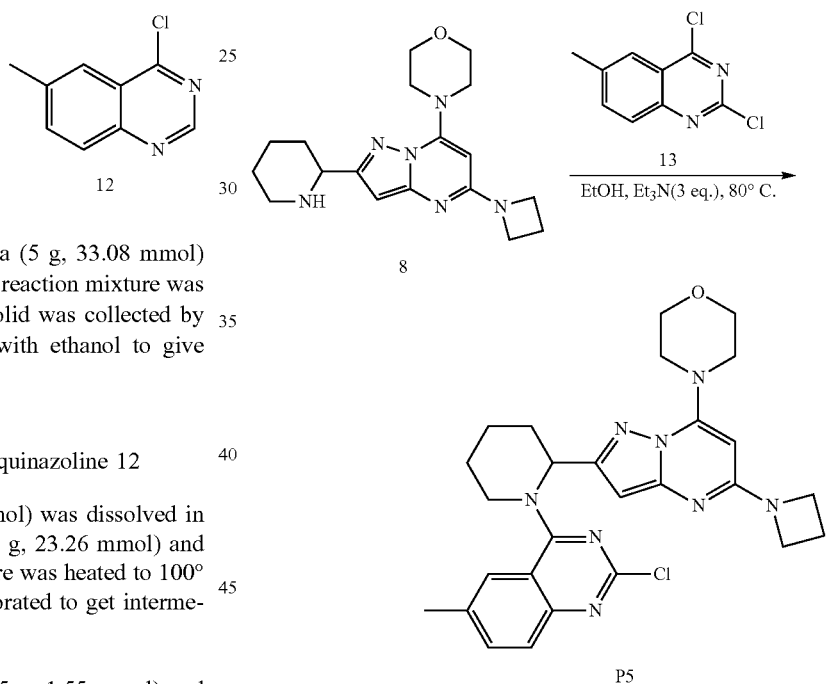

A mixture of intermediate 8 (500 mg, 1.460 mmol, 1 eq.), the commercially available 2,4-dichloro-6-methylquinazoline 13 (622 mg, 2.920 mmol, 2 eq.) and Et$_3$N (443 mg, 4.38 mmol, 3 eq.) in ethanol (20 ml) was stirred at 80° C. for 16 hours. The mixture was cooled to room temperature. The precipitate was filtered and collected. The solid was washed with cooled ethanol (2×3 ml) to yield compound P5 (540 mg, 69%)

m/z=520 (M+H)$^+$.

$^1$H NMR (400 MHz, CDCl$_3$) δ ppm 1.66-1.88 (m, 4H) 1.97-2.13 (m, 1H) 2.32-2.54 (m, 6H) 3.38-3.52 (m, 3H) 3.55-3.68 (m, 2H) 3.86 (m, 4H) 4.13 (t, J=7.53 Hz, 4H) 4.34 (d, J=12.80 Hz, 1H) 5.10 (s, 1H) 5.96 (br. s., 1H) 6.13 (s, 1H) 7.51 (dd, J1=8.53, J2=1.51 Hz, 1H) 7.69 (d, J=8.53 Hz, 1H) 7.74 (s, 1H).

Synthesis of N-(4-(2-(5-(azetidin-1-yl)-7-morpholinopyrazolo[1,5-a]pyrimidin-2-yl)piperidin-1-yl)-6-methylquinazolin-2-yl)methanesulfonamide P6

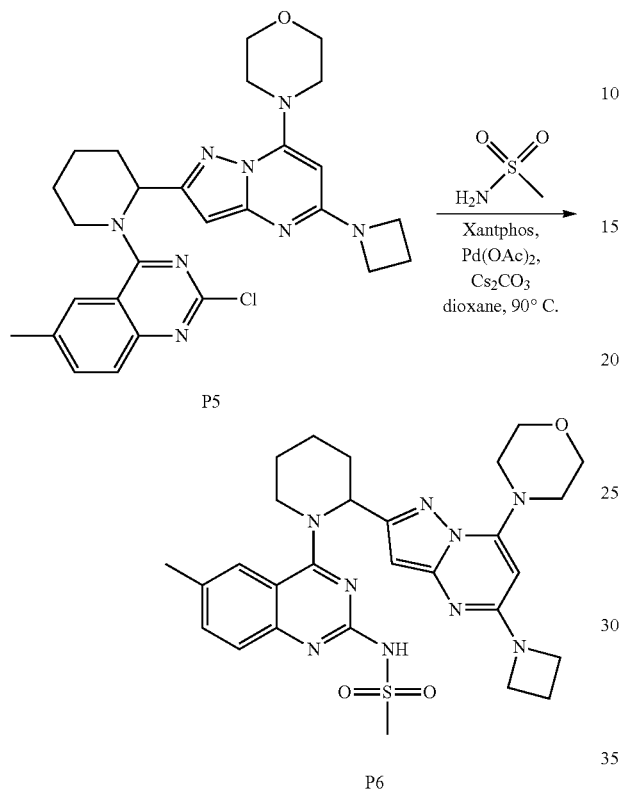

Palladium acetate (8.6 mg, 0.038 mmol, 0.1 eq.) was added to a mixture of compound P5 (200 mg, 0.385 mmol, 1 eq.), methanesulfonamide (73 mg, 0.77 mmol, 2 eq.), Xantphos (22 mg, 0.038 mmol, 0.1 eq.) and Cs$_2$CO$_3$ (250 mg, 0.77 mmol, 2 eq.) in Dioxane (6 ml). The resulting mixture was stirred at 90° C. for 1.5 hours under microwave. The precipitate was filtered and washed with ethyl acetate to yield the title compound P6 (98 mg, 42.34%).

m/z=578 (M+H)$^+$.

$^1$HNMR (400 MHz, CDCl$_3$): δ ppm 1.89 (m, 4H) 1.90 (m, 1H) 2.31 (s, 3H) 2.40 (m, 2H) 2.51 (m, 1H) 3.20 (s, 3H) 3.50 (m, 3H) 3.68 (m, 1H) 3.89 (m, 4H) 4.13 (m, 4H) 4.62 (br, 1H) 5.13 (s, 1H) 6.12 (s, 1H) 7.41-7.43 (d, J=8.4 Hz, 1H) 7.46-7.49 (d, J=8.8 Hz, 1H) 7.66 (s, 1H).

(R)—N-(4-(2-(5-(azetidin-1-yl)-7-morpholinopyrazolo[1,5-a]pyrimidin-2-yl)-piperidin-1-yl)-6-methylquinazolin-2-yl)methanesulfonamide P7 and (S)—N-(4-(2-(5-(azetidin-1-yl)-7-morpholinopyrazolo[1,5-a]pyrimidin-2-yl)piperidin-1-yl)-6-methylquinazolin-2-yl)methanesulfonamide P8

A purification was performed via Prep SFC (Stationary phase: Chiralpak Diacel AS 20×250 mm, Mobile phase: CO2, EtOH with 0.2% iPrNH2) giving both relative enantiomers:

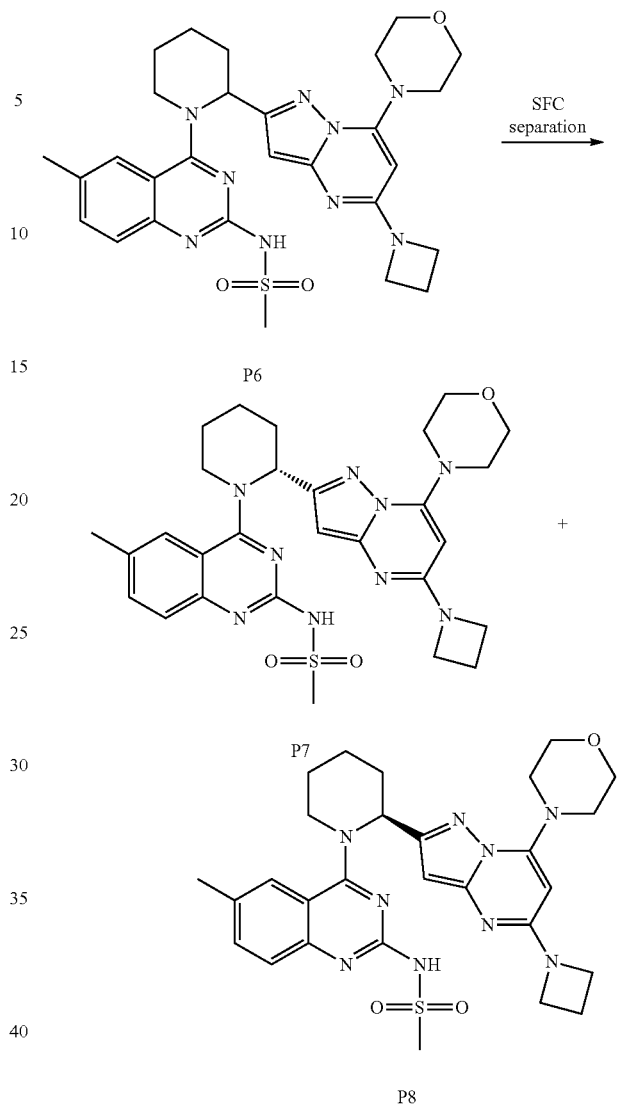

m/z=578 (M+H)$^+$.

$^1$HNMR (400 MHz, CDCl$_3$): δ ppm 1.89 (m, 4H) 1.90 (m, 1H) 2.31 (s, 3H) 2.40 (m, 2H) 2.51 (m, 1H) 3.20 (s, 3H) 3.50 (m, 3H) 3.68 (m, 1H) 3.89 (m, 4H) 4.13 (m, 4H) 4.62 (br, 1H) 5.13 (s, 1H) 6.12 (s, 1H) 7.41-7.43 (d, J=8.4 Hz, 1H) 7.46-7.49 (d, J=8.8 Hz, 1H) 7.66 (s, 1H).

Synthesis of N-(4-(2-(5-(azetidin-1-yl)-7-morpholinopyrazolo[1,5-a]pyrimidin-2-yl)piperidin-1-yl)-5-methylquinazolin-2-yl)methanesulfonamide P9

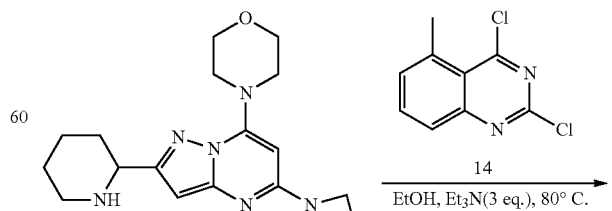

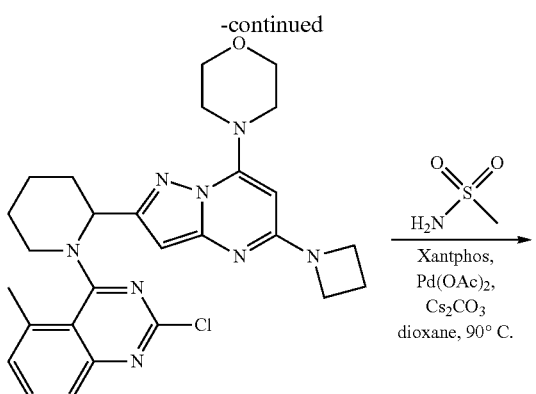

precipitate to form. The reaction mixture was stirred at room temperature overnight, the solution was neutralized to pH=7 with concentrated HCl and the white solid was filtered off. The obtained solid was washed with water, triturated with hot ethyl acetate (100 ml), and cooled to room temperature. The filtrate was collected and dried under vacuum to yield intermediate 14-b (6.4 g, yield: 49%).

m/z=177 (M+H)$^+$.

$^1$H NMR (400 MHz, DMSO-$d_6$) δ ppm 2.64 (s, 3H) 6.93 (d, J=7.48 Hz, 1H) 7.01 (d, J=8.14 Hz, 1H) 7.44 (t, J=7.81 Hz, 1H) 10.99 (s, 1H) 11.03 (br. s., 1H)

Step 2: synthesis of 2,4-dichloro-5-methylquinazoline 14

A mixture of intermediate 14-b (1 g, 5.68 mmol), diethylaniline (2.267 ml, 14.19 mmol) in POCl$_3$ (5 ml) was refluxed for 2 hours. The mixture was cautiously poured over crushed ice. The mixture was neutralized to pH=7 with saturated NaHCO$_3$. The resulting mixture was extracted with CH$_2$Cl$_2$ (2×15 ml). The combined organic layers were washed with brine, dried over Na$_2$SO$_4$ and filtered. The filtrate was concentrated under vacuum to yield intermediate 14 (950 mg, yield: 68%).

m/z=214 (M+H)$^+$.

Step 3: synthesis of 4-(5-(azetidin-1-yl)-2-(1-(2-chloro-6-methylquinazolin-4-yl)-piperidin-2-yl)pyrazolo[1,5-a]pyrimidin-7-yl)morpholine 15

A mixture of intermediate 8 (500 mg, 1.46 mmol), intermediate 14 (933.13 mg, 4.38 mmol) and triethyl amine (443.21 mg, 4.38 mmol) in EtOH (20 ml) was stirred at 80° C. for 16 hours. The mixture was cooled to room temperature. The precipitate was filtered and collected. The solid was washed with cooled ethanol (2×5 ml) to yield the desired compound 15 (400 mg, 48%).

m/z=520 (M+H)$^+$.

Step 4: synthesis of N-(4-(2-(5-(azetidin-1-yl)-7-morpholinopyrazolo[1,5-a]pyrimidin-2-yl)piperidin-1-yl)-5-methylquinazolin-2-yl)methanesulfonamide P9

To a mixture of compound 15 (200 mg, 0.385 mmol), methanesulfonamide (73.24 mg, 0.77 mmol), xantphos (23.15 mg, 0.04 mmol) and Cs$_2$CO$_3$ (250.88 mg, 0.77 mmol) in dioxane (6 ml) Pd(OAc)$_2$ (9 mg, 0.04 mmol) were added. The resulting mixture was stirred at 120° C. for 1.5 h under microwave. The mixture was filtered. The precipitate was treated with MeOH and filtered. The combined filtrates were concentrated under vacuum. The residue was purified and the pH of the fractions containing product was adjusted to 7-8 with saturated NaHCO$_3$. The organic solvent was evaporated under vacuum. The aqueous concentrate was extracted with CH$_2$Cl$_2$ (30 ml). The organic layer was concentrated under vacuum to yield compound P9 (105 mg, yield: 45%).

m/z=578 (M+H)$^+$.

$^1$H NMR (400 MHz, CDCl3) δ ppm 1.55-1.85 (m, 4H) 2.10-2.62 (m, 5H) 2.69-2.85 (m, 5H) 3.35 (s, 3H) 3.59-3.86

Synthesis of 2,4-dichloro-5-methylquinazoline 14

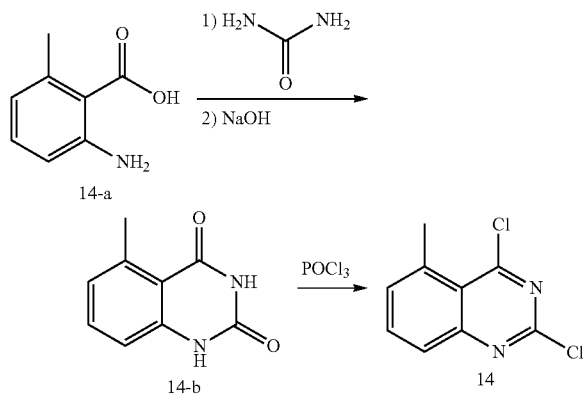

Step 1: synthesis of 5-methylquinazoline-2,4(1H,3H)-dione 14-b

2-Amino-6-methylbenzoic acid 14-a (10 g, 66.15 mmol) and urea (39.73 g, 661.54 mmol) were heated to 160° C. and stirred for 6 hours, the reaction mixture was cooled to 100° C. and 40 ml of H$_2$O was added. The obtained suspension was left to stir for 10 min and cooled to room temperature. The precipitate was filtered off and was dissolved in an aqueous 0.2 M sodium hydroxide solution (100 ml). The solution was heated to 100° C. for 5 min, causing a white (m, 8H) 4.07-4.17 (m, 4H) 5.21 (s, 1H) 5.75 (s, 1H) 7.17-7.23 (m, 2H) 7.55-7.58 (m, 1H).

Synthesis of N-(4-(2-(5-(azetidin-1-yl)-7-morpholinopyrazolo[1,5-a]pyrimidin-2-yl)piperidin-1-yl)quinazolin-2-yl)methanesulfonamide P10

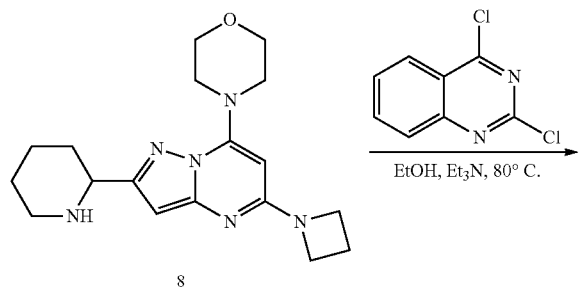

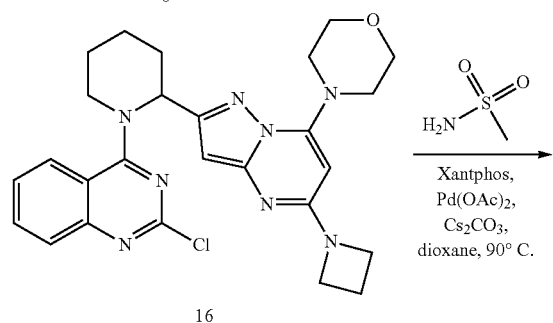

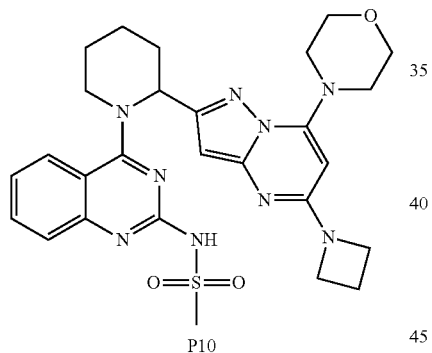

Step 1: synthesis of 4-(5-(azetidin-1-yl)-2-(1-(2-chloroquinazolin-4-yl)piperidin-2-yl)-pyrazolo[1,5-a]pyrimidin-7-yl)morpholine 16

The mixture of 8 (250 mg, 0.73 mmol, 1 eq.), 2,4-dichloroquinazoline (290 mg, 1.46 mmol, 2 eq.) and triethylamine (221 mg, 2.19 mmol, 3 eq.) in ethanol was stirred at 90° C. for 4 hours. The reaction was concentrated. The residue was purified by flash chromatography (50% EtOAc in petroleum ether) to obtain 16 in 75% purity. After crystallization from EtOAc and petroleum ether, the title intermediate 16 was obtained as a white solid (160 mg, 43.42%)

m/z=506 (M+H)$^+$.

$^1$HNMR (CDCl$_3$ 400 MHz) δ ppm 1.72-1.84 (m, 4H) 2.03 (m, 1H) 2.38-2.50 (m, 3H) 3.47-3.52 (m, 3H) 3.61-3.68 (m, 2H) 3.84-3.93 (m, 4H) 4.12-4.15 (t, J=7.4 Hz, 4H) 4.41-4.45 (d, J=12.80 Hz, 1H) 5.11 (s, 1H) 5.96 (br.s, 1H) 6.15 (s, 1H) 7.29-7.33 (m, 1H) 7.66-7.70 (m, 1H) 7.78-7.80 (d, J=8.5 Hz, 1H) 7.98-8.00 (d, J=8.3 Hz, 1H).

Step 2: synthesis of N-(4-(2-(5-(azetidin-1-yl)-7-morpholinopyrazolo[1,5-a]pyrimidin-2-yl)piperidin-1-yl)quinazolin-2-yl)methanesulfonamide P10

A mixture of intermediate 16 (60 mg, 119 umol, 1 eq.), methanesulfonamide (34 mg, 357 umol, 3 eq.), 4,5-bis (diphenylphosphino)-9,9-dimethylxanthene (14 mg, 0.2 eq.), palladium(II) acetate (5.3 mg, 0.2 eq.) and Cesium carbonate (116 mg, 357 umol, 3 eq.) in 1,4-dioxane (5 mL) was stirred at 110° C. for 18 h under N$_2$. The reaction mixture was diluted with water and extracted with EtOAc (3×20 mL). The combined organic layers were concentrated. The residue was purified by HPLC, and the fractions were lyophilized. The solid was treated with SAX-SPE to obtain compound P10 as a yellow solid (24 mg, 34%)

m/z=564 (M+H)$^+$.

$^1$HNMR (400 MHz, CD$_3$OD): δ ppm 1.89 (br, 4H) 2.22 (m, 1H) 2.58 (m, 3H) 3.08 (s, 3H) 3.59 (br, 1H) 3.89 (d, 4H) 3.91 (m, 4H) 4.38 (t, J=7.5 Hz, 4H) 4.62 (br, 1H) 5.27 (s, 1H) 6.29 (s, 1H) 6.33 (br, 1H) 7.39 (t, J=7.3 Hz, 1H) 7.49 (d, J=8.5 Hz, 1H) 7.79 (t, J=7.3 Hz, 1H) 8.01 (d, J=8 Hz, 1H).

Synthesis of 4-(2-(5-(azetidin-1-yl)-6-methylpyrazolo[1,5-a]pyrimidin-2-yl)-piperidin-1-yl)-6-methylquinazoline P11

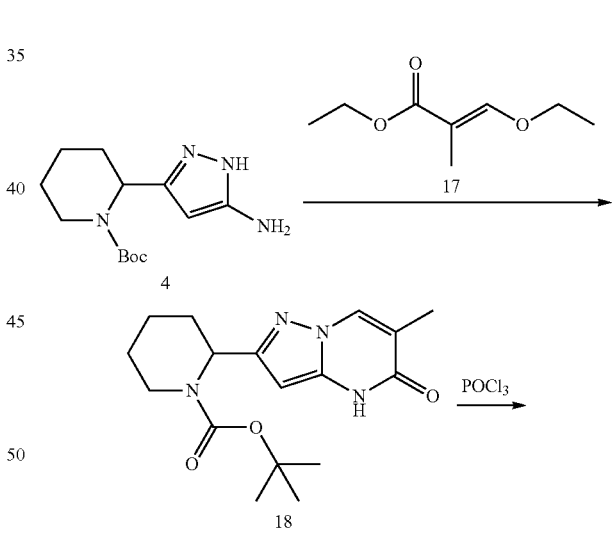

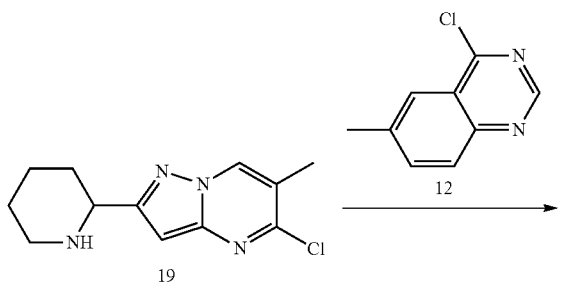

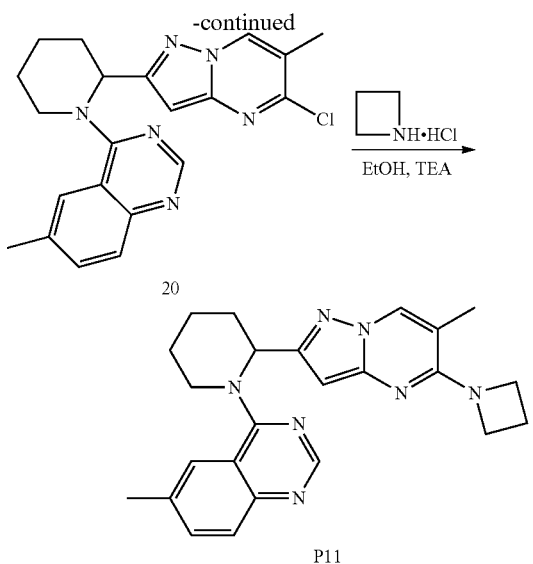

Step 1: synthesis of tert-butyl 2-(6-methyl-5-oxo-4,5-dihydropyrazolo[1,5-a]-pyrimidin-2-yl)piperidine-1-carboxylate 18

The intermediate 4 (5.00 g, 18.08 mmol) was dissolved in dry DMF (112 ml), then $Cs_2CO_3$ (9.00 g, 27.62 mmol) and (E)-ethyl 3-ethoxy-2-methylacrylate 17 (4.30 g, 27.18 mmol) were added and the mixture was heated at 130° C. for 3 days. DMF was evaporated and the dark brown oil was poured into iced water. After warming to room temperature, the product was extracted with EtOAc (3 times). The organic layers were dried over $Na_2SO_4$, filtered and evaporated and the resulting residue was purified by column chromatography eluting with a gradient starting from 0% to 10% MeOH and dichloromethane. After evaporation of the concerning fractions, we obtain intermediate 18 as a yellow solid (1100 mg, 18%).

$^1$H NMR (400 MHz, $CDCl_3$) δ ppm 1.35-1.71 (m, 13H) 1.73-1.88 (m, 1H) 2.09 (d, J=1.10 Hz, 3H) 2.32 (d, J=13.64 Hz, 1H) 2.70-2.92 (m, 1H) 3.93-4.13 (m, 1H) 5.35-5.54 (m, 1H) 5.71 (s, 1H) 7.99 (s, 1H) 10.56-10.76 (m, 1H)

m/z=333.20 (M+H)$^+$

Step 2: synthesis of 5-chloro-6-methyl-2-(piperidin-2-yl)pyrazolo[1,5-a]pyrimidine 19

$POCl_3$ (6.15 ml, 66.19 mmol) was added to intermediate 18 (1100 mg, 3.31 mmol) at room temperature, then the mixture was heated at 100° C. for 1.5 hours. The reaction mixture was cooled to room temperature and $POCl_3$ was evaporated. The residue was co-evaporated 3 times with toluene to get brown foam intermediate 19 which was used as such in the next step.

m/z=250.96 (M+H)$^+$

Step 3: synthesis of 4-(6-methyl-2-(1-(6-methylquinazolin-4-yl)piperidin-2-yl)-pyrazolo[1,5-a]pyrimidin-5-yl)morpholine 20

The crude intermediate 19 (150 mg, 0.30 mmol) and 4-chloro-6-methylquinazoline 12 (107 mg, 0.60 mmol) were dissolved in 2-methoxyethanol (3.79 ml) and then di-isopropylethyl amine (619 μl, 3.59 mmol) was added. The solution was heated at 100° C. overnight. The heating was stopped and the mixture was cooled to room temperature. To the reaction mixture was added morpholine (1.035 ml, 11.97 mmol) and the mixture was heated at 70° C. for 3 hours. Then it was evaporated to dryness. The resulting residue was purified by column chromatography eluting with 2.5% (MeOH/$NH_3$) and dichloromethane. The oil obtained was recrystallized in di-isopropyl ether. The formed off-white crystals were filtered to get intermediate 20 (52 mg, 38%).

m/z=444.25 (M+H)$^+$

MP=180.64° C.

$^1$H NMR (400 MHz, DMSO-$d_6$) δ ppm 1.57-1.80 (m, 4H) 1.92-2.08 (m, 1H) 2.24 (s, 3H) 2.34-2.46 (m, 4H) 3.20-3.28 (m, 4H) 3.45 (br. t, J=11.20, 11.20 Hz, 1H) 3.67-3.83 (m, 4H) 4.21 (br. d, J=13.90 Hz, 1H) 5.85 (br. s., 1H) 6.20 (s, 1H) 7.64 (br. d, J=8.40 Hz, 1H) 7.71 (d, J=8.58 Hz, 1H) 7.83 (br. s, 1H) 8.56 (s, 1H) 8.71 (s, 1H)

Step 4: synthesis of 4-(2-(5-(azetidin-1-yl)-6-methylpyrazolo[1,5-a]pyrimidin-2-yl)-piperidin-1-yl)-6-methylquinazoline P11

A solution of intermediate 20 (145 mg, 0.37 mmol), azetidine hydrochloride (69 mg, 0.74 mmol) and di-isopropylethyl ether (191 μl, 1.11 mmol) in EtOH (10 ml) was heated at 65° C. for 3.5 hours. All solvent was evaporated and the yellow wet solid was refluxed in acetonitril. The remaining insoluble solid was filtered off hot and the filtrate was cooled to room temperature. The mixture was stirred overnight. The crystals were filtered off and washed with acetonitril. The product was again recrystallized in MeOH and acetonitril. The white crystals were filtered and washed with acetonitril to get the title product P11 (72 mg, 47%).

m/z=414.12 (M+H)$^+$

MP=205.49° C.

$^1$H NMR (400 MHz, DMSO-$d_6$) δ ppm 1.58-1.79 (m, 4H) 1.88-2.03 (m, 1H) 2.15 (d, J=0.88 Hz, 3H) 2.27 (quin, J=7.59 Hz, 2H) 2.32-2.40 (m, 1H) 2.42 (s, 3H) 3.37-3.49 (m, 1H) 4.15-4.28 (m, 5H) 5.77-5.84 (m, 1H) 5.96 (s, 1H) 7.63 (dd, J=8.58, 1.76 Hz, 1H) 7.71 (d, J=8.58 Hz, 1H) 7.82 (br. s, 1H) 8.40-8.45 (m, 1H) 8.56 (s, 1H)

Synthesis of 1-(6-methyl-2-(1-(6-methylquinazolin-4-yl)piperidin-2-yl)pyrazolo-[1,5-a]pyrimidin-5-yl)azetidin-3-ol P12

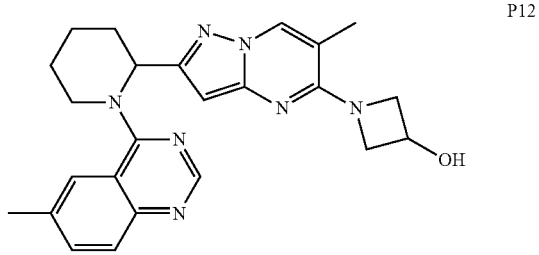 [SMILES: Cc1ccc2ncnc(N3CCCCC3c3cc4nc(N5CC(O)C5)c(C)cn4n3)c2c1]

P12

Compound P12 was prepared in the same manner as compound P11 using intermediate 20 and azetidin-3-ol as starting materials.

m/z=430.12 (M+H)$^+$

MP=233.08° C.

$^1$H NMR (400 MHz, DMSO-$d_6$) δ ppm 1.53-1.80 (m, 4H) 1.87-2.03 (m, 1H) 2.14 (s, 3H) 2.31-2.40 (m, 1H) 2.42 (s, 3H) 3.38-3.50 (m, 1H) 3.93 (dd, J=9.13, 4.73 Hz, 2H)

4.16-4.28 (m, 1H) 4.32-4.44 (m, 2H) 4.46-4.59 (m, 1H) 5.61-5.71 (m, 1H) 5.76-5.84 (m, 1H) 5.98 (s, 1H) 7.58-7.67 (m, 1H) 7.67-7.75 (m, 1H) 7.83 (br. s, 1H) 8.45 (br. s, 1H) 8.56 (s, 1H)

Synthesis of 1-(6-methyl-2-(1-(6-methylquinazolin-4-yl)piperidin-2-yl)pyrazolo-[1,5-a]pyrimidin-5-yl)azetidin-3-amine P13

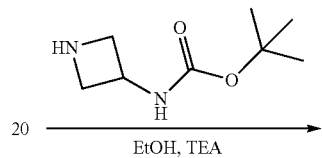

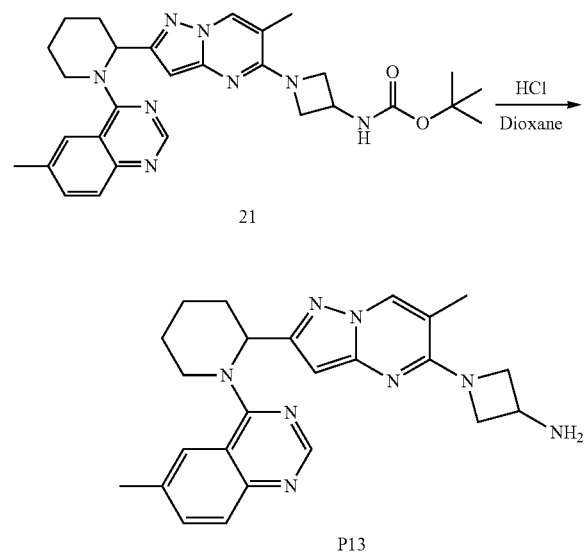

Step 1: synthesis of tert-butyl 1-(6-methyl-2-(1-(6-methylquinazolin-4-yl)piperidin-2-yl)pyrazolo[1,5-a]pyrimidin-5-yl)azetidin-3-ylcarbamate 21

Intermediate 21 was prepared in the same manner as compound P11 using intermediate 20 and tert-butylazetidin-3-ylcarbamate as starting materials.

m/z=529.25 (M+H)$^+$ $^1$H NMR (400 MHz, DMSO-d$_6$) δ ppm 1.40 (s, 9H) 1.67-1.89 (m, 4H) 1.98-2.11 (m, 1H) 2.15 (d, J=0.88 Hz, 3H) 2.41-2.46 (m, 4H) 3.60-3.74 (m, 1H) 4.02-4.11 (m, 2H) 4.27-4.37 (m, 1H) 4.37-4.46 (m, 2H) 4.61-4.75 (m, 1H) 6.12 (s, 1H) 6.22-6.35 (m, 1H) 7.10-7.30 (m, 1H) 7.80-7.88 (m, 2H) 7.97 (br. s, 1H) 8.37 (s, 1H) 8.74 (s, 1H)

Step 2: synthesis of 1-(6-methyl-2-(1-(6-methylquinazolin-4-yl)piperidin-2-yl)-pyrazolo[1,5-a]pyrimidin-5-yl)azetidin-3-amine P13

A solution of intermediate 21 (215 mg, 0.39 mmol) and a 4M solution of HCl in dioxane (6 ml, 24 mmol) were stirred at room temperature for 2 hours. Dioxane was evaporated and the crude was purified by column chromatography eluting with a gradient starting from 0.5% to 10% (MeOH/NH$_3$) and dichloromethane. After evaporation of the solvent we obtain the title compound P13 as a white solid (18 mg, 10%).

m/z=429.20 (M+H)$^+$ $^1$H NMR (400 MHz, DMSO-d$_6$) δ ppm 1.57-1.75 (m, 4H) 1.88-2.03 (m, 1H) 2.11-2.20 (m, 3H) 2.31-2.40 (m, 1H) 2.42 (s, 3H) 3.37-3.49 (m, 1H) 3.70-3.89 (m, 3H) 4.16-4.27 (m, 1H) 4.29-4.39 (m, 2H) 5.76-5.84 (m, 1H) 5.96 (s, 1H) 7.63 (dd, J=8.58, 1.76 Hz, 1H) 7.71 (d, J=8.36 Hz, 1H) 7.82 (br. s, 1H) 8.42-8.46 (m, 1H) 8.55 (s, 1H).

Synthesis of 2-methoxyethyl 4-(2-(5-(azetidin-1-yl)-7-morpholinopyrazolo[1,5-a]-pyrimidin-2-yl)piperidin-1-yl)-6-morpholinoquinazolin-2-ylcarbamate P14

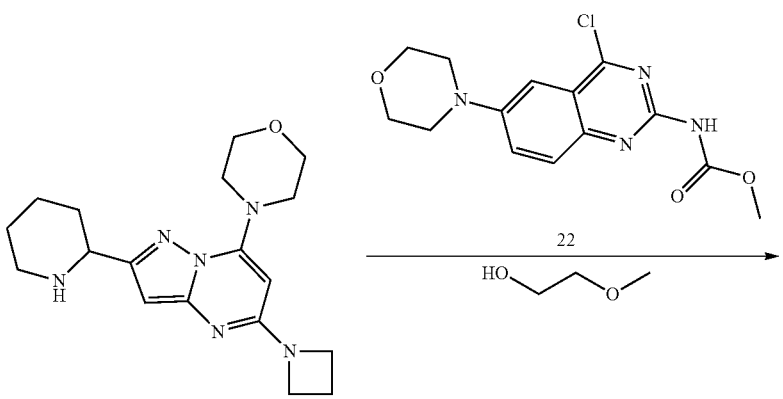

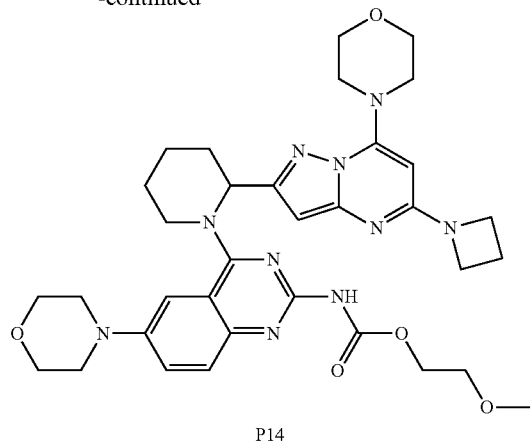

P14

Synthesis of methyl (4-chloro-6-morpholinoquinazolin-2-yl)carbamate 22

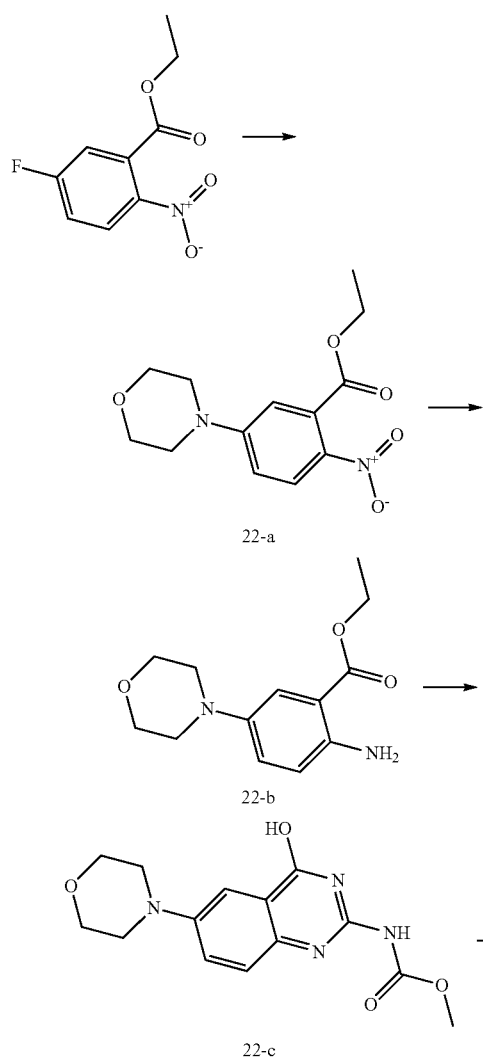

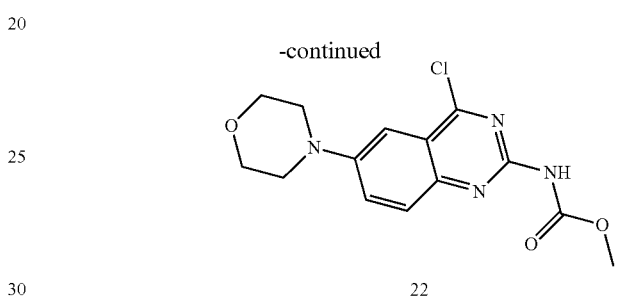

22

Step 1: synthesis of ethyl 5-morpholino-2-nitrobenzoate 22-a

Ethyl 5-fluoro-2-nitrobenzoate (5 g, 23.46 mmol) was dissolved in DMF (150 ml) and then morpholine (6.13 g, 70.37 mmol) was added. The reaction mixture was stirred 4 hours at room temperature. The solvent was removed under reduced pressure and the crude was re-dissolved in dichloromethane, washed with 1M HCl-solution, dried over $MgSO_4$, filtered and evaporated to dryness to yield intermediate 22-a.

Step 2: synthesis of ethyl 2-amino-5-morpholinobenzoate 22-b

Ethyl 5-morpholino-2-nitrobenzoate 22-a (6.574 g, 23.46 mmol) was dissolved in a mixture of EtOH (150 ml) and THF (250 ml), then Pd/C (10%) (2.496 g, 2.35 mmol) was added and the reaction mixture was set under a hydrogen atmosphere for 2 hours. The reaction mixture was filtered over dicalite and the filtrate was evaporated to dryness yielding the wanted intermediate 22-b as a brown solid (6.24 g, quantitative).

Step 3: synthesis of methyl 4-hydroxy-6-morpholinoquinazolin-2-ylcarbamate 22-c Ethyl 2-amino-5-morpholinobenzoate 22-b (6.24 g, 24.93 mmol), 1,3-bis(methoxy-carbonyl)-2-methyl-2-thio-pseudourea (5.91 g, 28.67 mmol) and acetic acid (7.14 ml, 124.65 mmol) were dissolved in 100 ml MeOH and stirred overnight at 75° C. Extra acetic acid (1 ml, 17.47 mmol) was added and the reaction mixture was stirred at 75° C. for 7 days. The pH was set to 5 with acetic acid. The volatiles were evaporated to dryness. Then the residue was re-dissolved in 15 ml MeOH and 100 ml water was added. The precipitate was filtered off, washed with diethylether to yield the title intermediate 22-c as a brown solid (5.28 g, 70%).

Step 4: synthesis of methyl 4-chloro-6-morpholinoquinazolin-2-ylcarbamate 22

Methyl (4-hydroxy-6-morpholinoquinazolin-2-yl)carbamate 22-c (1.00 g, 3.29 mmol) was suspended in dry acetonitril (12.38 ml), then POCl₃ (1.15 ml, 12.4 mmol) was added at room temperature and the mixture was refluxed for 4.5 hours. After cooling to room temperature, the reaction mixture was evaporated to dryness. The residue was co-evaporated with toluene. The crude was dissolved in DCM and it was washed with saturated sodium hydrogencarbonate solution in water. The organic layer was dried over Na₂SO₄, filtered and evaporated. The residue was triturated in di-isopropylether. The solid was filtered off to get the title intermediate 22 as a dark brown solid.
m/z=323.15 (M+H)⁺

Step 5: synthesis of 2-methoxyethyl 4-(2-(5-(azetidin-1-yl)-7-morpholinopyrazolo-[1,5-a]pyrimidin-2-yl)piperidin-1-yl)-6-morpholinoquinazolin-2-ylcarbamate P14

A solution of intermediate 8 (80 mg, 0.23 mmol), methyl (4-chloro-6-morpholino-quinazolin-2-yl)carbamate 22 (152 mg, 0.23 mmol) and diisopropyl ethyl amine (117 μl, 0.68 mmol) in 2-methoxyethanol (1.79 ml) was heated at 100° C. overnight. The solvents were evaporated and the residue was purified by column chromatography eluting with a gradient starting from 0.5% to 10% MeOH in DCM. After evaporation of the solvent we obtain an oil that was triturated in di-isopropyl ether and the suspension was sonicated for 5 minutes. The solid was filtered and washed with some di-isopropyl ether to get the title compound P14 as a brown powder (38 mg, 24%).
m/z=673.34 (M+H)⁺
¹H NMR (400 MHz, DMSO-d₆) δ ppm 1.58-1.80 (m, 4H) 1.93-2.06 (m, 1H) 2.24-2.40 (m, 3H) 2.95-3.11 (m, 4H) 3.28 (s, 3H) 3.30-3.34 (m, 1H) 3.42-3.59 (m, 6H) 3.64-3.75 (m, 8H) 4.01 (t, J=7.37 Hz, 4H) 4.14-4.22 (m, 2H) 4.22-4.32 (m, 1H) 5.33 (s, 1H) 5.70-5.81 (m, 1H) 6.00 (s, 1H) 7.17 (d, J=2.20 Hz, 1H) 7.51 (d, J=9.24 Hz, 1H) 7.56 (dd, J=9.68, 2.64 Hz, 1H) 9.83 (br. s., 1H)

Synthesis of 4-(5-(azetidin-1-yl)-2-(1-(2-methyl-7H-pyrrolo[2,3-d]pyrimidin-4-yl)-piperidin-2-yl)pyrazolo[1,5-a]pyrimidin-7-yl)morpholine P15

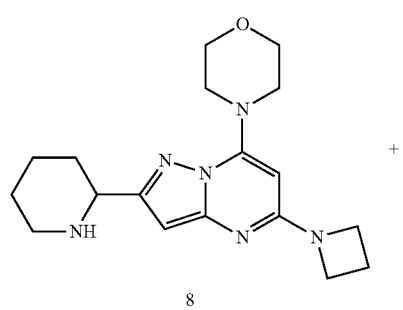

8

+

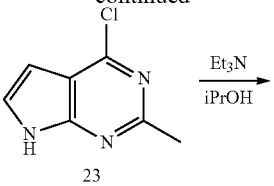

23

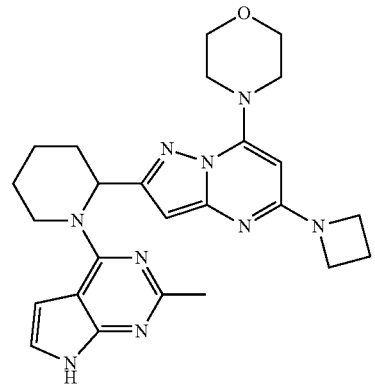

P15

Synthesis of 4-chloro-2-methyl-7H-pyrrolo[2,3-d]pyrimidine 23

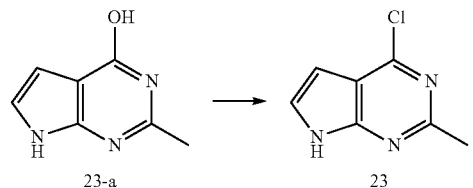

23-a     23

2-Methyl-3H-pyrrolo[2,3-d]pyrimidin-4(7H)-one 23-a (10.54 g, 70.6 mmol) was dissolved in Toluene (20 mL) under inert atmosphere. DIPEA (24 mL, 141 mmol, 2 eq.) and POCl₃ (19.5 mL, 212 mmol, 3 eq.) were added dropwise at 70° C. and the mixture was then heated to 106° C. After 16 hours, the solution was concentrated in vacuo, extracted with ethyl acetate and washed with saturated NaHCO₃ solution. The combined organic layers were dried over Na₂SO₄, and concentrated in vacuo to yield a grey oil which was suspended in water/heptanes to afford a white solid intermediate 23 (5.9 g, 50%).

Synthesis of 4-(5-(azetidin-1-yl)-2-(1-(2-methyl-7H-pyrrolo[2,3-d]pyrimidin-4-yl)-piperidin-2-yl)pyrazolo[1,5-a]pyrimidin-7-yl)morpholine P15

To a solution of intermediate 8 (100 mg, 0.28 mmol) in isopropanol (3 mL) was added intermediate 23 (47 mg, 0.28 mmol, 1 eq.) and Et₃N (0.118 mL, 0.84 mmol, 3 eq.) in a sealed pressure tube. The solution was heated to 140° C. and stirred during 16 hours. After cooling to room temperature, the solution was concentrated in vacuum and purified by Prep HPLC to yield the title compound P15 (36 mg, 27%).
m/z=474 (M+H)⁺
¹H NMR (600 MHz, DMSO-d₆) δ ppm 1.52-1.58 (m, 1H) 1.58-1.69 (m, 2H) 1.73 (d, J=11.74 Hz, 1H) 1.91 (br. s., 1H) 2.24-2.32 (m, 2H) 2.32-2.38 (m, 1H) 2.36 (s, 3H) 3.27 (t, J=12.03 Hz, 1H) 3.47 (br. s., 4H) 3.58-3.68 (m, 4H) 3.97 (t, J=7.34 Hz, 4H) 4.61 (d, J=11.74 Hz, 1H) 5.23 (s, 1H) 5.71 (s, 1H) 6.21 (br. s., 1H) 6.42 (br. s., 1H) 6.98 (br. s., 1H) 11.17 (br. s., 1H)

Synthesis of 4-(5-(azetidin-1-yl)-2-(1-(2-ethoxy-pyrido[2,3-d]pyrimidin-4-yl)-piperidin-2-yl)pyrazolo[1,5-a]pyrimidin-7-yl)morpholine P16

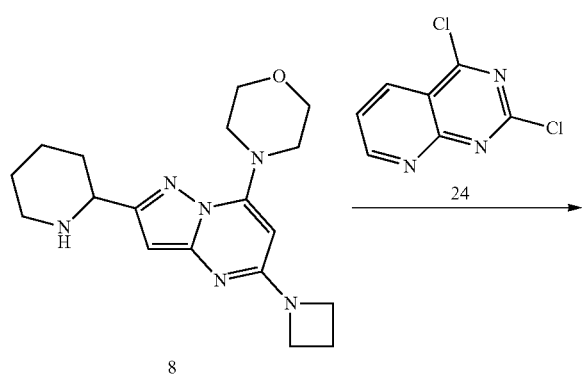

product was purified by column chromatography over silica gel (eluent: methanol/ethyl acetate 1/10). The resulting residue was lyophilized to yield a white solid (78.3 mg, 27%).

Step 2: synthesis of 4-(5-(azetidin-1-yl)-2-(1-(2-ethoxypyrido[2,3-d]pyrimidin-4-yl)-piperidin-2-yl)pyrazolo[1,5-a]pyrimidin-7-yl)morpholine P16

To a solution of intermediate 25 (67 mg, 0.13 mmol) in EtOH (10 mL) was added 100 µL HCl.iPrOH (6N) and the solution was heated to 40° C. during 16 hours. The resulting solution was concentrated in vacuum and purified by column chromatography eluting with a gradient starting from 0% to 10% MeOH in DCM. After evaporation the title compound P16 (20 mg, 25%) was obtained.

m/z=516 (M+H)+

1H NMR (400 MHz, DMSO-d6) δ ppm 1.33 (t, J=7.04 Hz, 3H) 1.71 (br. s., 4H) 1.92-2.11 (m, 1H) 2.23-2.39 (m, 3H) 3.40-3.58 (m, 5H) 3.61-3.74 (m, 4H) 4.01 (t, J=7.37 Hz, 4H) 4.20 (br. d, J=13.90 Hz, 1H) 4.40 (q, J=7.00 Hz, 2H) 5.28 (s, 1H) 5.79-5.88 (m, 1H) 5.91 (s, 1H) 7.19 (dd, J=8.58, 4.40 Hz, 1H) 8.38 (dd, J=8.14, 1.54 Hz, 1H) 8.76-8.82 (m, 1H)

Synthesis of 4-(5-(azetidin-1-yl)-2-(1-(5-methylquinazolin-4-yl)piperidin-2-yl)-pyrazolo[1,5-a]pyrimidin-7-yl)morpholine P17

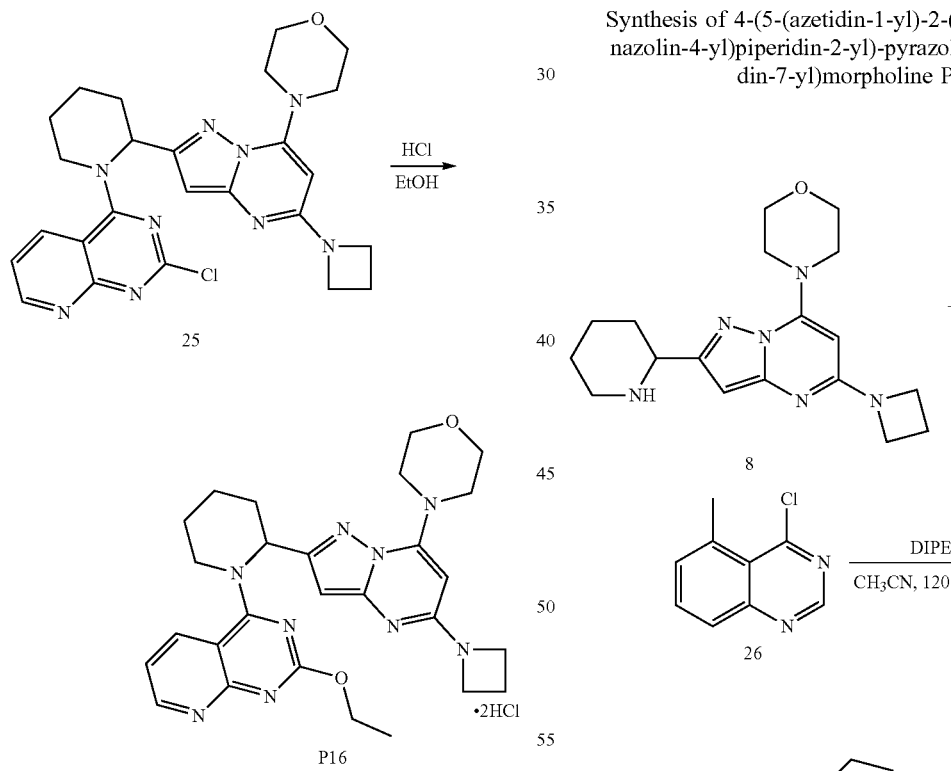

Step 1: synthesis of 4-(5-(azetidin-1-yl)-2-(1-(2-chloropyrido[2,3-d]pyrimidin-4-yl)-piperidin-2-yl)pyrazolo[1,5-a]pyrimidin-7-yl)morpholine 25

Intermediate 8 (200 mg, 0.584 mmol) was dissolved in ethanol (10 mL), then 2,4-dichloropyrido[2,3-d]pyrimidine 24 (117 mg, 0.58 mmol) and triethylamine (177 mg, 1.75 mmol) were added. The resulting mixture was stirred at 90° C. for 12 hours. The solvent was evaporated. This crude

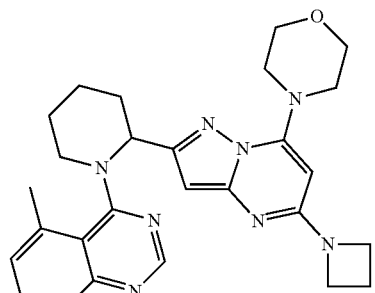

Synthesis of 4-chloro-5-methylquinazoline 26

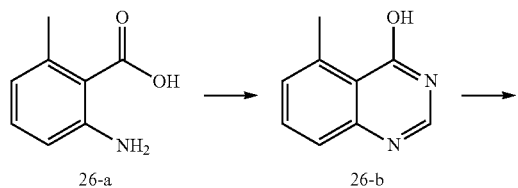

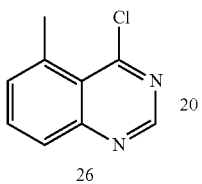

Step 1: synthesis of 5-methylquinazolin-4-ol 26-b

2-Amino-6-methylbenzoic acid 26-a (4 g, 26 mmol) was dissolved in 10 mL formamide and the solution was heated to 120° C. After 4 hours water was added and the solid filtered off. The solid was further washed with water and dried into the oven yielding intermediate 26-b (3.25 g, 77%).

m/z=160 (M+H)$^+$ $^1$H NMR (400 MHz, DMSO-d$_6$) δ ppm 2.77 (s, 3H) 7.25 (d, J=7.48 Hz, 1H) 7.46 (d, J=7.70 Hz, 1H) 7.62 (t, J=7.90 Hz, 1H) 7.98 (s, 1H) 11.89 (br. s, 1H)

Step 2: synthesis of 4-chloro-5-methylquinazoline 26

Into a solution of intermediate 26-b (100 mg, 0.62 mmol) in acetonitrile (2 mL) was added DIPEA (0.23 mL, 1.88 mmol, 3 eq.). The resulting solution was heated to 70° C. and stirred for 10 minutes. POCl$_3$ was then added to the solution dropwise. After 16 hours, the solution was concentrated in vacuo to yield intermediate 26.

Synthesis of 4-(5-(azetidin-1-yl)-2-(1-(5-methylquinazolin-4-yl)piperidin-2-yl)-pyrazolo[1,5-a]pyrimidin-7-yl)morpholine P17

To a solution of intermediate 8 (230 mg, 0.67 mmol) in CH$_3$CN (10 mL) in a sealed tube was added DIPEA (2.3 mL, 13.4 mmol, 20 eq.) and 4-chloro-5-methylquinazoline 26 (120 mg, 0.67 mmol, 1 eq.). The solution was heated at 120° C. and stirred during 16 hours. After cooling to room temperature, the solution was concentrated in vacuum and the crude purified by Prep HPLC to yield compound P17 (28 mg, 9%).

m/z=485 (M+H)$^+$ $^1$H NMR (600 MHz, DMSO-d$_6$) δ ppm 1.54-1.86 (m, 4H) 2.08-2.13 (m, 2H) 2.28-2.33 (m, 2H) 2.86 (s, 3H) 3.28-3.31 (m, 2H) 3.39-3.44 (m, 2H) 3.49-3.54 (m, 2H) 3.62-3.69 (m, 4H) 4.00 (t, J=7.41 Hz, 4H) 5.31 (s, 1H) 5.75 (t, J=4.40 Hz, 1H) 5.97 (s, 1H) 7.37 (d, J=6.90 Hz, 1H) 7.60-7.63 (m, 1H) 7.67-7.71 (m, 1H) 8.53 (s, 1H)

Synthesis of (R)-4-(5-(azetidin-1-yl)-2-(1-(5-methylquinazolin-4-yl)piperidin-2-yl)-pyrazolo[1,5-a]pyrimidin-7-yl)morpholine P18 and (S)-4-(5-(azetidin-1-yl)-2-(1-(5-methylquinazolin-4-yl)piperidin-2-yl)pyrazolo[1,5-a]pyrimidin-7-yl)morpholine P19

A purification was performed via Prep SFC (Stationary phase: Chiralpak Diacel AS 20×250 mm, Mobile phase: CO2, EtOH with 0.2% iPrNH2) giving both relative enantiomers:

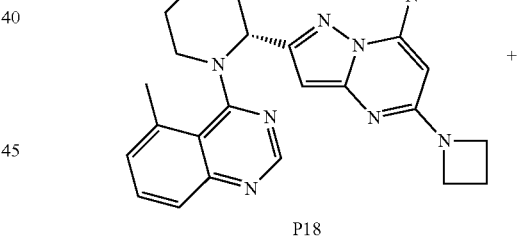

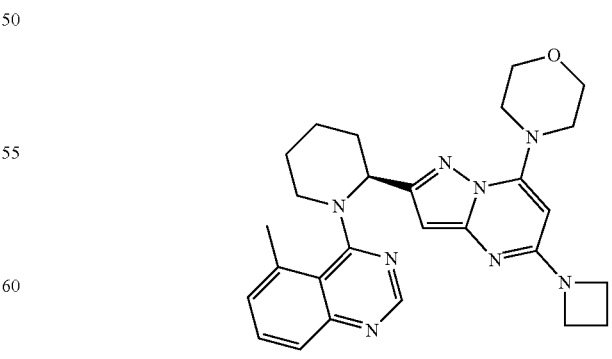

P18: [α]$_D^{20}$=+210.64° (589 nm, c=0.3855 w/v %, DMF, 20° C.)

Synthesis of 4-(5-(azetidin-1-yl)-2-(1-(2-methylthiazolo[5,4-d]pyrimidin-7-yl)-piperidin-2-yl)pyrazolo[1,5-a]pyrimidin-7-yl)morpholine P20

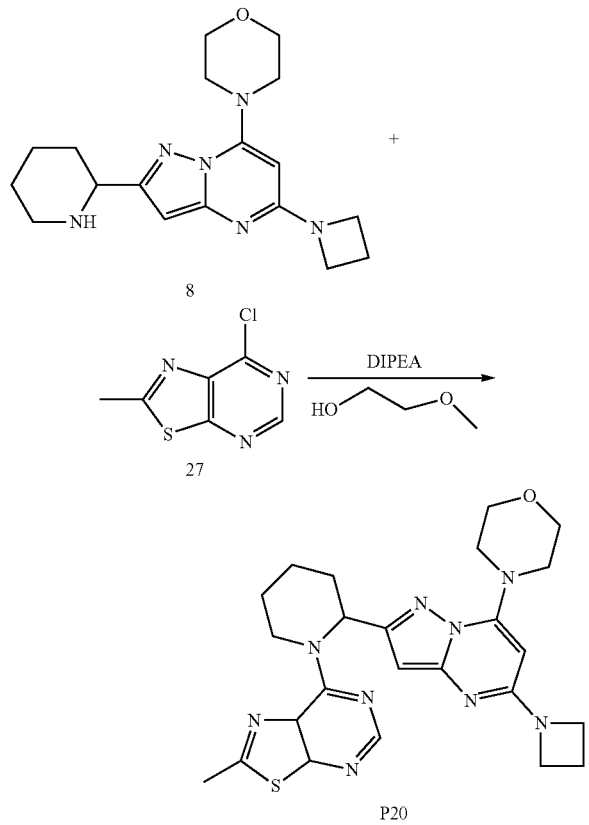

Synthesis of 7-chloro-2-methylthiazolo[5,4-d]pyrimidine 27

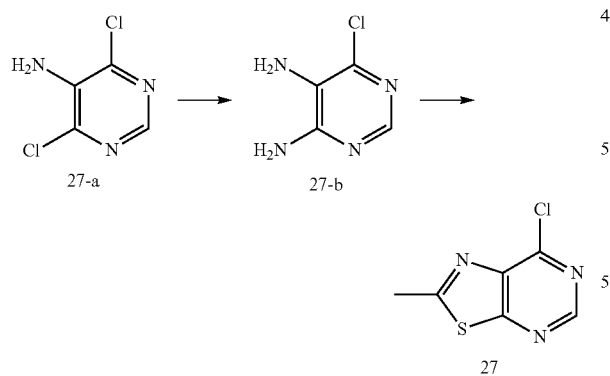

Step 1: synthesis of 5-amino-6-chloropyrimidine-4-thiol 27-b

To a solution of sulfanylsodium hydrate (2.48 g, 33.54 mmol) in water (6 mL) was added MeOH (50 mL) and 4,6-dichloropyrimidin-5-amine 27-a (5 g, 30.49 mmol). The resulting mixture was stirred at reflux for one hour and at ambient temperature overnight. The mixture was evaporated and the residue was dried in vacuo, to yield intermediate 27-b (3.63 g, 74%).
m/z=161 (M+H)$^+$

Step 2: synthesis of 7-chloro-2-methylthiazolo[5,4-d]pyrimidine 27

A solution of 5-amino-6-chloro-pyrimidine-4-thiol 27-b (4.7 g, 29.1 mmol) in triethylorthoacetate (150 mL) was stirred at 150° C. for one hour. The reaction mixture was allowed to cool to room temperature and was then evaporated to dryness. The residue was triturated in diisopropylether with some acetonitrile. The precipitate was collected by filtration and dried in vacuo to yield intermediate 27 (0.9 g, 4.85 mmol)

Synthesis of 4-(5-(azetidin-1-yl)-2-(1-(2-methylthiazolo[5,4-d]pyrimidin-7-yl)-piperidin-2-yl)pyrazolo[1,5-a]pyrimidin-7-yl)morpholine P20

A solution of intermediate 8 (378.9 mg, 1 mmol), 7-chloro-2-methyl-thiazolo[5,4-d]-pyrimidine 27 (185.6 mg, 1 mmol), Hunig's base (0.7 mL, 4.22 mmol) and 2-methoxyethanol (10 mL) was stirred at 100° C. overnight. The mixture was evaporated and the residue was dissolved in dichloromethane and washed twice with water. The organic layer was dried over MgSO4, filtered and evaporated. The residue was purified over silica with dichloromethane/methanol 100/0 to 95/5 as gradient. The corresponding fractions were evaporated. The residue was crystallised in diisopropylether and 10% acetonitrile. The white crystals were collected by filtration and dried in vacuo to yield compound P20 (163 mg, 33%).
m/z=491.62 (M+H)$^+$
mp: 229.8° C.
$^1$H NMR (400 MHz, DMSO-d$_6$) δ ppm 1.48-1.83 (m, 2H), 1.91-2.06 (m, 1H), 2.29 (quin, J=7.5 Hz, 1H), 2.39 (d, J=13.7 Hz, 1H), 2.72 (s, 3H), 3.21 (m, J=2.4 Hz, 1H), 3.42-3.54 (m, 4H), 3.56-3.70 (m, 4H), 3.98 (t, J=7.5 Hz, 4H), 5.16-5.30 (m, 2H), 5.73 (s, 1H), 6.98 (br. s., 1H), 8.32 (s, 1H)

Synthesis of 4-(2-(5-(azetidin-1-yl)-7-methylpyrazolo[1,5-a]pyrimidin-2-yl)-piperidin-1-yl)-6-methylquinazoline P21

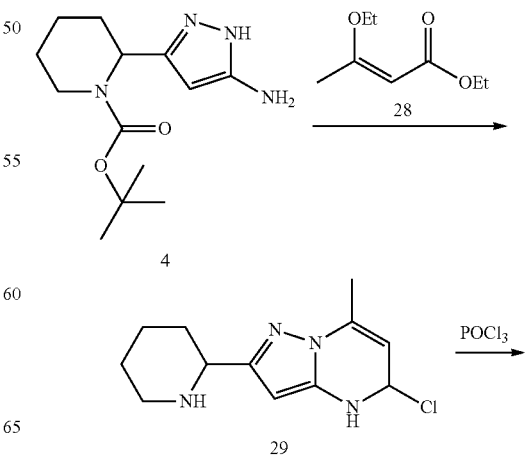

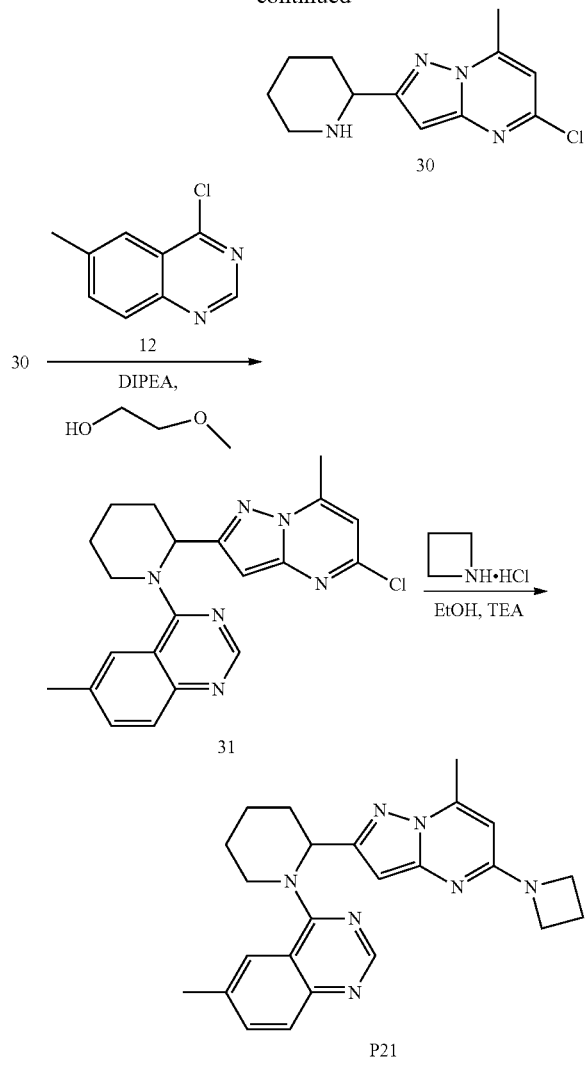

Step 1: synthesis of 7-methyl-2-(piperidin-2-yl) pyrazolo[1,5-a]pyrimidin-5(4H)-one 29

The commercially available (Z)-ethyl 3-ethoxybut-2-enoate 28 (33 g, 208.60 mmol) and Cs$_2$CO$_3$ (54 g, 165.74 mmol) were added to a solution of intermediate 4 (30 g, 112.64 mmol) in DMF (180 ml). The mixture was stirred at 110° C. for 12 hours. The precipitate was filtered off and washed with ethyl acetate (100 ml). The filtrate was concentrated under vacuum. The residue was dissolved in ethyl acetate (300 ml) and washed with brine (2×100 ml). The organic layer was dried (MgSO$_4$), filtered and the filtrate was concentrated under vacuum. The residue was washed with isopropyl ether (200 ml) and then dried (vacuum, 45° C., 1 hour) to yield intermediate 29 (25 g, 65.37%).

m/z=233 (M+H)$^+$

Step 2: synthesis of 5-chloro-7-methyl-2-(piperidin-2-yl)pyrazolo[1,5-a]pyrimidine 30

A mixture of intermediate 29 (22.5 g, 67.69 mmol) in POCl$_3$ (377.5 g) was stirred at 100° C. for 2 hours. The solvent was evaporated under vacuum. Acetonitrile (200 ml) was added. The mixture was neutralized with NH$_3$ (7 M in methanol) to pH=8. The solvent was evaporated under vacuum. The residue was purified by column chromatography over silica gel (eluent: dichloromethane/methanol 10/1) to yield intermediate 30 (13.97 g, 80.47%).

m/z=251 (M+H)$^+$ $^1$H NMR (400 MHz, DMSO-d$_6$) δ ppm 1.52-1.73 (m, 4H) 1.76-1.86 (m, 1H) 1.99-2.02 (m, 1H) 2.70 (s, 3H) 2.83-2.88 (m, 1H) 3.15-3.18 (d, J=12.0 Hz, 1H) 4.14-4.17 (dd, J1=10.8, J2=2.8 Hz, 1H) 6.81 (s, 1H) 7.14 (s, 1H)

Step 3: synthesis of 4-(2-(5-chloro-7-methylpyrazolo[1,5-a]pyrimidin-2-yl)piperidin-1-yl)-6-methylquinazoline 31

A solution of intermediate 30 (501.5 mg, 2 mmol) and 4-chloro-6-methyl-quinazoline 12 (535.9 mg, 3 mmol) in methoxyethanol (5 mL) was stirred at 120° C. overnight. The mixture was evaporated and the residue was dissolved in dichloromethane, washed twice with water, dried over MgSO4, filtered and evaporated. The residue was purified over silica with dichloromethane/methanol-NH3 98/2. The corresponding fractions were evaporated and the residue was crystallized in di-isopropylether with 10% acetonitrile. The greenish precipitate was filtered off and dried in vacuum to yield intermediate 31 (645 mg, 82%)

m/z=392.9 (M+H)$^+$ mp: 154.2° C.

$^1$H NMR (400 MHz, DMSO-d$_6$) δ ppm 1.62-1.81 (m, 2H), 2.45 (s, 3H), 2.69 (s, 2H), 4.16 (br. s., 1H), 5.95 (br. s., 1H), 6.60 (s, 1H), 7.00 (s, 1H), 7.63 (d, J=1.6 Hz, 1H), 7.66-7.79 (m, 1H), 7.86 (s, 1H), 8.55 (s, 1H)

Synthesis of 4-(2-(5-(azetidin-1-yl)-7-methylpyrazolo[1,5-a]pyrimidin-2-yl)-piperidin-1-yl)-6-methylquinazoline P21

A solution of intermediate 31 (196.45 mg, 0.5 mmol), azetidine hydrochloride (93.56 mg, 1 mmol), Hunig's base (0.26 mL, 1.5 mmol) and ethanol (5 mL) was stirred at 60° C., over weekend. The mixture was evaporated and the residue was triturated in water and stirred for one hour. The precipitate was filtered off and recrystallized in acetonitrile. The white crystals were collected by filtration and dried in vacuo to yield compound P21 (175 mg, 84%)

m/z=413.5 (M+H)$^+$ mp: 192.43° C.

$^1$H NMR (360 MHz, DMSO-d$_6$) δ ppm 1.58-1.78 (m, 4H), 1.90-2.05 (m, 1H), 2.25-2.39 (m, 3H), 2.43 (s, 3H), 2.54 (s, 3H), 4.03 (t, J=7.5 Hz, 4H), 5.80 (br. s., 1H), 6.00 (s, 1H), 6.12 (d, J=1.1 Hz, 1H), 7.65 (d, J=1.8 Hz, 1H), 7.68-7.74 (m, 1H), 7.89 (s, 1H), 8.57 (s, 1H)

Synthesis of 4-(2-(5-(azetidin-1-yl)-6-methyl-7-(piperidin-1-yl)pyrazolo[1,5-a]-pyrimidin-2-yl)piperidin-1-yl)-6-methylquinazoline P22

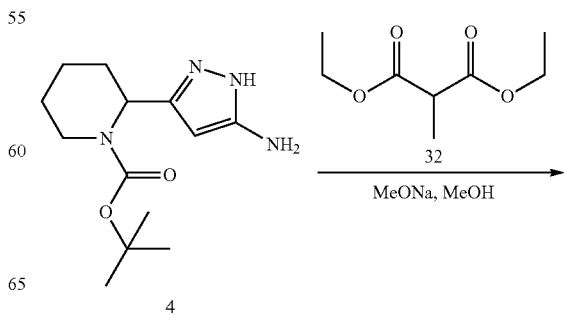

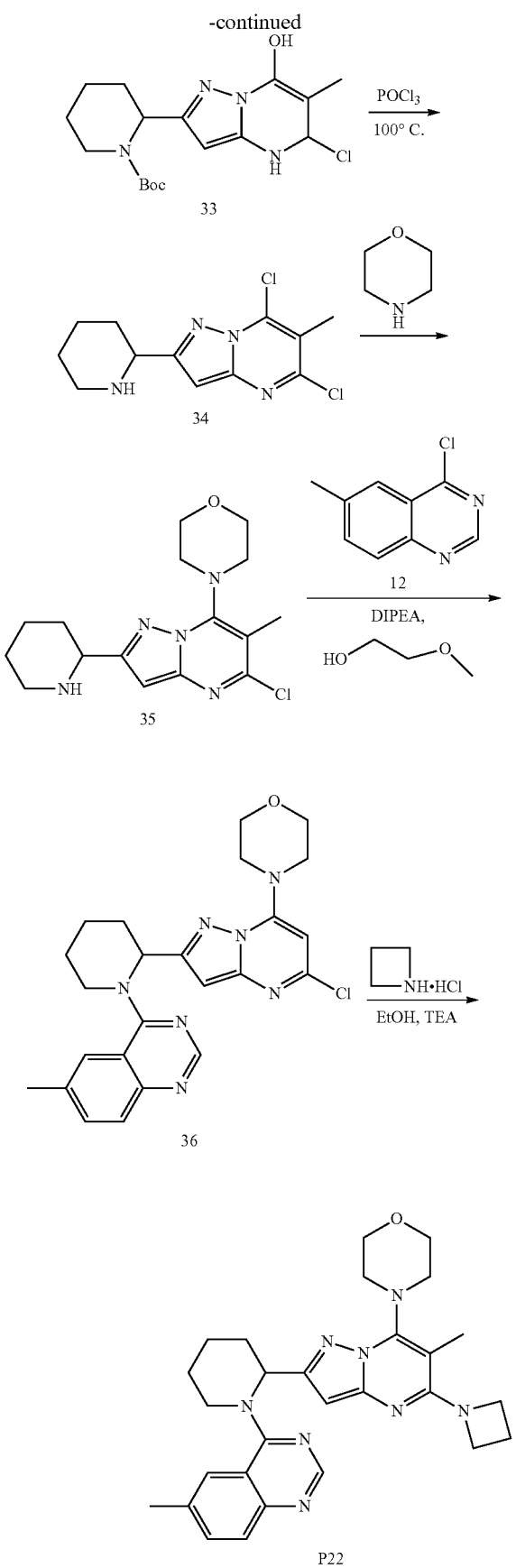

Step 1: synthesis of tert-butyl 2-(7-hydroxy-6-methyl-5-oxo-4,5-dihydropyrazolo-[1,5-a]pyrimidin-2-yl)piperidine-1-carboxylate 33

Freshly prepared sodium methanolate (50 ml, 93.87 mmol) was added to a solution of intermediate 4 (5 g, 18.77 mmol) and diethyl 2-methylmalonate 32 (3.93 g, 22.53 mmol) in methanol (50 ml). The solution was refluxed for 15 hours. The solvent was evaporated under vacuum. Water was added to the residue, the solution was adjusted to pH=4-5 by addition of acetic acid. The mixture was extracted with ethyl acetate (3×300 ml), the combined organic layers were washed with brine (2×100 ml), dried ($Na_2SO_4$), filtered and concentrated under vacuum to give the crude intermediate 33 (8.5 g, yield: 91%).

m/z=349 (M+H)$^+$

Step 2: 5,7-dichloro-6-methyl-2-(piperidin-2-yl)pyrazolo[1,5-a]pyrimidine 34

Phosphorus trichlorid (30 ml) was added to intermediate 33 (6.5 g, 18.66 mmol) at 0° C. The mixture was stirred at 100° C. for 15 hours. The solvent was evaporated under vacuum. The residue was dissolved in $CH_3CN$ (30 ml). The solution was adjusted to pH=7 by addition of ammonia methanol solution. The solvent was evaporated under vacuum. The residue was purified by column chromatography over silica gel (eluent: dichloromethane/methanol 20/1 (0.5% ammonia methanol solution)). The desired fractions were collected and the solvent was evaporated under vacuum. The residue was washed with ethyl acetate. The solid was dried under vacuum to yield intermediate 34 (1.12 g, 21%).

m/z=286 (M+H)$^+$ $^1$H NMR (400 MHz, $CDCl_3$) δ ppm 1.22-1.25 (m, 1H) 1.65-1.68 (m, 2H) 2.04-2.08 (m, 1H) 2.24-2.28 (m, 2H) 2.53 (s, 3H) 3.08 (br. s., 1H) 3.57 (br. s., 1H) 3.69-3.80 (m, 1H) 4.48 (br. s., 1H) 7.21 (s, 1H).

Step 3: synthesis of 5-chloro-6-methyl-7-(piperidin-1-yl)-2-(piperidin-2-yl)pyrazolo-[1,5-a]pyrimidine 35

A solution of intermediate 34 (1120 mg, 3.93 mmol), morpholine (377 mg, 4.32 mmol), Hunig's base (1.35 mL, 7.85 mmol) in ethanol (25 mL) was stirred at room temperature overnight. The mixture was evaporated and the residue was crystallised in diisopropyl-ether with about 50% acetonitrile. The crystals were collected by filtration and dried in vacuo to yield intermediate 35 (1060 mg, 80%)

m/z=335.8 (M+H)$^+$

Step 4: 4-(2-(5-chloro-6-methyl-7-(piperidin-1-yl)pyrazolo[1,5-a]pyrimidin-2-yl)-piperidin-1-yl)-6-methylquinazoline 36

A solution of intermediate 35 (1060 mg, 3.16 mmol), 4-chloro-6-methyl-quinazoline 12 (845.7 mg, 4.73 mmol), Hunig's base (1.1 mL, 6.32 mmol) and 2-methoxyethanol (20 mL) was stirred at 100° C. overnight. The mixture was evaporated and the residue was taken up in water and extracted with dichloromethane 3 times. The combined organic layer was successively dried over MgSO4, filtered and evaporated. The residue was purified over a silicagel chromatography with dichloromethane/methanol 98/2 as eluent. The corresponding fractions were evaporated to yield intermediate 36 (1400 mg, 92%)

Step 5: synthesis of 4-(2-(5-(azetidin-1-yl)-6-methyl-7-(piperidin-1-yl)pyrazolo-[1,5-a]pyrimidin-2-yl)piperidin-1-yl)-6-methylquinazoline P22

Compound P22 was prepared in the same manner as compound P21 using intermediate 36 as starting material.
m/z=498.6 (M+H)+

$^1$H NMR (400 MHz, DMSO-d$_6$) δ ppm 1.58-1.87 (m, 4H) 1.98-2.06 (m, 1H) 2.07 (s, 3H) 2.24 (quin, J=7.57 Hz, 2H) 2.34-2.40 (m, 1H) 2.42-2.46 (m, 3H) 3.34-3.40 (m, 4H) 3.49 (br ddd, J=13.62, 10.60, 3.63 Hz, 1H) 3.64-3.71 (m, 4H) 4.10 (t, J=7.67 Hz, 4H) 4.19 (br d, J=14.13 Hz, 1H) 5.81-5.88 (m, 1H) 5.92 (s, 1H) 7.59 (dd, J=8.48, 1.61 Hz, 1H) 7.65-7.73 (m, 1H) 7.86 (s, 1H) 8.53 (s, 1H)

Synthesis of 1-(6-methyl-2-(1-(5-methylquinazolin-4-yl)piperidin-2-yl)pyrazolo-[1,5-a]pyrimidin-5-yl)azetidin-3-ol P23

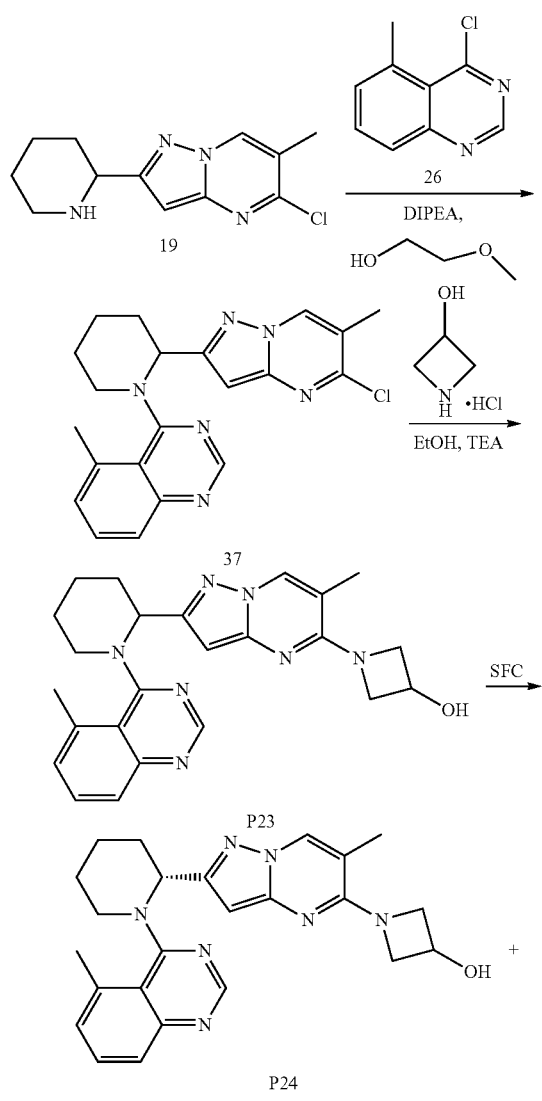

P24: [α]$_D$$^{20}$=+251.32° (589 nm, c=0.3975 w/v %, DMF, 20° C.)

P25: [α]$_D$$^{20}$=−264.8° (589 nm, c=0.375 w/v %, DMF, 20° C.)

Step 1: synthesis of 4-(2-(5-chloro-6-methylpyrazolo[1,5-a]pyrimidin-2-yl)piperidin-1-yl)-5-methylquinazoline 37

Intermediate 19 (500 mg, 1.72 mmol) was dissolved in 2-methoxyethanol (30 mL). DIPEA (0.89 mL, 5.17 mmol, 3 eq.) and 4-chloro-5-methylquinazoline 26 (324.26 mg, 1.72 mmol, 1 eq.) were added to the solution and heated to 80° C. After 16 hours stirring, the solution was concentrated in vacuo and purified via column chromatography (DCM/(NH$_3$/MeOH) 7N): 9/1) to yield the desired intermediate 37 (735 mg, 86%).
LCMS m/z=393 (M+H)+

Step 2: synthesis of 1-(6-methyl-2-(1-(5-methylquinazolin-4-yl)piperidin-2-yl)-pyrazolo[1,5-a]pyrimidin-5-yl)azetidin-3-ol P23

Intermediate 37 (735 mg, 1.5 mmol) was dissolved in EtOH (50 mL). Azetidin-3-ol hydrochloride (327 mg, 3 mmol, 2 eq.) and DIPEA (0.77 mL, 4.5 mmol, 3 eq.) were added and the solution was heated to reflux during 16 hours. The solution was then cooled to room temperature, ice was added and the solution was stirred for 1 hour. The solid was filtered off and dried into the oven to yield compound P23 (440 mg, 68%) LCMS m/z=430 (M+H)+

$^1$H NMR (400 MHz, 420 K, DMSO-d$_6$) δ ppm 1.41-1.70 (m, 3H) 1.76-1.89 (m, 1H) 2.11 (d, J=1.21 Hz, 3H) 2.13-2.31 (m, 2H) 2.81 (s, 3H) 3.42-3.60 (m, 2H) 3.90 (dd, J=9.28, 4.84 Hz, 2H) 4.34 (t, J=8.10 Hz, 2H) 4.46-4.55 (m, 1H) 4.73-5.12 (m, 1H) 5.47-5.58 (m, 1H) 5.64 (br. s., 1H) 7.21-7.33 (m, 1H) 7.46-7.63 (m, 2H) 8.10 (s, 1H) 8.45 (s, 1H)

(R)-1-(6-methyl-2-(1-(5-methylquinazolin-4-yl)piperidin-2-yl)pyrazolo[1,5-a]-pyrimidin-5-yl)azetidin-3-ol P24 and (S)-1-(6-methyl-2-(1-(5-methylquinazolin-4-yl)-piperidin-2-yl)pyrazolo[1,5-a]pyrimidin-5-yl)azetidin-3-ol P25

These two enantiomers were isolated by SFC separation using compound P23 A purification was performed via Prep SFC (Stationary phase: Chiralpak Diacel AS 20×250 mm, Mobile phase: CO2, EtOH with 0.2% iPrNH2) giving both relative enantiomers:

Synthesis of 1-(6-methyl-2-(1-(5-methylquinazolin-4-yl)piperidin-2-yl)pyrazolo-[1,5-a]pyrimidin-5-yl)azetidin-3-amine P26

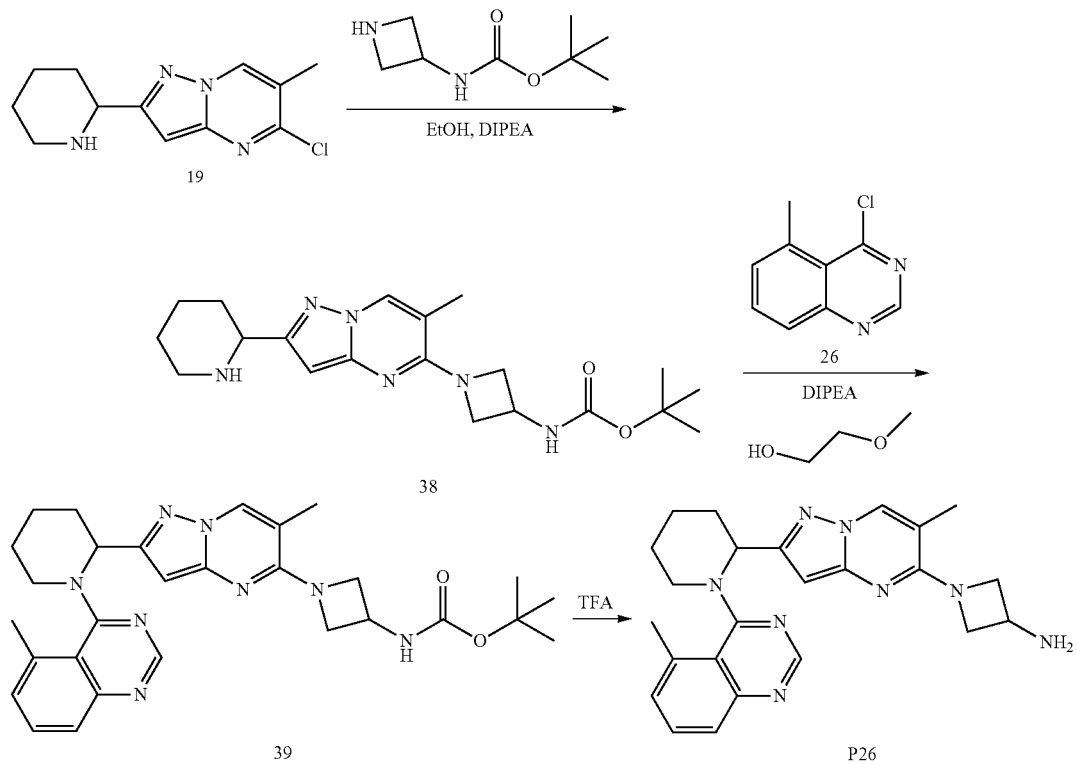

Step 1: synthesis of tert-butyl(1-(6-methyl-2-(piperidin-2-yl)pyrazolo[1,5-a]-pyrimidin-5-yl)azetidin-3-yl)carbamate 38

A solution of intermediate 19 (1300 mg, 5.185 mmol), tert-butylazetidin-3-ylcarbamate (1786 mg, 10.37 mmol) and Hunig's base (2 ml, 11.606 mmol) in EtOH (30 ml) was heated at 70° C. for 3 hours. After cooling to room temperature, dicalite was added and the mixture was evaporated to dryness. The crude was purified by column chromatography. The column was eluted with a gradient starting with 100% DCM to 10% MeOH and 90% DCM. The fractions containing product were evaporated and the residue was recrystallized in ACN. After filtration we get a white crystalline solid, this is a mixture of the desired title intermediate 38 and starting reagent tert-butylazetidin-3-ylcarbamate (2204 mg), which was used as such in the next step.

m/z=387.26 (M+H)$^+$

Step 2: synthesis of tert-butyl(1-(6-methyl-2-(1-(5-methylquinazolin-4-yl)piperidin-2-yl)pyrazolo[1,5-a]pyrimidin-5-yl)azetidin-3-yl)carbamate 39

The crude made in step 1, intermediate 38 (250 mg, 0.647 mmol), 4-chloro-5-methyl-quinazoline 26 (182 mg, 0.97 mmol) and Hunig's base (368 µl, 2.135 mmol) were mixed in 2-methoxyethanol (4.36 ml) and heated at 100° C. for 3 hours. The reaction mixture was evaporated and the residue was purified by column chromatography by eluting with a gradient starting with 100% DCM to 5% MeOH and 95% DCM. All fractions containing product were evaporated to get yellow foam which was only 52% pure (315 mg). The crude was used as such in step 3.

m/z=529.28 (M+H)$^+$

Step 3: 1-(6-methyl-2-(1-(5-methylquinazolin-4-yl)piperidin-2-yl)pyrazolo[1,5-a]-pyrimidin-5-yl)azetidin-3-amine P26

The crude made in step 2, intermediate 39 (157 mg, 0.297 mmol) was dissolved in DCM (1.9 ml). Then TFA (227 µl, 2.97 mmol) was added and the reaction mixture was stirred at room temperature for 16 hours. The mixture was basified by 7 M NH$_3$ in MeOH and all solvents were evaporated. The residue was triturated in water and the formed solid was filtered off and purified by column chromatography. The column was eluted with a gradient starting from 100% DCM to 10% (MeOH/NH$_3$) and 90% DCM. All pure fractions were evaporated to get the title product P26 as a white solid (76 mg, 59%).

m/z=429.30 (M+H)$^+$

MP=221.07° C.

$^1$H NMR at 150° C. (400 MHz, DMSO-d$_6$) δ ppm 8.46 (s, 1H), 8.10 (s, 1H), 7.64-7.53 (m, 2H), 7.28 (d, J=5.9 Hz, 1H), 5.75-5.37 (m, 2H), 4.41-4.22 (m, 2H), 3.87-3.71 (m, 3H), 3.60-3.37 (m, 2H), 2.81 (s, 3H), 2.31-2.12 (m, 2H), 2.10 (s, 3H), 1.94-1.32 (m, 6H)

Synthesis of 1-(2-(1-(2,5-dimethylquinazolin-4-yl)piperidin-2-yl)-6-methyl-pyrazolo[1,5-a]pyrimidin-5-yl)azetidin-3-amine P27

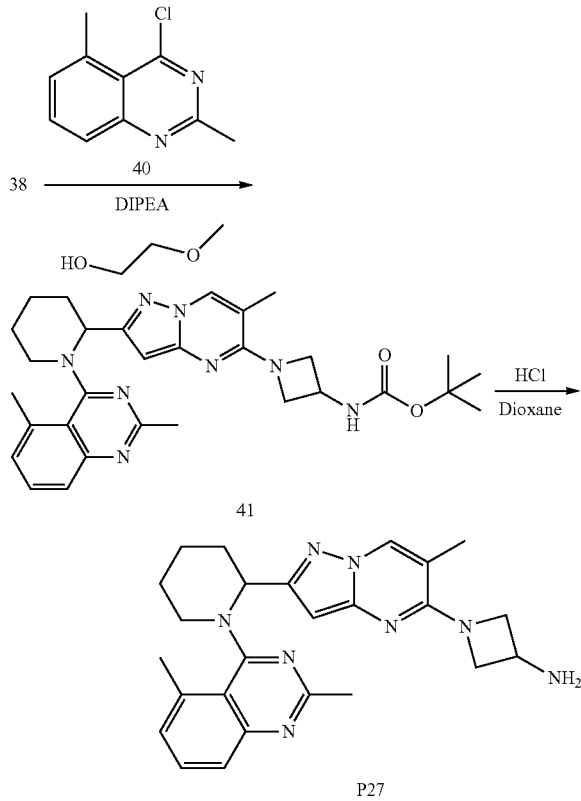

Synthesis of 4-chloro-2,5-dimethylquinazoline 40

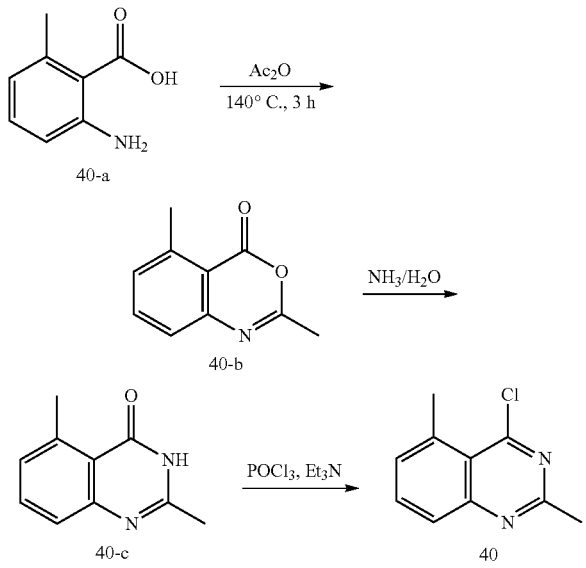

Step 1: synthesis of 2,5-dimethyl-4H-benzo[d][1,3]oxazin-4-one 40-b

A solution of 2-amino-6-methylbenzoic acid 40-a (20.0 g, 132 mmol) in acetic anhydride (100 ml) was stirred at 140° C. for 3 hours. The mixture was concentrated under vacuum to give the title intermediate 40-b (20.0 g, 77.7%).

Step 2: synthesis of 2,5-dimethylquinazolin-4(3H)-one 40-c

A mixture of intermediate 40-b (20.0 g, 114 mmol) and ammonium hydroxide (50 ml) was refluxed overnight. The mixture was cooled to 25° C. The solid was collected by filtration and washed with water. The filter cake was dried under vacuum at 40° C. for 1 hour to yield the title intermediate 40-c (20 g, 90.5%).

Step 3: synthesis of 4-chloro-2,5-dimethylquinazoline 40

Triethyl amine (5.05 g, 49.9 mmol) was added to a mixture of intermediate 40-c (2.90 g, 16.7 mmol) in phosphorus oxychloride (108 g, 709 mmol) at 0° C. The mixture was refluxed for 3 hours. The solvent was evaporated under vacuum. The residue was dissolved in toluene (50 ml) and the solution was added to ice water (50 g). The organic layer was separated and washed successively with water (2×50 ml), 10% aqueous $NaHCO_3$ solution (2×50 ml), water (2×50 ml), brine (50 ml). The organic layer was dried ($MgSO_4$), filtered and the filtrate was concentrated under vacuum to yield intermediate 40 (1.91 g, 58.61%)

$^1$H NMR (400 MHz, $CDCl_3$) δ ppm 2.80 (s, 3H) 3.00 (s, 3H) 7.41 (d, J=7.28 Hz, 1H) 7.68-7.76 (m, 1H) 7.78-7.85 (m, 1H).

Step 4: synthesis of tert-butyl(1-(2-(1-(2,5-dimethylquinazolin-4-yl)piperidin-2-yl)-6-methylpyrazolo[1,5-a]pyrimidin-5-yl)azetidin-3-yl)carbamate 41

The crude intermediate 38, (250 mg, 0.647 mmol), intermediate 40 (190 mg, 0.97 mmol) and Hunig's base (368 μl, 2.135 mmol) were mixed in 2-methoxyethanol (4.36 ml) and heated at 100° C. for 3 hours. The reaction mixture was evaporated and the residue was purified by column chromatography by eluting with a gradient starting with 100% DCM to 5% MeOH and 95% DCM. All fractions containing product were evaporated to get a yellow foam of intermediate 41 which was only 55% pure (427 mg). The crude was used as such in step 5.

m/z=543.36 (M+H)$^+$

Step 5: synthesis of 1-(2-(1-(2,5-dimethylquinazolin-4-yl)piperidin-2-yl)-6-methyl-pyrazolo[1,5-a]pyrimidin-5-yl)azetidin-3-amine P27

The crude intermediate 41 (427 mg (only 55% pure), 0.433 mmol) was dissolved in a 4 M solution of HCl in dioxane (21.64 ml, 86.551 mmol) and the reaction mixture was stirred at room temperature for 2 hours. The mixture was diluted with dichloromethane and then basified with saturated $Na_2CO_3$ solution. The product was extracted with dichloromethane (3×15 mL). The organic layers were dried over $Na_2SO_4$, filtered and evaporated. The crude was purified by column chromatography. The silica column was eluted with a gradient starting from 100% DCM to 4% (MeOH/$NH_3$) and 96% DCM. All pure fractions were evaporated. The residue was triturated in DIPE to get the title product P27 as a white solid (11 mg, 6%).

m/z=443.6 (M+H)+

MP=176.85° C.

$^1$H NMR at 150° C. (400 MHz, DMSO-$d_6$) δ ppm 8.10 (s, 1H), 7.56-7.43 (m, 2H), 7.19 (d, J=6.8 Hz, 1H), 5.74-5.44 (m, 2H), 4.39-4.25 (m, 2H), 3.83-3.71 (m, 3H), 3.53-3.38 (m, 2H), 2.79 (s, 3H), 2.45 (s, 3H), 2.26-2.13 (m, 2H), 2.11 (s, 3H), 1.94-1.38 (m, 6H)

Synthesis of dimethyl (4-{2-[5-(azetidin-1-yl)-7-(morpholin-4-yl)pyrazolo[1,5-a]-pyrimidin-2-yl]piperidin-1-yl}-5-methylquinazolin-2-yl)imidodicarbonate P28

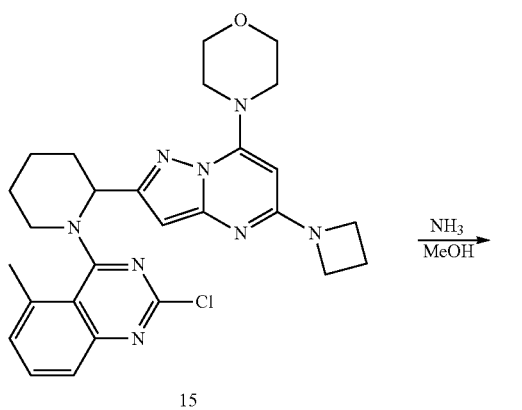

Step 1: synthesis of 4-(2-(5-(azetidin-1-yl)-7-morpholinopyrazolo[1,5-a]pyrimidin-2-yl)piperidin-1-yl)-5-methylquinazolin-2-amine 42

A suspension of intermediate 15 (1031 mg, 1.902 mmol) in a 7 M solution of NH$_3$ in MeOH (25 ml, 175 mmol) was heated in a sealed metal reactor at 120° C. for 4 days. After evaporation, the residue was purified by HPLC purification. The purified product was dissolved in a mixture of DCM and DIPE, and the solution was evaporated again to get the title intermediate 42 as a white solid (473 mg, 47%).

m/z=500.3 (M+H)+

MP=252.24° C.

$^1$H NMR at 150° C. (400 MHz, DMSO-$d_6$) δ ppm 7.36-7.27 (m, 1H), 7.16-7.10 (m, 1H), 6.90-6.83 (m, 1H), 5.71-5.60 (m, 1H), 5.54-5.41 (m, 2H), 5.31-5.22 (m, 1H), 5.17 (s, 1H), 3.98 (t, J=7.5 Hz, 4H), 3.78-3.28 (m, 10H), 2.76 (s, 3H), 2.28 (quin, J=7.4 Hz, 2H), 2.21-2.07 (m, 2H), 1.90-1.44 (m, 4H)

Step 2: synthesis of dimethyl (4-{2-[5-(azetidin-1-yl)-7-(morpholin-4-yl)pyrazolo-[1,5-a]pyrimidin-2-yl]piperidin-1-yl}-5-methylquinazolin-2-yl)imidodicarbonate P28

Intermediate 42 (100 mg, 0.188 mmol) was dissolved in DCM (2.21 ml). Then DIPEA (117 μl, 0.678 mmol) and methyl chloroformate (cas=79-22-1, 29 μl, 0.376 mmol) were added. The reaction mixture was stirred at room temperature for 2 hours. DCM was evaporated and the residue was triturated in water. The suspension was sonicated for 30 minutes and stirred at room temperature overnight. The solid was filtered and washed with water and DIPE to obtain the title compound P28 as a white powder (40 mg, 31%).

m/z=616.6 (M+H)+

MP=136.62° C.

$^1$H NMR (400 MHz, DMSO-$d_6$) δ ppm 7.79-7.66 (m, 1H), 7.65-7.55 (m, 1H), 7.48-7.39 (m, 1H), 6.05-4.99 (m, 3H), 4.09-3.02 (m, 20H), 2.89-2.73 (m, 3H), 2.38-1.94 (m, 4H), 1.87-1.40 (m, 4H)

Synthesis of methyl (4-(2-(5-(azetidin-1-yl)-7-morpholinopyrazolo[1,5-a]-pyrimidin-2-yl)piperidin-1-yl)-5-methylquinazolin-2-yl)carbamate P29

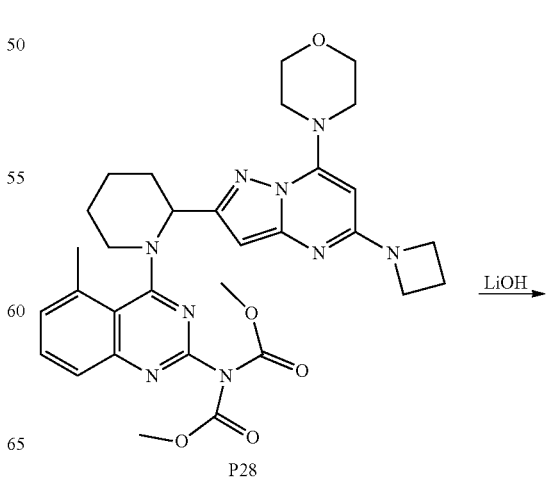

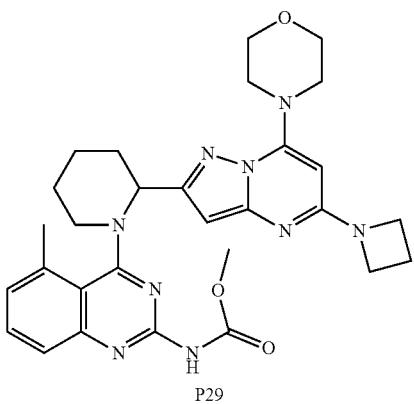

P29

Compound P28 (200 mg, 0.279 mmol) was dissolved in MeOH (6.0 ml) and THF (6.0 ml). Then a solution of LiOH (17 mg, 0.722 mmol) in water (4.3 ml) was added.

The resulting mixture was stirred at room temperature for 3 hours. Then it was neutralized with 1 M HCl solution and diluted with some water. The suspension was stirred at room temperature overnight. The white solid was collected by filtration and the desired product was dried in vacuum oven overnight to yield a white solid P29 (71 mg, 43%).

$^1$H NMR at 80° C. (400 MHz, DMSO-$d_6$) δ ppm 9.70-9.32 (m, 1H), 7.53 (dd, J=7.3, 8.1 Hz, 1H), 7.38 (d, J=8.1 Hz, 1H), 7.14 (d, J=7.0 Hz, 1H), 6.25-4.79 (m, 3H), 3.99 (t, J=7.4 Hz, 4H), 3.80-3.67 (m, 5H), 3.65 (s, 3H), 3.60-3.32 (m, 5H), 2.77 (s, 3H), 2.35-2.13 (m, 4H), 1.91-1.33 (m, 4H)

m/z=558.3 (M+H)$^+$

Synthesis of 4-(2-(5-(azetidin-1-yl)-7-morpholinopyrazolo[1,5-a]pyrimidin-2-yl)-piperidin-1-yl)-N-hydroxy-5-methylquinazoline-2-carboximidamide P30

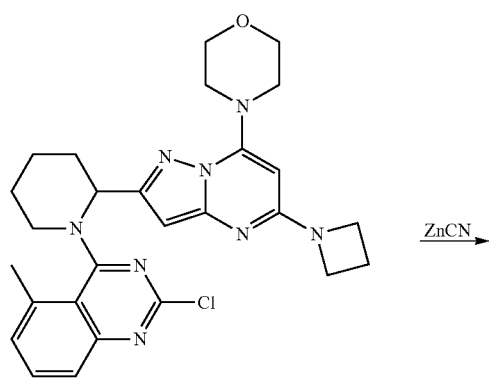

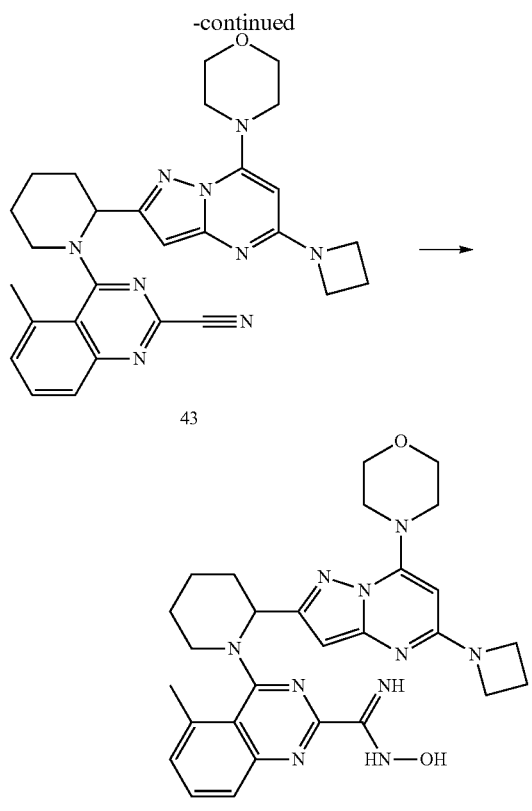

Step 1: synthesis of 4-(2-(5-(azetidin-1-yl)-7-morpholinopyrazolo[1,5-a]pyrimidin-2-yl)piperidin-1-yl)-5-methylquinazoline-2-carbonitrile 43

A yellow solution of 15 (2000 mg, 3.689 mmol), zinc cyanide (cas=557-21-1, 521 mg, 4.433 mmol) and 1,1'-bis(diphenylphosphino)ferrocene (cas=12150-46-8, 372 mg, 0.671 mmol) in NMP (44.6 ml) was degassed with N$_2$ during 30 minutes. Then tris(dibenzylideneacetone)dipalladium(0) (cas=51364-51-3, 327 mg, 0.357 mmol) was added and the reaction vessel was sealed and heated at 90° C. for 20 hours. The reaction mixture was quenched with water (176 ml) and a precipitation was formed immediately. This suspension was stirred at room temperature overnight. The solid was filtered and washed with water to get a dark brown solid. The wet brown solid was dissolved in DCM and the remaining water was removed by separation and drying over Na$_2$SO$_4$. The residue was recrystallized in ACN and the mixture was stirred overnight. The black crystals were filtered, washed with ACN and MeOH to get purple/grey crystals. The solid was recrystallized again in ACN and stirred for 6 hours. Then the formed purple crystals intermediate 43 was filtered, washed with a little ACN and dried in the vacuum oven (1685 mg, 81%).

m/z=510.3 (M+H)$^+$

Step 2: synthesis of 4-(2-(5-(azetidin-1-yl)-7-morpholinopyrazolo[1,5-a]pyrimidin-2-yl)piperidin-1-yl)-N-hydroxy-5-methylquinazoline-2-carboximidamide P30

To a solution of hydroxylamine hydrochloride (3753 mg, 54 mmol) in water (12.5 ml) was added Na$_2$CO$_3$ (625 mg, 5.9 mmol) and the mixture was stirred for 30 minutes. Then a suspension of intermediate 43 (1132 mg, 2 mmol) in EtOH (50 ml) was added at room temperature. The resulting mixture was stirred for 16 hours. Iced water was added. After stirring for 2 hours, the beige solid was filtered and washed with DIPE. The crude was suspended in a mixture of 95% DCM and 5% MeOH and the remaining precipitate was filtered off. The filtrate was purified by column chromatography. The silica column was eluted by a gradient starting with 100% DCM to 10% (MeOH/NH$_3$) and 90% DCM. After evaporation of the pure fractions we get the desired product P30 as a beige solid (38 mg, 3%).

m/z=543.6 (M+H)$^+$

MP=205.46° C.

$^1$H NMR (400 MHz, DMSO-d$_6$) δ ppm 9.82-9.46 (m, 1H), 7.71-7.56 (m, 2H), 7.32 (dd, J=1.4, 6.3 Hz, 1H), 5.97-5.40 (m, 4H), 5.20 (s, 1H), 3.98 (t, J=7.4 Hz, 4H), 3.81-3.29 (m, 10H), 2.84 (s, 3H), 2.28 (quin, J=7.4 Hz, 2H), 2.23-2.11 (m, 2H), 1.90-1.38 (m, 4H)

Synthesis of 4-(5-(azetidin-1-yl)-2-(1-(2-ethoxy-5-methylquinazolin-4-yl)piperidin-2-yl)pyrazolo[1,5-a]pyrimidin-7-yl)morpholine P31

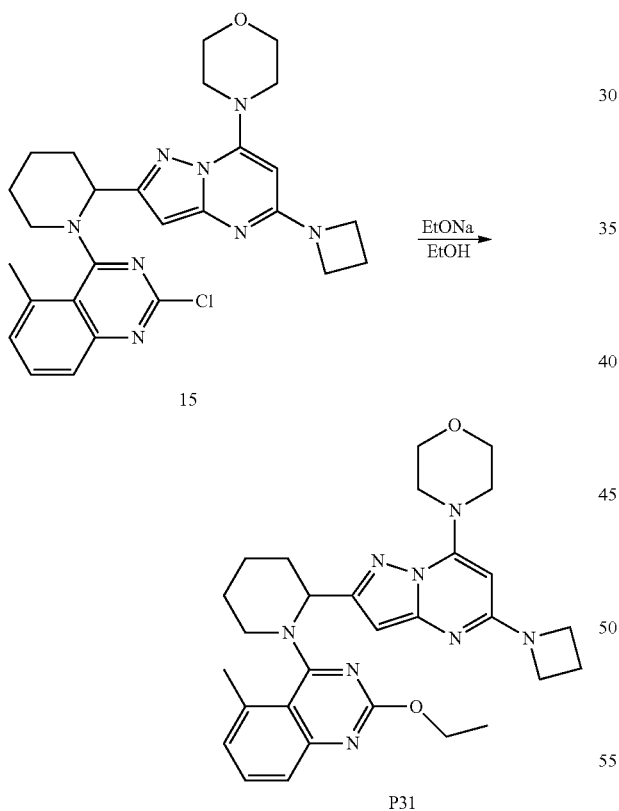

A suspension of intermediate 15 (150 mg, 0.277 mmol) in EtOH (2.39 ml) was treated with NaOEt (21% in EtOH) (525 µl, 1.407 mmol). The sample was flushed with N$_2$, sealed and heated at 80° C. for 48 hours. The reaction mixture was evaporated to dryness and the residue was purified by column chromatography by eluting with a gradient starting from 100% DCM to 10% MeOH and 90% DCM. All fractions containing product were evaporated to get white foam. The foam was recrystallized with DIPE and 5% ACN and the mixture was stirred for 3 days. The white crystalline title compound P31 was obtained by filtration (46 mg, 29%).

m/z=529.3 (M+H)$^+$

MP=186.90° C.

$^1$H NMR (400 MHz, DMSO-d$_6$) δ ppm 7.52-7.42 (m, 1H), 7.35 (d, J=8.1 Hz, 1H), 7.09 (d, J=7.0 Hz, 1H), 5.70-5.58 (m, 1H), 5.41-5.28 (m, 1H), 5.18 (s, 1H), 4.39-4.27 (m, 2H), 4.05-3.90 (m, 4H), 3.74-3.57 (m, 4H), 3.56-3.37 (m, 6H), 2.80 (s, 3H), 2.35-2.23 (m, 2H), 2.22-2.11 (m, 2H), 1.94-1.40 (m, 4H), 1.27 (t, J=6.9 Hz, 3H)

Synthesis of (S)—N-(4-(2-(5-(azetidin-1-yl)-7-morpholinopyrazolo[1,5-a]pyrimidin-2-yl)piperidin-1-yl)-6-chloroquinazolin-2-yl)methanesulfonamide P32

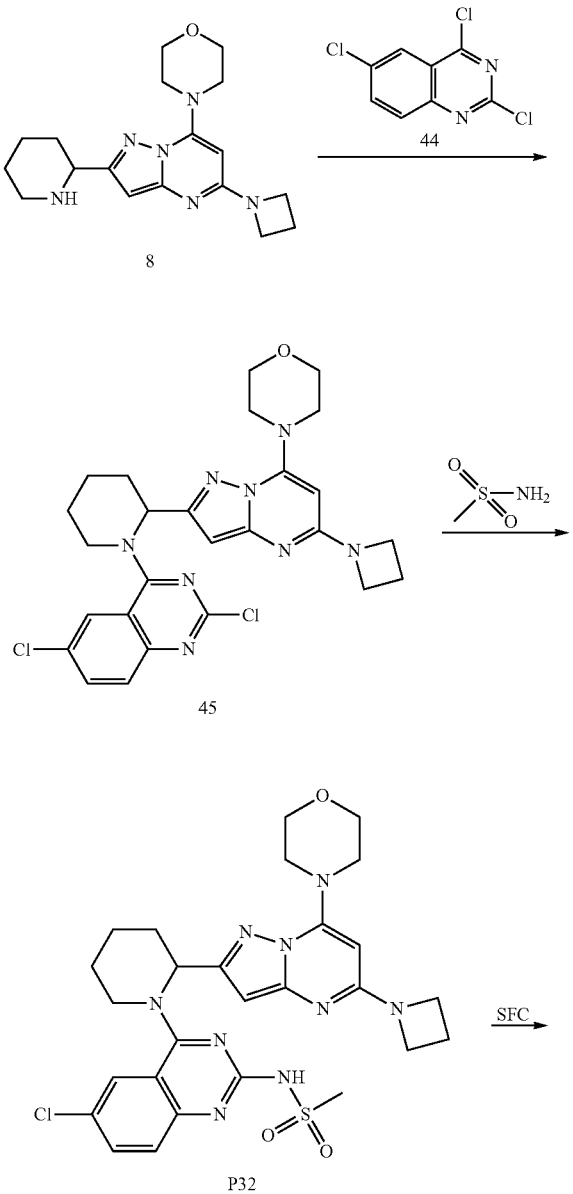

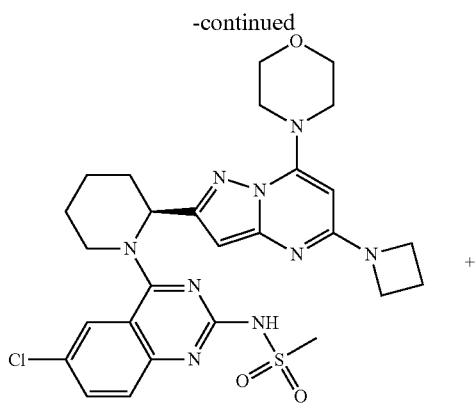

P33

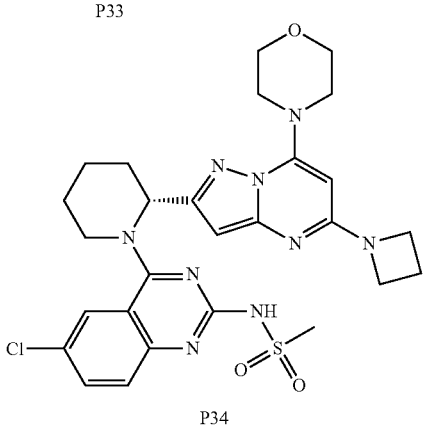

P34

P33: $[\alpha]_D^{20}=-209.83°$ (589 nm, c=0.3765 w/v %, DMF, 20° C.)
P34: $[\alpha]_D^{20}=+192.15°$ (589 nm, c=0.242 w/v %, DMF, 20° C.)

Step 1: synthesis of 4-(5-(azetidin-1-yl)-2-(1-(2,6-dichloroquinazolin-4-yl)piperidin-2-yl)pyrazolo[1,5-a]pyrimidin-7-yl)morpholine 45

Intermediate 8 (1341 mg, 2.92 mmol), 2,4,6-trichloroquinazoline 44 (cas=20028-68-6, 768 mg, 2.83 mmol) and DIPEA (cas=7087-68-5, 1.24 ml, 7.183 mmol) were mixed in 2-methoxyethanol (14.7 ml) and heated at 60° C. for 2 hours. The cooled reaction mixture was added slowly to iced water and the mixture was warmed to room temperature. The formed bright yellow precipitate was successively filtered, washed with water and DIPE and dried in the vacuum oven. The product was purified by column chromatography by eluting with a gradient starting with 100% DCM to 5% MeOH and 95% DCM. After evaporation of the fractions a yellow foam was isolated as intermediate 45 (781 mg, 49%).

$^1$H NMR (400 MHz, DMSO-d$_6$) δ ppm 8.12 (d, J=2.2 Hz, 1H), 7.85 (dd, J=2.2, 9.0 Hz, 1H), 7.74 (d, J=8.8 Hz, 1H), 6.07 (s, 1H), 5.97-5.88 (m, 1H), 5.35 (s, 1H), 4.34-4.20 (m, 1H), 4.02 (t, J=7.5 Hz, 4H), 3.77-3.60 (m, 4H), 3.59-3.34 (m, 5H), 2.42-2.22 (m, 3H), 2.09-1.93 (m, 1H), 1.79-1.59 (m, 4H)

m/z=539.3 (M+H)$^+$

Step 2: synthesis of N-(4-(2-(5-(azetidin-1-yl)-7-morpholinopyrazolo[1,5-a]pyrimidin-2-yl)piperidin-1-yl)-6-chloroquinazolin-2-yl)methanesulfonamide P32

The intermediate 45 (750 mg, 1.39 mmol), methane sulfonamide (264 mg, 2.781 mmol), cesium carbonate (cas=534-17-8, 1132 mg, 3.476 mmol), 4,5-bis-(diphenylphosphino)-9,9-dimethylxanthene (cas=161265-03-8, 241 mg, 0.417 mmol) and palladium(II)acetate (cas=3375-31-3, 94 mg, 0.417 mmol) were mixed in dioxane (10 ml). The suspension was degassed with N$_2$ for 10 minutes. The reaction vessel was sealed and then heated at 110° C. for 30 minutes in a g-wave oven. The reaction mixture was filtered and the filtrate was evaporated to dryness to be purified by column chromatography by eluting with a gradient starting with 100% DCM to 10% (MeOH/NH$_3$) and 90% DCM. After evaporation of the concerning fractions we get the title product P32 as a brown solid (507 mg, 59%).

m/z=598.2 (M+H)$^+$ $^1$H NMR (400 MHz, DMSO-d$_6$) δ ppm 12.06 (br. s., 1H), 8.13-7.91 (m, 1H), 7.76 (dd, J=2.2, 9.0 Hz, 1H), 7.41 (d, J=8.8 Hz, 1H), 6.38-5.80 (m, 2H), 5.37 (s, 1H), 4.56-4.30 (m, 1H), 4.03 (t, J=7.5 Hz, 4H), 3.79-3.64 (m, 4H), 3.60-3.35 (m, 5H), 3.11-2.87 (m, 3H), 2.44-2.25 (m, 3H), 2.09-1.89 (m, 1H), 1.82-1.60 (m, 4H)

Step 3: synthesis of (S)—N-(4-(2-(5-(azetidin-1-yl)-7-morpholinopyrazolo[1,5-a]-pyrimidin-2-yl)piperidin-1-yl)-6-chloroquinazolin-2-yl)methanesulfonamide P33 and (R)—N-(4-(2-(5-(azetidin-1-yl)-7-morpholinopyrazolo[1,5-a]-pyrimidin-2-yl)piperidin-1-yl)-6-chloroquinazolin-2-yl)methanesulfonamide P34

Compound P32 (400 mg, 0.669 mmol) was purified by SFC to obtain the title compound, pure enantiomer P33, as a yellowish solid (173 mg, 43%) and pure enantiomer P34, as a yellowish solid (187 mg, 46%).

P33, SFC: 100% pure, R$_t$=1.94 min m/z=598.2 (M+H)$^+$

P34, SFC: 98.65% Pure, 1.35% R$_t$=1.89 min and 98.65% R$_t$=2.74 min.

m/z=598.2 (M+H)$^+$

Synthesis of 4-(5-(azetidin-1-yl)-2-(1-(5-chloroquinazolin-4-yl)piperidin-2-yl)-pyrazolo[1,5-a]pyrimidin-7-yl)morpholine P35

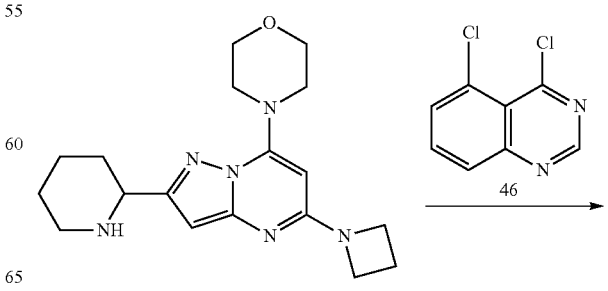

8

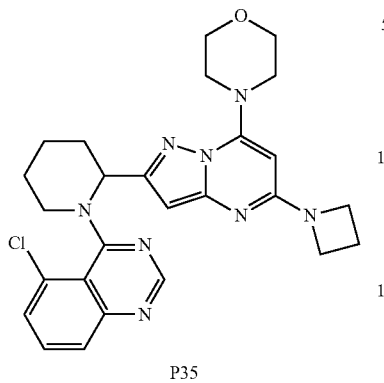

P35

To a solution of intermediate 8 (300 mg, 0.63 mmol) in 2-methoxyethanol (20 mL) was added 4,5-dichloroquinazoline 46 (CAS: 2148-55-2, 1.1 eq., 139 mg, 0.7 mmol) and DIPEA (3 eq., 0.33 mL, 1.9 mmol). The solution was heated to 80° C. for 16 hours. The solution was concentrated in vacuum, extracted with DCM and washed with water. The combined organics were collected and dried with MgSO4, filtered off and concentrated in vacuum. The crude was purified by column chromatography eluting with a gradient starting from 0% to 10% MeOH in DCM. After evaporation compound P35 (190 mg, 57%) was obtained.

LCMS m/z=505 (M+H)+

$^1$H NMR (400 MHz, 420 K, DMSO-$d_6$) δ ppm 1.48-1.90 (m, 4H) 2.22-2.35 (m, 4H) 3.43-3.56 (m, 5H) 3.64-3.76 (m, 4H) 3.84 (d, J=13.89 Hz, 1H) 3.93-4.04 (m, 4H) 5.18 (s, 1H) 5.62 (s, 1H) 5.66 (br. s., 1H) 7.51 (dd, J=7.16, 1.61 Hz, 1H) 7.61-7.66 (m, 1H) 7.67-7.70 (m, 1H) 8.45 (s, 1H)

Synthesis of 4-(2-(5-(azetidin-1-yl)-7-morpholin-opyrazolo[1,5-a]pyrimidin-2-yl)-piperidin-1-yl)-N—(N,N-dimethylsulfamoyl)quinazoline-2-carboxamide P36

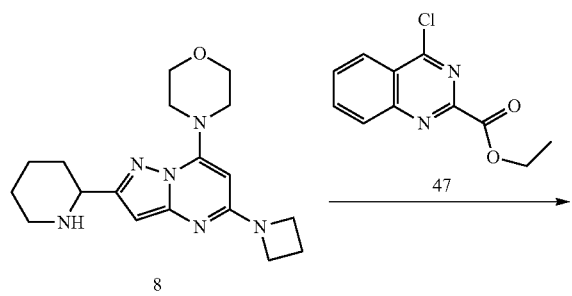

8  47

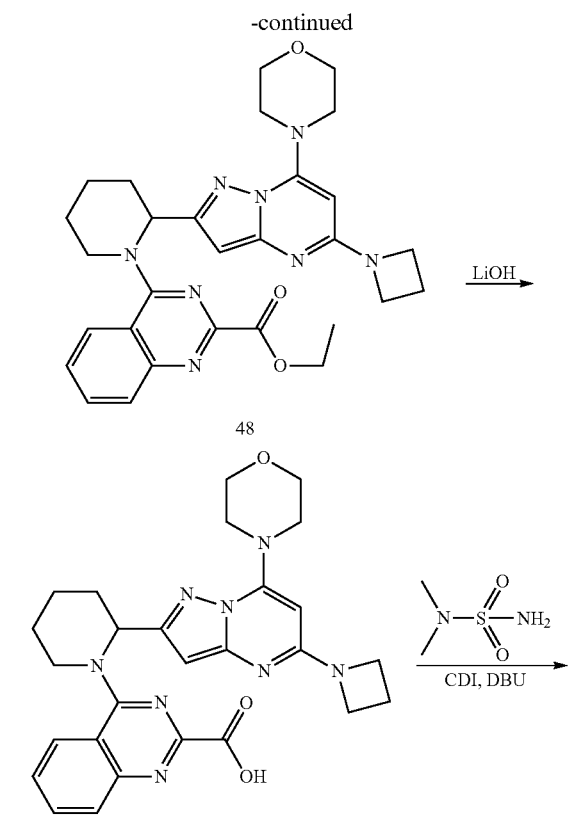

Step 1: synthesis of ethyl 4-(2-(5-(azetidin-1-yl)-7-morpholinopyrazolo[1,5-a]-pyrimidin-2-yl)piperidin-1-yl)quinazoline-2-carboxylate 48

To a solution of intermediate 8 (1.2 g, 3.4 mmol) in 2-methoxyethanol (40 mL) was added ethyl 4-chloroquinazoline-2-carboxylate 47 (0.97 g, 4.06 mmol) and DIPEA (3 eq., 1.75 mL, 10 mmol). The solution was stirred at 80° C. for 48 hours. After cooling to room temperature the solution was concentrated in vacuum and purified by column chromatography eluting with a gradient starting from 0% to 10% MeOH in DCM to give intermediate 48 (998 mg, 75% pure, 40% yield) which was used as such into the next step.

LCMS m/z=543 (M+H)+

Step 2: synthesis of 4-(2-(5-(azetidin-1-yl)-7-morpholinopyrazolo[1,5-a]pyrimidin-2-yl)piperidin-1-yl)quinazoline-2-carboxylic acid 49

To a solution of intermediate 48 (998 mg, 75% pure, 1.3 mmol) in 25 ml THF/water (3/1), was added LiOH (3 eq., 93 mg, 3.9 mmol). The solution was stirred at room temperature during 16 hours. The solution was then adjusted to pH=6 and the mixture was concentrated in vacuum giving intermediate 49 (828 mg, 76% pure, 94% yield), which was used as such in the next step.
LCMS m/z=515 (M+H)+

Step 3: synthesis of 4-(2-(5-(azetidin-1-yl)-7-morpholinopyrazolo[1,5-a]pyrimidin-2-yl)piperidin-1-yl)-N—(N,N-dimethylsulfamoyl)quinazoline-2-carboxamide P36

To a solution intermediate 49 (300 mg, 0.37 mmol) was added CDI (120 mg, 0.73 mmol) in 3 mL THF/DMF (1/1) solution. The solution was heated to 50° C. and stirred for one hour. N,N-Dimethylsulfamide (136 mg, 1.1 mmol) and DBU (0.165 mL, 1.1 mmol) was added to the solution and stirred for an additional hour at 50° C. The solution was extracted with DCM and washed with water. The combined organics were dried with MgSO4 and concentrated in vacuum. The crude was further purified by column chromatography eluting with a gradient starting from 0% to 10% MeOH in DCM. After evaporation the crude was taken up in water and the solid filtered off and dried into the oven to yield compound P36 (53 mg, 22%) as a white solid.
LCMS m/z=621 (M+H)+
1H NMR (400 MHz, 360 K, DMSO-d6) δ ppm 1.69-1.81 (m, 4H) 2.02-2.13 (m, 1H) 2.26-2.35 (m, 3H) 2.35-2.42 (m, 1H) 2.90 (s, 6H) 3.49-3.57 (m, 5H) 3.62-3.72 (m, 4H) 4.01 (t, J=7.48 Hz, 4H) 4.37 (d, J=13.42 Hz, 1H) 5.27 (s, 1H) 5.94 (s, 1H) 6.05 (br. s, 1H) 7.57-7.61 (m, 1H) 7.83-7.88 (m, 1H) 7.93 (dd, J=8.36, 1.10 Hz, 1H) 8.15 (d, J=8.58 Hz, 1H)

Synthesis of 1-(2-(1-(2, 5-dimethylquinazolin-4-yl)piperidin-2-yl)-6-methyl-pyrazolo[1,5-a]pyrimidin-5-yl)azetidin-3-ol P37

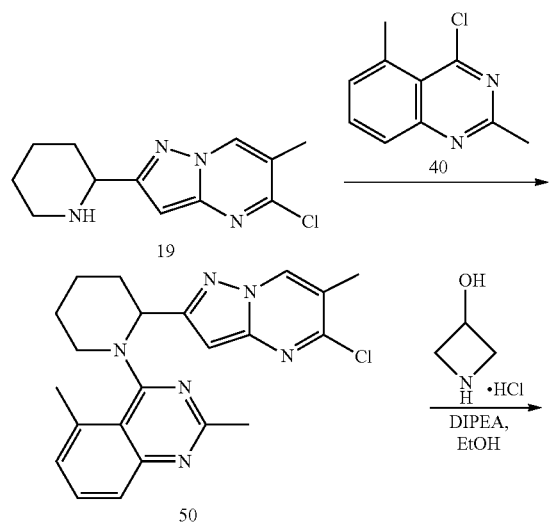

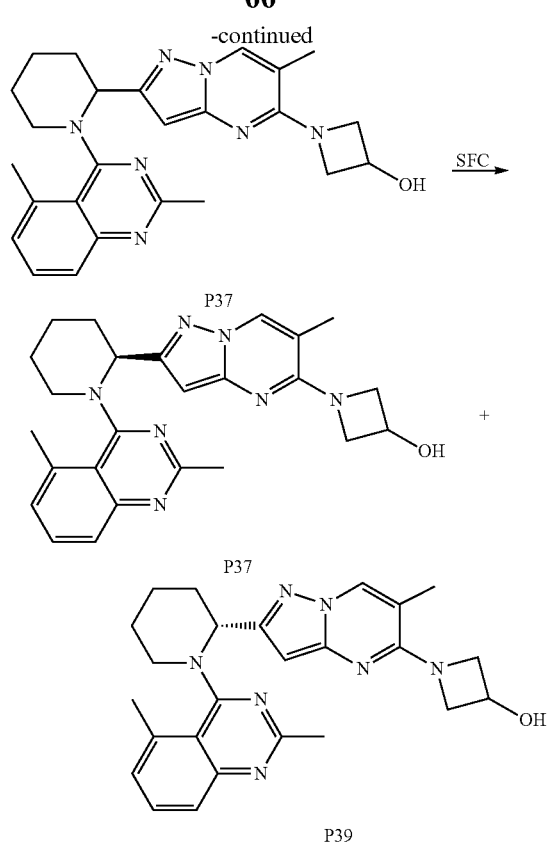

Step 1: synthesis of 4-(2-(5-chloro-6-methylpyrazolo[1,5-a]pyrimidin-2-yl)piperidin-1-yl)-2,5-dimethylquinazoline 50

To a solution of intermediate 19 (200 mg, 0.58 mmol) in 2-methoxyethanol (40 mL) was added 4-chloro-2, 5-dimethyl-quinazoline 40 (1 eq., 114 mg, 0.58 mmol, CAS nr. 147006-57-3) and DIPEA (3 eq., 0.3 mL, 1.7 mmol). The solution was heated to 80° C. for 16 hours. After cooling to room temperature the solution was concentrated in vacuum and purified by column chromatography eluting with a gradient starting from 0% to 10% MeOH in DCM. After evaporation the crude was triturated with diethyl ether to afford intermediate 50 (140 mg, 90% pure, 53% yield). The solid was used as such in the next step.
LCMS m/z=407 (M+H)+

Step 2: synthesis of 1-(2-(1-(2,5-dimethylquinazolin-4-yl)piperidin-2-yl)-6-methyl-pyrazolo[1,5-a]pyrimidin-5-yl)azetidin-3-ol P37

Intermediate 50 (140 mg, 0.31 mmol) was dissolved in 5 mL EtOH at room temperature. Then azetidin-3-ol hydrochloride (68 mg, 0.62 mmol) and DIPEA (0.16 mL, 0.92 mmol) were added. The resulting solution was refluxed for 16 hours. The mixture was then concentrated in vacuum and taken up in water/EtOH (3/1) the resulting solid was filtered off and dried into the oven to give compound P37 (65 mg, 48%).
LCMS m/z=444 (M+H)+
1H NMR (400 MHz, 420 K, DMSO-d6) δ ppm 1.41-1.70 (m, 3H) 1.76-1.89 (m, 1H) 2.12 (d, J=0.81 Hz, 3H) 2.23-2.33 (m, 2H) 2.49 (s, 3H) 2.75 (s, 3H) 3.53-3.64 (m, 2H) 3.94 (dd, J=9.69, 4.04 Hz, 2H) 4.36 (t, J=8.10 Hz, 2H) 4.48-4.56 (m, 1H) 5.74 (br. s., 1H) 5.79 (br. s., 1H) 7.27 (d, J=7.27 Hz, 1H) 7.43-7.54 (m, 1H) 7.55-7.63 (m, 1H) 8.12 (s, 1H)

Compound P37 (400 mg, 0.669 mmol) was purified by SFC to obtain the title compound, pure enantiomer P38 (44 mg):

$^1$H NMR (400 MHz, DMSO-d$_6$) δ ppm 1.47-1.77 (m, 4H) 1.86-2.00 (m, 1H) 2.13 (d, J=0.66 Hz, 3H) 2.25-2.43 (m, 4H) 2.50 (s, 3H) 3.32-3.46 (m, 1H) 3.92 (dd, J=9.79, 4.73 Hz, 2H) 4.20 (d, J=12.76 Hz, 1H) 4.28-4.42 (m, 2H) 4.43-4.57 (m, 1H) 5.65 (d, J=6.16 Hz, 1H) 5.78 (br. s, 1H) 5.96 (s, 1H) 7.56 (dd, J=8.80, 1.76 Hz, 1H) 7.60 (d, J=8.36 Hz, 1H) 7.76 (s, 1H) 8.45 (s, 1H)

and pure enantiomer P39 (55 mg):

$^1$H NMR (400 MHz, DMSO-d6) δ ppm 1.45-1.77 (m, 4H) 1.89-2.03 (m, 1H) 2.15 (s, 3H) 2.28-2.43 (m, 4H) 2.51 (br. s., 3H) 3.35-3.47 (m, 1H) 3.94 (dd, J=9.79, 4.73 Hz, 2H) 4.23 (d, J=12.76 Hz, 1H) 4.38 (t, J=8.80 Hz, 2H) 4.45-4.62 (m, 1H) 5.62 (br. s., 1H) 5.83 (br. s., 1H) 5.98 (s, 1H) 7.57 (dd, J=8.58, 1.32 Hz, 1H) 7.62 (d, J=8.58 Hz, 1H) 7.78 (s, 1H) 8.46 (s, 1H).

Synthesis of N-(4-(2-(5-(3-hydroxyazetidin-1-yl)-6-methylpyrazolo[1,5-a]-pyrimidin-2-yl)piperidin-1-yl)-5-methylquinazolin-2-yl)methanesulfonamide P41

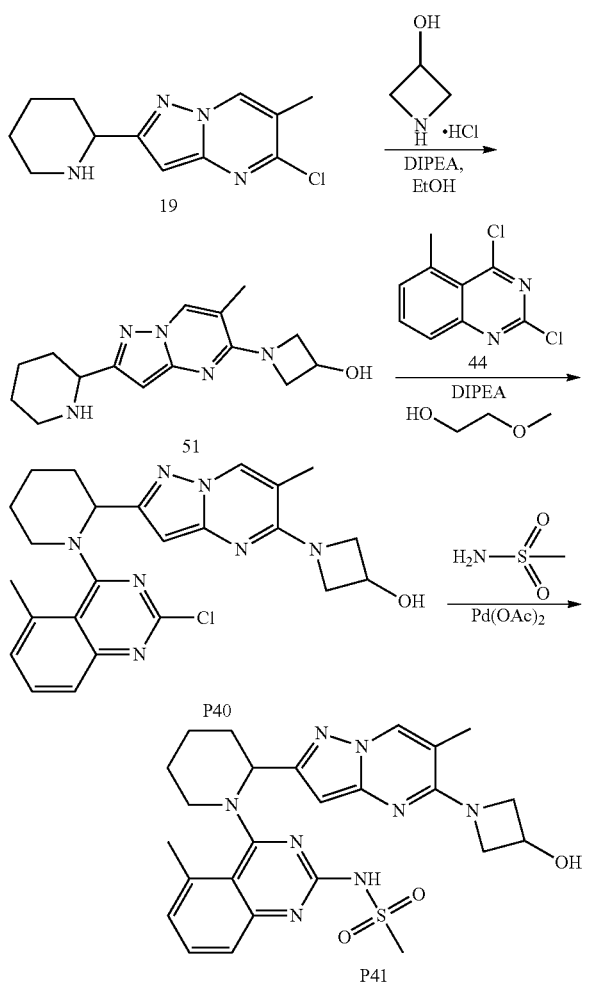

Step 1: synthesis of 1-(6-methyl-2-(piperidin-2-yl)pyrazolo[1,5-a]pyrimidin-5-yl)-azetidin-3-ol 51

To a solution of the intermediate 19 (4.1 g, 11.9 mmol) in EtOH (50 mL) was added azetidin-3-ol hydrochloride (1.04 g, 14.3 mmol, 1.2 eq.) and DIPEA (10.2 mL, 60 mmol, 5 eq.) and the solution was refluxed overnight. After cooling to ambient temperature, the solution was concentrated in vacuum. The crude was dissolved in DCM/MeOH (9/1) and the salts filtered off. The filtrate was concentrated in vacuum and purified via column chromatography (DCM/NH$_3$ (MeOH 7N): 9/1) to obtain intermediate 51 (1.9 g, 56%).

LCMS m/z=288 (M+H)$^+$ $^1$H NMR (400 MHz, DMSO-d$_6$) δ ppm 1.56-1.84 (m, 5H) 1.96-2.07 (m, 1H) 2.16 (d, J=0.88 Hz, 3H) 2.82-2.96 (m, 1H) 3.16-3.23 (m, 1H) 3.95 (dd, J=9.57, 4.95 Hz, 2H) 4.12 (dd, J=11.11, 2.97 Hz, 1H) 4.34-4.44 (m, 2H) 4.48-4.58 (m, 1H) 6.16 (s, 1H) 8.40 (s, 1H).

Step 2: synthesis of 1-(2-(1-(2-chloro-5-methylquinazolin-4-yl)piperidin-2-yl)-6-methylpyrazolo[1,5-a]pyrimidin-5-yl)azetidin-3-ol P40

To a solution of intermediate 51 (500 mg, 1.74 mmol) in 2-methoxyethanol (30 mL) was added 2, 4-dichloro-5-methylquinazoline 14 (1.2 eq., 808 mg, 2.08 mmol) and DIPEA (3 eq., 0.9 mL, 5.2 mmol). The solution was stirred at 50° C. during 2 hours and the mixture was concentrated in vacuum and extracted with DCM and washed with water. The combined organics were dried with MgSO$_4$ and concentrated in vacuum. The crude was further purified on HPLC to give the title product P40 (130 mg, 16%).

LCMS m/z=464 (M+H)$^+$ $^1$H NMR (400 MHz, DMSO-d$_6$) δ ppm 1.39-1.55 (m, 1H) 1.55-1.70 (m, 2H) 1.73-1.89 (m, 1H) 2.05-2.20 (m, 4H) 2.23-2.32 (m, 1H) 3.43-3.70 (m, 2H) 3.89-3.98 (m, 2H) 4.32-4.41 (m, 2H) 4.47-4.56 (m, 1H) 5.06-5.18 (m, 1H) 5.59-5.68 (m, 1H) 5.68-5.79 (m, 1H) 7.25-7.33 (m, 1H) 7.44-7.52 (m, 1H) 7.58-7.66 (m, 1H) 8.11-8.19 (m, 1H)

Step 3: synthesis of N-(4-(2-(5-(3-hydroxyazetidin-1-yl)-6-methylpyrazolo[1,5-a]-pyrimidin-2-yl)piperidin-1-yl)-5-methylquinazolin-2-yl)methanesulfonamide P41

To a solution of compound P40 (130 mg, 0.28 mmol) in 1,4-dioxane (5 mL) was added methanesulfonamide (2 eq., 53 mg, 0.56 mmol), cesium carbonate (2.5 eq., 0.7 mmol, 228 mg), 4,5-bis(diphenylphosphino)-9,9-dimethylxanthene (0.3 eq., 48.6 mg, 0.084 mmol) and Pd(OAc)$_2$ (0.3 eq., 18.87 mg, 0.084 mmol) in a sealed tube. The mixture was heated to 120° C. during 5 minutes in a microwave. The solution was filtered over dicalite, washed with dichloromethane and concentrated in vacuo. The crude was further purified by HPLC to give compound P41 (42 mg, 30%) as a white powder.

LCMS m/z=523 (M+H)$^+$ $^1$H NMR (400 MHz, 420 K, DMSO-d$_6$) δ ppm 1.46 (m, J=9.46 Hz, 1H) 1.62 (m, 2H) 1.80 (m, 1H) 2.07-2.18 (m, 4H) 2.24-2.36 (m, 1H) 2.63 (s, 3H) 2.97 (s, 3H) 3.57 (m, 1H) 3.68-3.80 (m, 1H) 3.90-3.98 (m, 2H) 4.33-4.41 (m, 2H) 4.45-4.59 (m, 1H) 5.05 (br. s., 1H) 5.82 (br. s., 1H) 5.94 (br. s., 1H) 7.05 (d, J=7.04 Hz, 1H) 7.22 (d, J=8.14 Hz, 1H) 7.47 (t, J=7.05 Hz, 1H) 8.16 (s, 1H) 9.88-11.04 (m, 1H).

Synthesis of 1-(2-(1-(2,6-dimethylquinazolin-4-yl)piperidin-2-yl)-6-methyl-pyrazolo[1,5-a]pyrimidin-5-yl)azetidin-3-ol P42

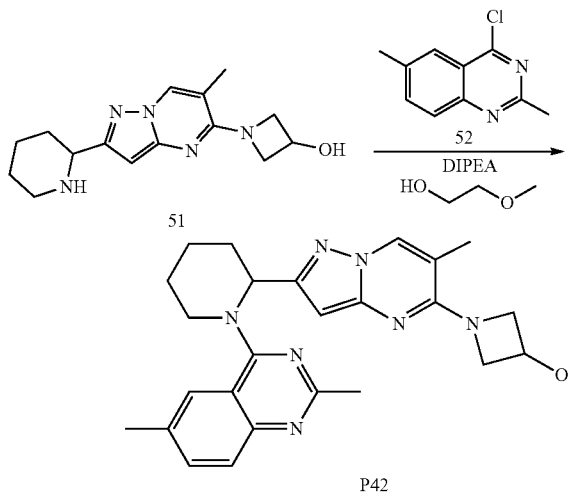

Synthesis of 4-chloro-2,6-dimethylquinazoline 52

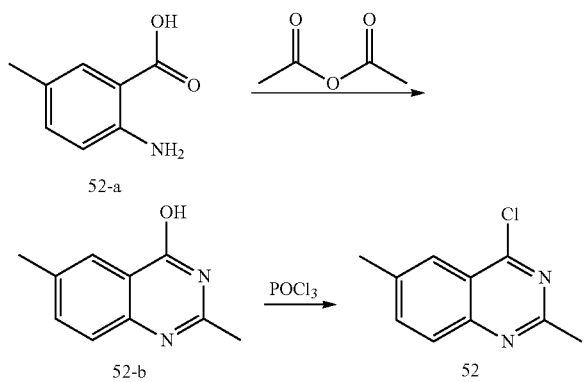

Step 1: synthesis of 2,6-dimethylquinazolin-4-ol 52-b 2-amino-5-methylbenzoic acid 52-a (8 g, 53 mmol) was dissolved in acetic anhydride (80 mL) and heated at 130° C. for 2 hours. The solution was then concentrated in vacuum to give the solid intermediate which was further dissolved in a solution of EtOH (100 mL) and NH3.H2O (80 mL) and heated to 80° C. After 48 hours, the solution was cooled and the solid filtered off and dried in the oven to give 2,6-dimethylquinazolin-4-ol 52-b (6.3 g, 70%).

LCMS m/z=175 (M+H)$^+$ $^1$H NMR (400 MHz, DMSO-d$_6$) δ ppm 2.32 (s, 3H) 2.41 (s, 3H) 7.46 (d, J=8.36 Hz, 1H) 7.56 (dd, J=8.14, 1.98 Hz, 1H) 7.76-7.92 (m, 1H) 11.91 (br. s, 1H)

Step 2: synthesis of 4-chloro-2,6-dimethylquinazoline 52

To a solution of 2,6-dimethylquinazolin-4-ol 52-b (500 mg, 2.87 mmol) in Toluene (10 mL) was added DIPEA (0.989 mL, 5.74 mmol, 2 eq.) and POCl$_3$ (0.4 mL, 4.3 mmol, 1.5 eq.). The solution was heated to 80° C. and stirred for 2 hours. The mixture was concentrated in vacuum and diluted with dichloromethane then washed with a saturated water solution of NaHCO$_3$. The combined organics were dried with MgSO$_4$, concentrated in vacuum and purified on column chromatography (Heptane/EtOAc: 1/1) to give intermediate 52 (300 mg, 90% purity, 48%).

LCMS m/z=193 (M+H)$^+$

Step 3: synthesis of 1-(2-(1-(2,6-dimethylquinazolin-4-yl)piperidin-2-yl)-6-methyl-pyrazolo[1,5-a]pyrimidin-5-yl)azetidin-3-ol P42

Intermediate 51 (240 mg, 0.83 mmol) was added to a solution of 4-chloro-2,6-dimethylquinazoline 52 (1.7 eq., 300 mg, 1.4 mmol) and DIPEA (3 eq. 0.43 mL, 2.5 mmol) in 2-methoxyethanol (5 mL). The solution was heated at 140° C. and stirred for 16 hours. After cooling to ambient temperature the mixture was extracted with DCM and washed with water. The combined organics were collected and dried with MgSO$_4$, filtered off and concentrated in vacuum. The crude was further purified by HPLC to give compound P42 (167 mg, 45%).

LCMS m/z=444 (M+H)$^+$ $^1$H NMR (400 MHz, DMSO-d$_6$) δ ppm 1.56-1.75 (m, 4H) 1.88-2.02 (m, 2H) 2.14 (s, 3H) 2.34 (s, 1H) 2.39 (s, 3H) 3.94 (dd, J=9.46, 5.28 Hz, 2H) 4.20 (d, J=12.76 Hz, 1H) 4.37 (t, J=8.10 Hz, 2H) 4.51 (br. s, 1H) 5.54-5.72 (m, 1H) 5.81 (br. s, 1H) 5.96 (s, 1H) 7.53-7.63 (m, 2H) 7.77 (s, 1H) 8.45 (s, 1H)

Synthesis of (S)-1-(2-(1-(2,6-dimethylquinazolin-4-yl)piperidin-2-yl)-6-methyl-pyrazolo[1,5-a]pyrimidin-5-yl)azetidin-3-ol P43 and (R)-1-(2-(1-(2,6-dimethyl-quinazolin-4-yl)piperidin-2-yl)-6-methylpyrazolo[1,5-a]pyrimidin-5-yl)azetidin-3-ol P44

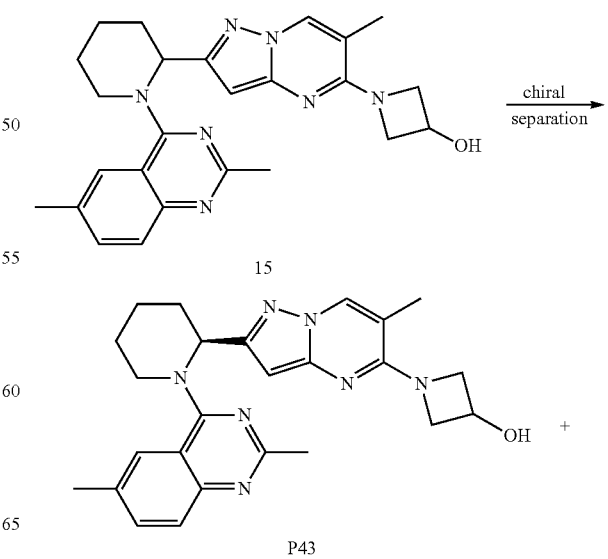

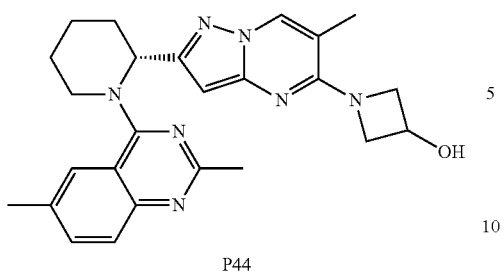

P44

A further purification was performed via Prep SFC (stationary phase: chiralpak Diacel AS 20×250 mm, Mobile phase: $CO_2$, EtOH with 0.2% iPrNH$_2$) giving both relative entiomers:

P43:
LCMS m/z=444 (M+H)
$^1$H NMR (400 MHz, DMSO-d$_6$) δ ppm 1.68 (s, 4H) 1.89-2.03 (m, 1H) 2.15 (s, 3H) 2.28-2.43 (m, 4H) 2.51 (br. s., 3H) 3.35-3.47 (m, 1H) 3.94 (dd, J=9.79, 4.73 Hz, 2H) 4.23 (d, J=12.76 Hz, 1H) 4.38 (t, J=8.80 Hz, 2H) 4.45-4.62 (m, 1H) 5.62 (br. s, 1H) 5.83 (br. s., 1H) 5.98 (s, 1H) 7.57 (dd, J=8.58, 1.32 Hz, 1H) 7.62 (d, J=8.58 Hz, 1H) 7.78 (s, 1H) 8.46 (s, 1H)

P44:
LCMS m/z=444 (M+H)
$^1$H NMR (400 MHz, DMSO-d$_6$) δ ppm 1.47-1.77 (m, 4H) 1.86-2.00 (m, 1H) 2.13 (d, J=0.66 Hz, 3H) 2.25-2.43 (m, 4H) 2.50 (s, 3H) 3.32-3.46 (m, 1H) 3.92 (dd, J=9.79, 4.73 Hz, 2H) 4.20 (d, J=12.76 Hz, 1H) 4.28-4.42 (m, 2H) 4.43-4.57 (m, 1H) 5.65 (d, J=6.16 Hz, 1H) 5.78 (br. s, 1H) 5.96 (s, 1H) 7.56 (dd, J=8.80, 1.76 Hz, 1H) 7.60 (d, J=8.36 Hz, 1H) 7.76 (s, 1H) 8.45 (s, 1H)

P43: $[α]_D^{20}$=+295.23° (589 nm, c=0.377 w/v %, DMF, 20° C.)

P44: $[α]_D^{20}$=−269.05° (589 nm, c=0.378 w/v %, DMF, 20° C.)

Synthesis of 4-(2-(5-(azetidin-1-yl)-7-morpholinopyrazolo[1,5-a]pyrimidin-2-yl)-piperidin-1-yl)-5-methylquinazolin-2-ol P45

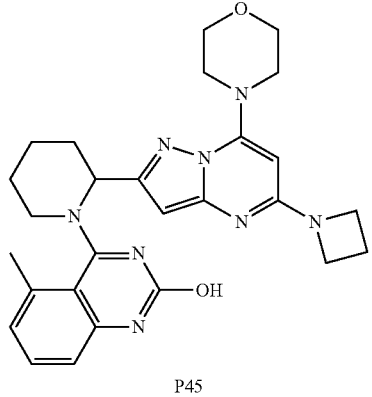

P45

A solution of intermediate 15 (100 mg, 0.193 mmol) in acetic acid (2 mL) was warmed to 70° C. for 3 hours. The reaction mixture was allowed to cool down to room temperature and water was added. The resulting mixture was diluted with dichloromethane and washed with aqueous solution of sodium bicarbonate. The organic layers were dried over MgSO4 and the solvent was evaporated to yield product P45 (80 mg, 80%).

m/z=501.6 (M+H)$^+$

MP=223.59° C.

$^1$H NMR at 100° C. (400 MHz, DMSO-d$_6$) δ ppm 10.31 (br. s., 1H), 7.35 (t, J=7.7 Hz, 1H), 7.02 (d, J=8.1 Hz, 1H), 6.90 (d, J=7.5 Hz, 1H), 6.24-5.34 (m, 2H), 5.24 (s, 1H), 4.10-3.43 (m, 14H), 2.65 (s, 3H), 2.37-2.06 (m, 4H), 1.89-1.39 (m, 4H)

Synthesis of 4-(2-(5-(azetidin-1-yl)-7-morpholinopyrazolo[1,5-a]pyrimidin-2-yl)-piperidin-1-yl)-5-methylquinazoline-2-carboxamide P46

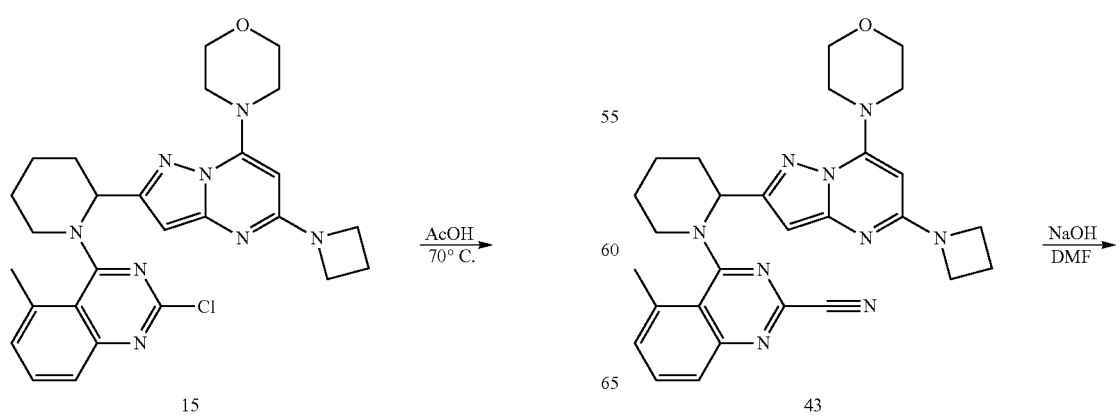

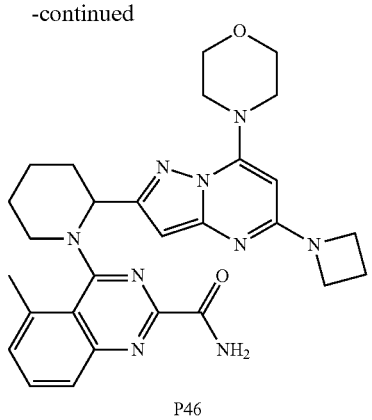

P46

To a solution of intermediate 43 (100 mg, 0.17 mmol) in DMF (5 mL) was added 10 mL NaOH (1M in H₂O) in a sealed tube. The solution was heated to 130° C. for 10 minutes in a microwave. The solution was then adjusted to pH=6-7 with 1 molar aqueous solution of hydrochloric acid. The solution was further extracted with DCM, and the combined organics were washed with a saturated NaHCO₃ solution and brine. The organic layer was further dried with MgSO4 and concentrated in vacuum. The resulting material was purified on HPLC to compound P46 (68 mg, 73%)

LCMS m/z=528 (M+H)⁺

¹H NMR (400 MHz, DMSO-d₆) δ ppm 1.14-1.87 (m, 4H) 1.98-2.41 (m, 4H) 2.84 (s, 3H) 3.19-3.27 (m, 2H) 3.40-3.83 (m, 7H) 3.85-4.28 (m, 5H) 5.12-5.44 (m, 2H) 5.87 (s, 1H) 7.38-7.50 (m, 1H) 7.55-7.81 (m, 3H) 7.89-8.03 (m, 1H).

Synthesis of 4-(5-cyclopropyl-6-methyl-2-(1-(5-methylquinazolin-4-yl)piperidin-2-yl)pyrazolo[1,5-a]pyrimidin-7-yl)morpholine P47

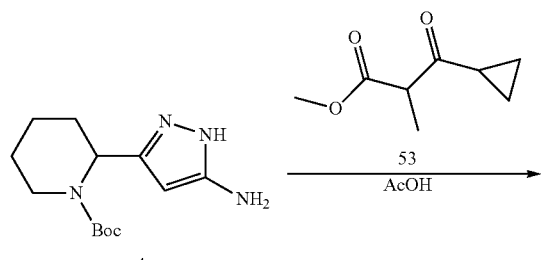

4

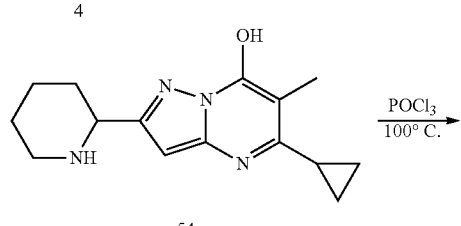

54

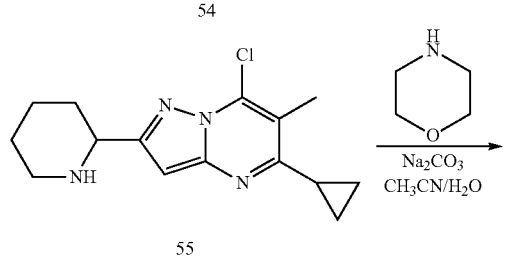

55

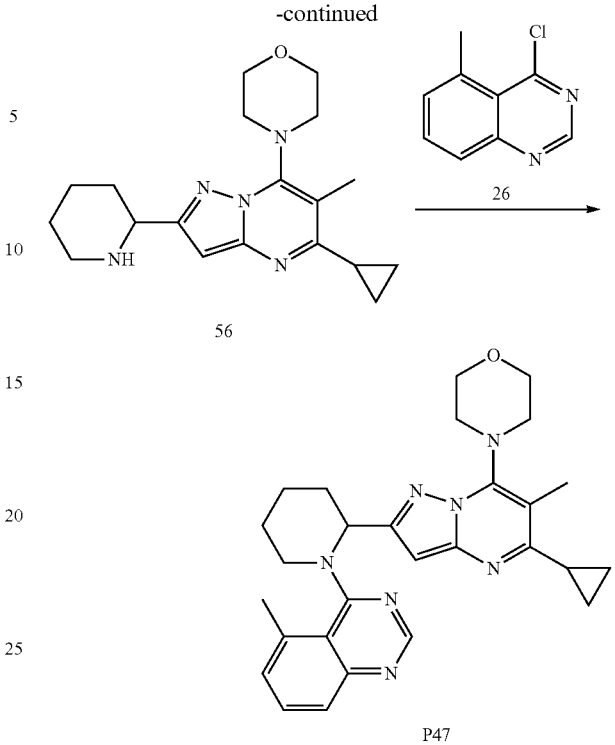

P47

Step 1: synthesis of 5-cyclopropyl-6-methyl-2-(piperidin-2-yl)pyrazolo[1,5-a]-pyrimidin-7-ol 54

To a solution of intermediate 4 (16 g, 60 mmol) in acetic acid (100 mL) was added methyl 3-cyclopropyl-2-methyl-3-oxopropanoate 53 (30 g, 180 mmol). The resulting mixture was stirred at 100° C. overnight.

The resulting mixture was concentrated under vacuum and the residue (46 g, 98%) was used as such in the next step.

Step 2: synthesis of 7-chloro-5-cyclopropyl-6-methyl-2-(piperidin-2-yl)pyrazolo-[1,5-a]pyrimidine 55

The mixture of intermediate 54 (45 g, 79 mmol) and phosphoryl trichloride (220 g) was stirred at 110° C. for one hour. The solvent was removed and the residue was dissolved in ice watered solution and basified by addition of sodium carbonate (19.8 g, 238 mmol). This solution was used as such in the next step.

Step 3: synthesis of 4-(5-cyclopropyl-6-methyl-2-(piperidin-2-yl)pyrazolo[1,5-a]-pyrimidin-7-yl)morpholine 56

To the solution of intermediate 55 acetonitrile (250 mL) and morpholine (20.7 g, 238 mmol) were added. The resulting mixture was refluxed overnight. The reaction mixture was allowed to cool down to room temperature and the solvent was removed under vacuum. The resulting water solution was extracted with dichloromethane and the organic layers were dried over Na2SO4 and concentrated. The residue was purified by column chromatography using dichloromethane and methanol as eluent. Intermediate 56 (2 g, 7%) was isolated.

Step 4: synthesis of 4-(5-cyclopropyl-6-methyl-2-(1-(5-methylquinazolin-4-yl)-piperidin-2-yl)pyrazolo[1,5-a]pyrimidin-7-yl)morpholine P47

To a solution intermediate 56 (200 mg, 0.56 mmol) in 5 mL 2-methoxyethanol was added 4-chloro-5-methyl-quinazoline 26 (1.2 eq., 126 mg, 0.67 mmol) and DIPEA (3 eq., 0.289 mL, 1.68 mmol). The solution was stirred at 80° C. for 48 hours. After cooling to room temperature the solution was concentrated in vacuo and purified on HPLC to give the title product P47 (110 mg, 41%).

LCMS m/z=484 (M+H)$^+$ $^1$H NMR (400 MHz, 420 K, DMSO-d$_6$) δ ppm 0.90-1.11 (m, 4H) 1.50-1.61 (m, 1H) 1.61-1.76 (m, 2H) 1.80-1.92 (m, 1H) 2.07-2.18 (m, 1H) 2.20-2.32 (m, 2H) 2.35 (s, 3H) 2.84 (s, 3H) 3.28-3.40 (m, 4H) 3.47-3.65 (m, 2H) 3.66-3.78 (m, 4H) 5.56-5.67 (m, 1H) 6.00 (br. s., 1H) 7.30 (d, J=6.46 Hz, 1H) 7.55-7.66 (m, 2H) 8.46 (s, 1H)

Synthesis of (3 S)-1-(6-methyl-2-(1-(5-methylquinazolin-4-yl)piperidin-2-yl)-pyrazolo[1,5-a]pyrimidin-5-yl)pyrrolidin-3-amine P48

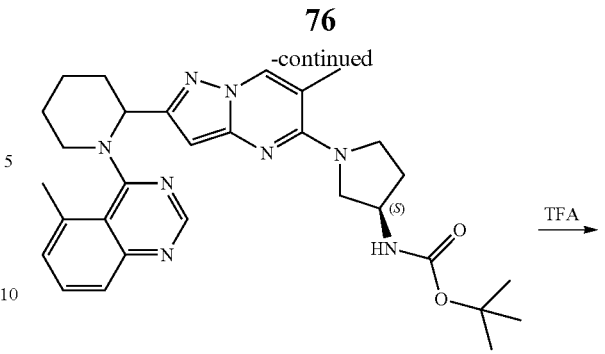

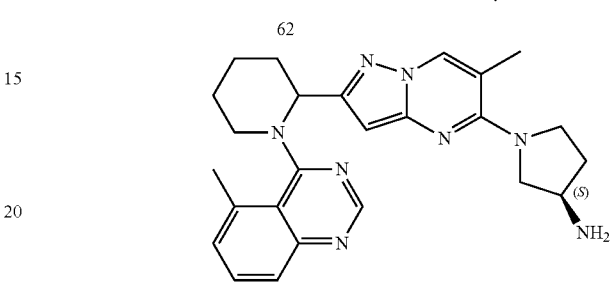

P48

Step 1: synthesis of tert-butyl 2-(5-hydroxy-6-methylpyrazolo[1,5-a]pyrimidin-2-yl)-piperidine-1-carboxylate 58

To a solution of intermediate 4 (14.43 g, 54.18 mmol) in DMF (270 ml), (E)-ethyl 3-ethoxy-2-methylacrylate 57 (9.00 g, 56.9 mmol) and Cs$_2$CO$_3$ (26.48 g, 81.27 mmol) were added. The resulting mixture was stirred at 130° C. for 12 hours. The solvent was evaporated under vacuum. The residue was successively dissolved in ethyl acetate (300 ml), washed with saturated aqueous NH$_4$Cl solution, with brine and dried over Na$_2$SO$_4$. After filtration, the filtrate was concentrated under vacuum to 100 ml. After 16 hours, the precipitate was filtered off. The filter cake was washed with ethyl acetate (2×30 ml) and dried (vacuum, 45° C., 1 hour) to give intermediate 58 (11.80 g, 65.52%).

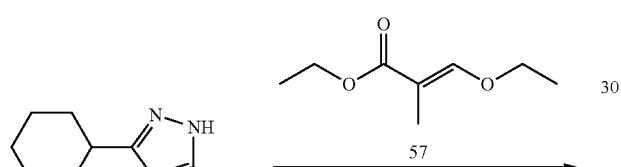

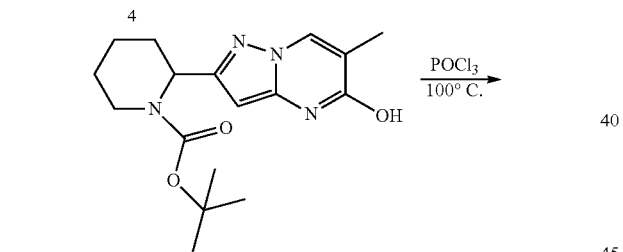

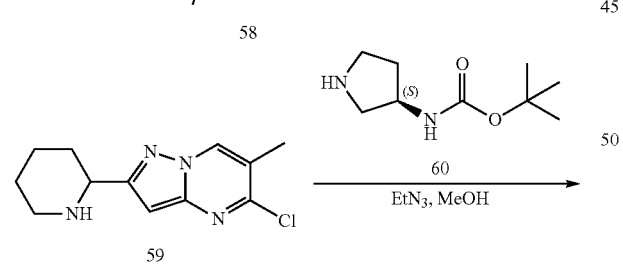

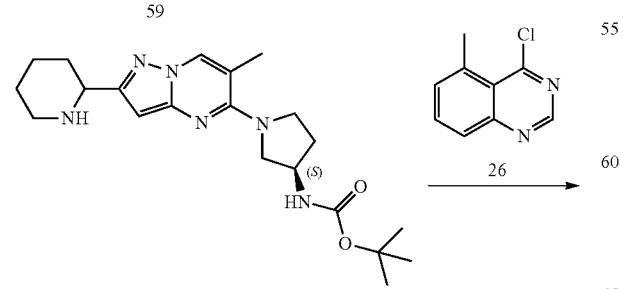

Step 2: synthesis of 5-chloro-6-methyl-2-(piperidin-2-yl)pyrazolo[1,5-a]pyrimidine 59

A mixture of intermediate 58 (11.80 g, 35.50 mmol) in phosphoryl trichloride (178 ml) was stirred at 80° C. for 1 hour. The solvent was evaporated under vacuum. The residue was dissolved in acetonitrile (200 ml). The mixture was neutralized with ammonia (7 M in methanol) to pH=7-8. The precipitate was filtered off and the filtrate was concentrated. The residue was purified by flash column chromatography over silica gel (eluent: dichloromethane/1% NH$_3$ in methanol 10/1). The collected fractions were concentrated to give intermediate 59 (3.715 g, 40.44%).

Step 3: synthesis of tert-butyl((3 S)-1-(6-methyl-2-(piperidin-2-yl)pyrazolo[1,5-a]-pyrimidin-5-yl)pyrrolidin-3-yl)carbamate 61

The solution of intermediate 59 (3.58 g, 10.0 mmol, 70% purity), (S)-tert-butyl-pyrrolidin-3-ylcarbamate 60 (2.33 g, 12.5 mmol) and Et₃N (3.04 g, 30.0 mmol) in MeOH (50 ml) was stirred overnight at 70° C. The mixture was filtered and the filtrate was concentrated under vacuum. The residue was dissolved in CH₂Cl₂ and washed with brine. The separated organic layer was dried over Na₂SO₄, filtered and concentrated under vacuum. The residue was purified by silica column chromatography (eluent: CH₂Cl₂/MeOH 10:1). After concentration, the crude product was triturated with CH₃CN. The solid was filtered and washed with CH₃CN to give the title intermediate 62 (768 mg, 12% yield)

¹H NMR (400 MHz, CDCl₃) δ ppm 1.45 (s, 9H) 1.62 (m, 1H) 1.90 (m, 3H) 2.16 (m, 3H) 2.26 (s, 3H) 3.12 (m, 1H) 3.47 (m, 1H) 3.49 (s, 3H) 3.65 (m, 1H) 3.72 (m, 1H) 3.84 (m, 1H) 4.26 (m, 1H) 4.37 (m, 1H) 4.90 (d, 1H, J=6.8 Hz) 6.39 (s, 1H) 7.99 (d, 1H, J=4.8 Hz).

Step 4: synthesis of tert-butyl((3 S)-1-(6-methyl-2-(1-(5-methylquinazolin-4-yl)-piperidin-2-yl)pyrazolo[1,5-a]pyrimidin-5-yl)pyrrolidin-3-yl)carbamate 62

The intermediate 61 (300 mg, 0.694 mmol), 4-chloro-5-methyl-quinazoline 26 (170 mg, 0.902 mmol) and Hunig's base (395 µl, 2.291 mmol) were mixed in 2-methoxyethanol (4.7 ml) and heated at 80° C. for 2 hours. After cooling to room temperature, the reaction mixture was added slowly to iced water solution. The suspension was stirred at room temperature for 2 hours. The formed precipitate was filtered off, washed with water and then dried in the vacuum oven for 16 hours. The crude was purified by column chromatography by eluting with a gradient starting with 100% DCM to 10% MeOH and 90% DCM. After evaporation of the pure fractions we get crude of the title intermediate 62 (238 mg)

m/z=543.4 (M+H)⁺

Step 5: synthesis of (3S)-1-(6-methyl-2-(1-(5-methylquinazolin-4-yl)piperidin-2-yl)pyrazolo[1,5-a]pyrimidin-5-yl)pyrrolidin-3-amine P48

Intermediate 62 (238 mg, 0.386 mmol), was dissolved in DCM (2.5 ml) and trifluoroacetic acid (295 µl, 3.859 mmol) was added. The mixture was stirred at room temperature for 16 hours. The reaction mixture was added drop wise to a cooled saturated solution of NaHCO₃. The product was extracted with DCM (3 times). The organic layers were dried over Na₂SO₄, filtered and evaporated to dryness. The crude was purified by column chromatography by eluting with a gradient starting with 100% DCM to 10% (MeOH/NH₃) and 90% DCM. After evaporation of the pure fractions a yellow foam was isolated. The foam was triturated in diethyl ether to get the title product P48 as a white solid (152 mg, 85%).

¹H NMR (400 MHz, DMSO-d₆) δ ppm 8.46 (s, 1H), 8.15 (s, 1H), 7.68-7.51 (m, 2H), 7.29 (d, J=6.4 Hz, 1H), 5.79-5.42 (m, 2H), 3.85-3.19 (m, 7H), 2.80-2.75 (m, 3H), 2.28 (s, 3H), 2.25-1.28 (m, 8H)

m/z=443.3 (M+H)⁺

MP=124.92° C.

Synthesis of (3S)-1-(2-(1-(6-methylquinazolin-4-yl)piperidin-2-yl)pyrazolo[1,5-a]pyrimidin-5-yl)pyrrolidin-3-amine P49

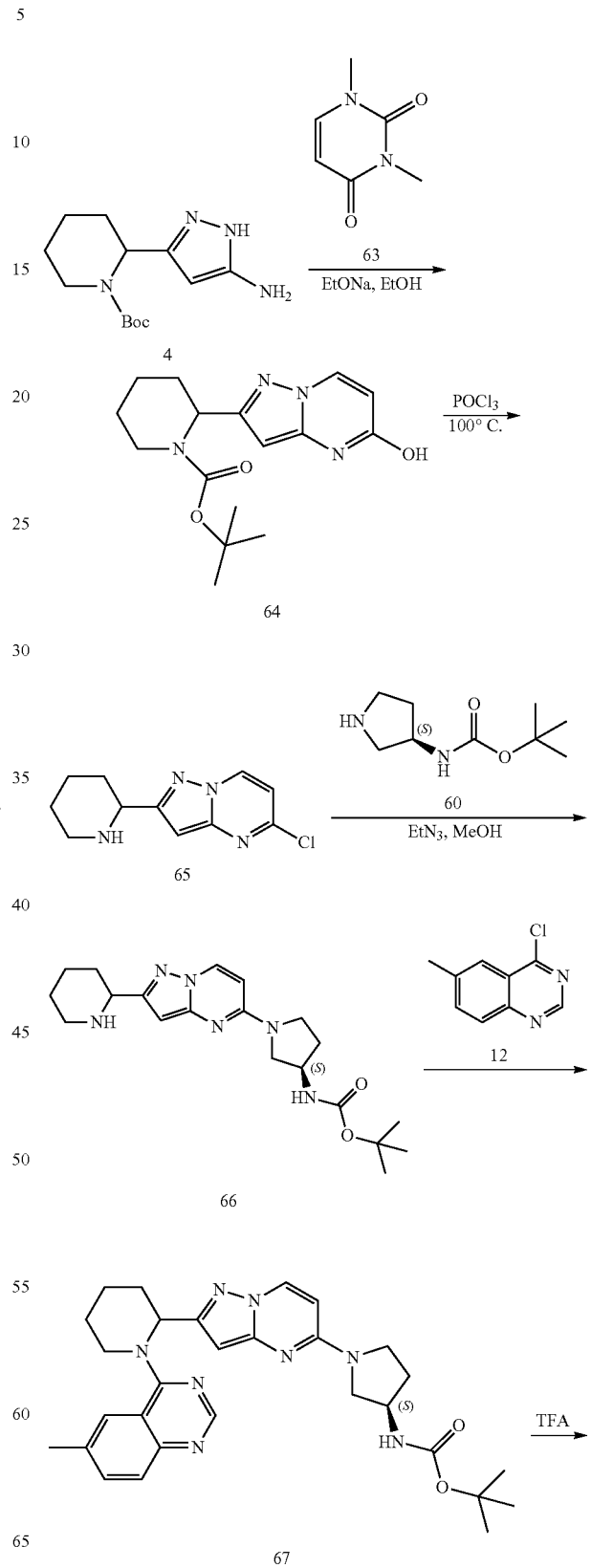

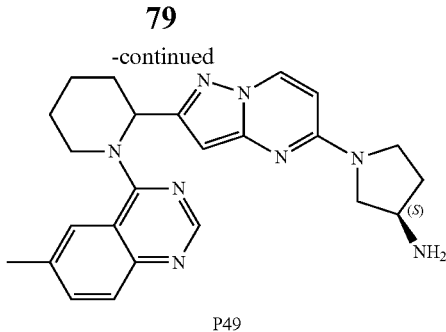

P49

Step 1: synthesis of tert-butyl 2-(5-hydroxypyrazolo [1,5-a]pyrimidin-2-yl)piperidine-1-carboxylate 64

To a solution of intermediate 4 (5.00 g, 18.8 mmol) and 1,3-dimethylpyrimidine-2,4(1H,3H)-dione 63 (2.90 g, 20.7 mmol) in ethanol (50 mL) sodium ethoxide (22 ml, 66 mmol) was added. The resulting solution was refluxed overnight. The solvent was evaporated under vacuum. Water was added to the residue and the pH was adjusted to 4-5 with HCl (1 N). The mixture was extracted with ethyl acetate, the organic layer was washed with brine, dried over $Na_2SO4$, filtered and concentrated under vacuum to give the crude intermediate 64 (5 g, 75%).

Step 2: synthesis of 5-chloro-2-(piperidin-2-yl)pyrazolo[1,5-a]pyrimidine 65

A mixture of intermediate 64 (5 g, 15.7 mmol) in $POCl_3$ (50 ml) was stirred at 100° C. for 2 hours. The solvent was evaporated under vacuum. The residue was washed with tert-butylmethyl ether to yield intermediate 65 (4.5 g, 19 mmol).

Step 3: synthesis of tert-butyl((3S)-1-(2-(piperidin-2-yl)pyrazolo[1,5-a]pyrimidin-5-yl)pyrrolidin-3-yl)carbamate 66

A mixture of intermediate 65 (4.5 g, 19 mmol), (S)-tert-butylpyrrolidin-3-ylcarbamate 60 (7.0 g, 38 mmol) and triethylamine (7.7 g, 76 mmol) in methanol (50 ml) was refluxed overnight. The mixture was filtered and the filtrate was concentrated under vacuum. The residue was dissolved in $CH_3CN$ and stirred with $K_2CO_3$ (5.0 g, 38 mmol). The mixture was filtered and the filtrate was concentrated under vacuum. The residue was treated with $H_2O$ and $CH_2Cl_2$. The separated organic layer was dried over $Na_2SO_4$, filtered and concentrated under vacuum to give intermediate 66 (1.65 g, 22%).

$^1$H NMR (400 MHz, $CDCl_3$) δ ppm 1.45 (s, 9H) 1.51-1.72 (m, 1H) 1.83-1.93 (m, 2H) 1.94-2.07 (m, 3H) 2.20-2.39 (m, 1H) 2.73-2.93 (m, 1H) 3.11-3.28 (m, 1H) 3.35-3.49 (m, 1H) 3.53-3.74 (m, 1H) 3.75-3.95 (m, 1H) 4.24-4.45 (m, 1H) 4.59-4.90 (m, 1H) 5.96-6.19 (m, 1H) 8.12-8.30 (m, 1H).

Step 4: synthesis of tert-butyl((3S)-1-(2-(1-(6-methylquinazolin-4-yl)piperidin-2-yl)-pyrazolo[1,5-a]pyrimidin-5-yl)pyrrolidin-3-yl)carbamate 67

Intermediate 66 (250 mg, 0.624 mmol), 4-chloro-6-methylquinazoline 12 (145 mg, 0.811 mmol) and DIPEA (355 µl, 2.058 mmol) were mixed in 2-methoxyethanol (4.2 ml) and heated at 80° C. for 16 hours and at 90° C. for 1 hour. After cooling to room temperature, the reaction mixture was added slowly to iced water. The suspension was stirred at room temperature overnight. The brown precipitate was filtered off, washed with water and then dried in the vacuum oven for 16 hours. The crude of the title intermediate 67 (250 mg) was used as such in the next step.

m/z=529.4 $(M+H)^+$

Step 5: synthesis of (3S)-1-(2-(1-(6-methylquinazolin-4-yl)piperidin-2-yl)pyrazolo-[1,5-a]pyrimidin-5-yl)pyrrolidin-3-amine P49

Intermediate 67 (250 mg, 0.473 mmol) was dissolved in DCM (3.0 ml) and TFA (362 µl, 4.729 mmol) was added. The reaction mixture was stirred at room temperature for 16 hours. The reaction mixture was quenched with saturated $Na_2CO_3$ solution and the product was extracted 3 times with DCM. The organic layers were evaporated and the product was purified by column chromatography by eluting with a gradient starting with 100% DCM to 10% (MeOH/$NH_3$) and 90% DCM. After evaporation of the pure fractions we get the desired product P49 as a yellow foam (122 mg, 56%).

m/z=429.3 $(M+H)^+$ $^1$H NMR (400 MHz, DMSO-$d_6$) δ ppm 8.63-8.53 (m, 2H), 7.82 (br. s, 1H), 7.71 (d, J=8.6 Hz, 1H), 7.63 (dd, J=1.5, 8.6 Hz, 1H), 6.30 (d, J=7.7 Hz, 1H), 5.91 (s, 1H), 5.84-5.77 (m, 1H), 4.29-4.17 (m, 1H), 3.72-2.99 (m, 6H), 2.47-1.58 (m, 13H)

$^1$H NMR at 100° C. (400 MHz, DMSO-$d_6$) δ ppm 8.52 (s, 1H), 8.42 (dd, J=0.7, 7.7 Hz, 1H), 7.86-7.81 (m, 1H), 7.68 (d, J=8.8 Hz, 1H), 7.58 (dd, J=1.8, 8.6 Hz, 1H), 6.24 (d, J=7.7 Hz, 1H), 5.86 (s, 1H), 5.84-5.79 (m, 1H), 4.26-4.18 (m, 1H), 3.66-3.43 (m, 5H), 3.19-3.12 (m, 1H), 2.42 (s, 3H), 2.40-2.30 (m, 1H), 2.14-1.92 (m, 3H), 1.86-1.59 (m, 6H)

Synthesis of (S)-1-(2-((R)-1-(6-methylquinazolin-4-yl)piperidin-2-yl)pyrazolo-[1,5-a]pyrimidin-5-yl)pyrrolidin-3-amine P50

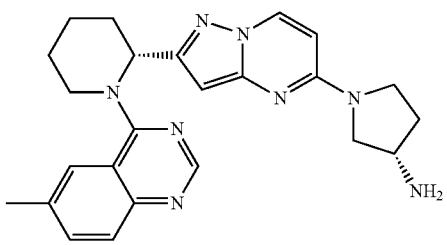

P50

Product P49 (100 mg, 0.233 mmol) was purified by SFC to obtain the title compound, pure enantiomer, as an off white solid P50 (51 mg, 51%).

SFC: 100% pure at $R_t$=2.64 min m/z=429.2 $(M+H)^+$

P50: $[α]_D^{20}$=−268.64° (589 nm, c=0.354 w/v %, DMF, 20° C.)

81

Synthesis of (S)-1-(2-((S)-1-(6-methylquinazolin-4-yl)piperidin-2-yl)pyrazolo-[1,5-a]pyrimidin-5-yl)pyrrolidin-3-amine P51

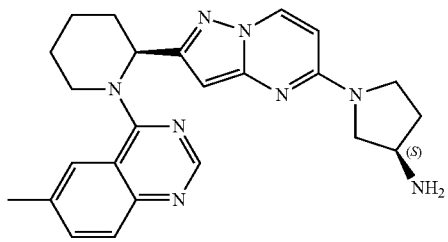

Product P49 (100 mg, 0.233 mmol) was purified by SFC to obtain the title compound, pure enantiomer, as an off white solid P51 (17 mg, 17%).

SFC: 100% pure at $R_t$=3.68 min m/z=429.3 (M+H)$^+$

Synthesis of tert-butyl4-(5-(azetidin-1-yl)-2-(1-(5-methylquinazolin-4-yl)piperidin-2-yl)pyrazolo[1,5-a]pyrimidin-7-yl)piperazine-1-carboxylate P52

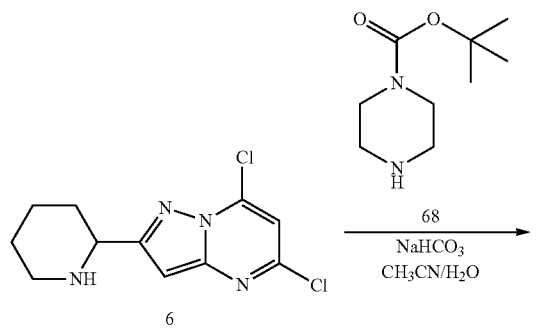

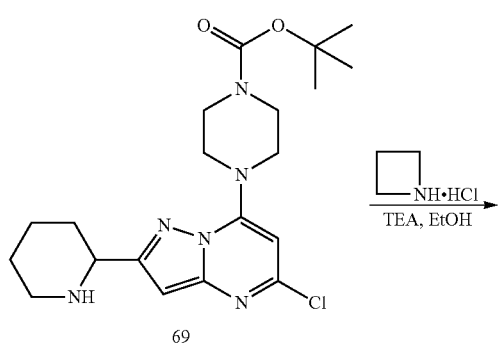

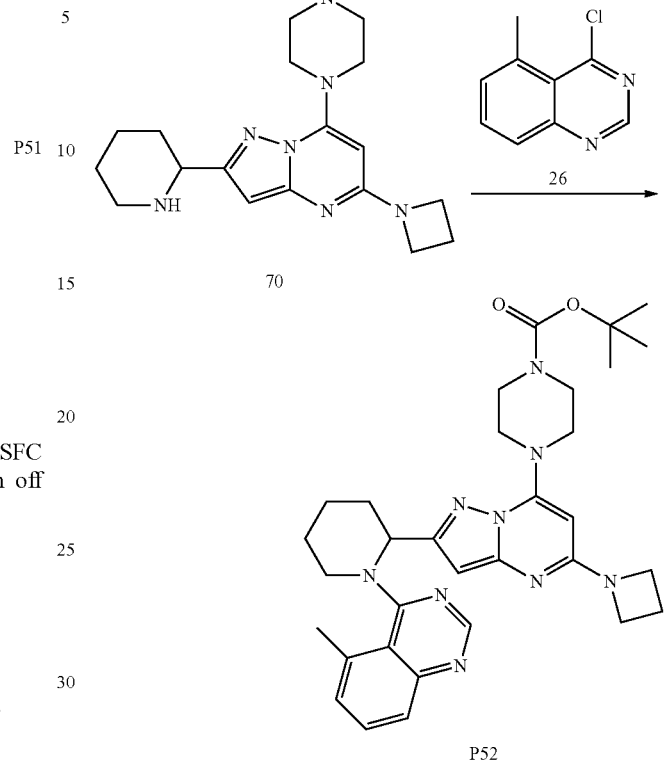

Step 1: synthesis of tert-butyl4-(5-chloro-2-(piperidin-2-yl)pyrazolo[1,5-a]pyrimidin-7-yl)piperazine-1-carboxylate 69

A mixture of intermediate 6 (40.0 g, 125 mmol), tert-butylpiperazine-1-carboxylate 68 (25.7 g, 138 mmol) and NaHCO$_3$ (26.30 g, 313.5 mmol) in CH$_3$CN (300 ml) and H$_2$O (300 ml) was stirred at room temperature for 1 hours. The solvent was concentrated under vacuum. The concentrate was treated with CH$_2$Cl$_2$ (500 ml). The separated organic layer was washed with brine (200 ml), filtered and concentrated under vacuum to afford the title intermediate 69 (40 g, yield: 68%).

Step 2: synthesis of tert-butyl4-(5-(azetidin-1-yl)-2-(piperidin-2-yl)pyrazolo[1,5-a]-pyrimidin-7-yl)piperazine-1-carboxylate 70

A mixture of intermediate 69 (40 g, 95 mmol), azetidine hydrochloride (47.7 g, 510 mmol) and TEA (155.0 g, 1530 mmol) in ethanol (500 ml) was refluxed overnight. The mixture was filtered and the filtrate was concentrated under vacuum. The residue was treated with CH$_2$Cl$_2$ and H$_2$O. The separated organic layer was concentrated under vacuum. The residue was purified by column chromatography over silica gel (eluent: dichloromethane/methanol (1% of TEA contained)=15/1). The product fractions were collected and the solvent was evaporated to afford the title intermediate 70 (17.96 g, yield 42.71%).

m/z=515 (M+H)$^+$ $^1$H NMR (400 MHz, CDCl$_3$) δ ppm 1.49 (s, 9H) 1.52-1.68 (m, 4H) 1.91-2.05 (m, 4H) 2.37-2.41 (m, 2H) 2.78-2.83 (m, 1H) 3.16-3.18 (m, 1H) 3.51-3.53 (m, 4H) 3.67-3.68 (m, 4H) 3.79-3.82 (m, 1H) 4.09-4.4.13 (m, 4H) 5.10 (s, 1H) 6.04 (s, 1H).

Step 3: synthesis of tert-butyl4-(5-(azetidin-1-yl)-2-(1-(5-methylquinazolin-4-yl)-piperidin-2-yl)pyrazolo[1,5-a]pyrimidin-7-yl)piperazine-1-carboxylate P52

The mixture of intermediate 70 (3 g, 5.83 mmol), intermediate 26 (1.56 g, 8.75 mmol) was dissolved in 2-methoxyethanol (100 mL) then diisopropylethyl amine (2 mL, 11.66 mmol) was added. The resulting mixture was stirred at 50° C. for three days. The mixture was allowed to cool down to room temperature and poured in iced watered solution. The resulting mixture was stirred until all the ice is melt then the resulting solid was filtered off. The solid was successively washed with water, dissolved in dichloromethane, dried over MgSO4 and concentrated. The resulting residue was purified by column chromatography using dichloromethane and methanol to yield P52 (3.3 g, 87%) as a white light yellow solid.

m/z=584 (M+H)+

$^1$H NMR (400 MHz, DMSO-d6) δ ppm 1.39-1.49 (m, 9H), 1.53-1.91 (m, 4H), 2.03-2.36 (m, 4H), 2.87 (s, 3H), 3.29-3.51 (m, 8H), 3.53-3.67 (m, 4H), 3.90-4.04 (m, 2H), 5.40-5.51 (m, 1H), 5.64 (s, 1H), 6.25 (br. s., 1H), 7.27-7.42 (m, 1H), 7.52-7.70 (m, 2H), 8.47 (s, 1H).

Synthesis of 4-(2-(5-(azetidin-1-yl)-7-(piperazin-1-yl)pyrazolo[1,5-a]pyrimidin-2-yl)piperidin-1-yl)-5-methylquinazoline P53

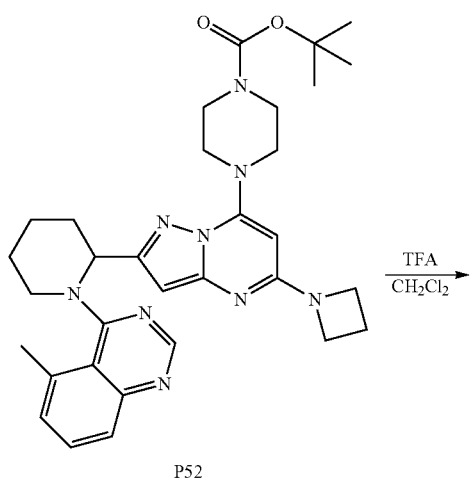

P52

P53

Compound P52 (3 g, 5.139 mmol) was dissolved in DCM (150 ml) and TFA (4 ml, 51 mmol) was added. The reaction mixture was stirred at room temperature for 5 days. The reaction mixture was quenched with saturated Na$_2$CO$_3$ solution and the product was extracted 3 times with DCM. The organic layers were evaporated and the product was purified by column chromatography by eluting with a gradient starting with 100% DCM to 10% (MeOH/NH$_3$) and 90% DCM. After evaporation of the concerning fractions we get the desired product P53 as a yellow foam (2.3 g, 92%).

m/z=484 (M+H)+

$^1$H NMR (400 MHz, DMSO-d$_6$) δ ppm 1.57 (br. s., 1H), 1.63-1.76 (m, 2H), 1.80-1.95 (m, 1H), 2.15-2.27 (m, 2H), 2.32 (quin, J=7.4 Hz, 2H), 2.90-3.08 (m, 5H), 3.42-3.67 (m, 7H), 3.77-3.96 (m, 1H), 4.02 (t, J=7.4 Hz, 4H), 5.20 (s, 1H), 5.52 (br. s., 1H), 5.63 (s, 1H), 7.28-7.39 (m, 1H), 7.57-7.68 (m, 2H), 8.49 (s, 1H)

Synthesis of 4-(5-(azetidin-1-yl)-2-(1-(5-methylquinazolin-4-yl)piperidin-2-yl)-pyrazolo[1,5-a]pyrimidin-7-yl)-N-isopropylpiperazine-1-carboxamide P54

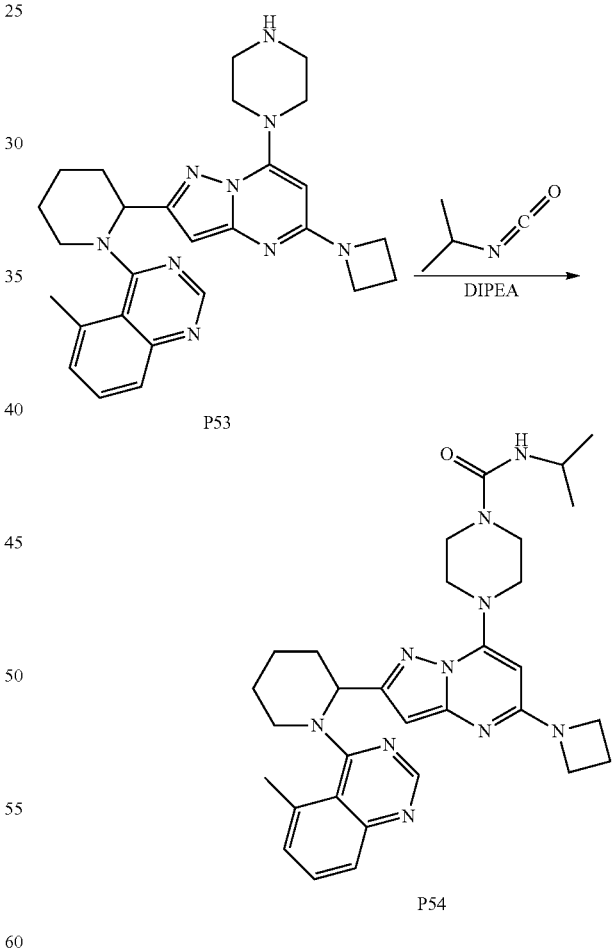

P53

P54

Compound P53 (550 mg, 1.058 mmol) was suspended in dioxane and hunig's base was added. The resulting mixture was stirred for 10 minutes. The 2-isocyanatopropane (125 μL, 1.269 mmol) was then added at room temperature. The mixture was stirred overnight at room temperature. To the solution was added an excess of MeOH and the mixture was stirred overnight. The solvent was evaporated. The residue was dissolved in dichloromethane (50 ml) and the resulting solution was washed with water three times (20 ml). The water layers were extracted with dichloromethane. The combined organic layers were dried over MgSO4 and filtered. The solvent was removed and the residue was triturated in diethyl ether and stirred overnight in this solvent. The white light powder was filtered and dried in the oven at 50° C. to yield (85 mg, 14%) of product P54.

m/z=569 (M+H)$^+$ $^1$H NMR (400 MHz, DMSO-d$_6$) δ ppm 1.11 (d, J=6.4 Hz, 6H), 1.52 (br. s., 1H), 1.66 (d, J=9.9 Hz, 2H), 1.84 (br. s., 1H), 2.21 (br. s., 2H), 2.28 (dt, J=14.5, 7.2 Hz, 2H), 2.85 (br. s, 3H), 3.30-3.62 (m, 10H), 3.73-3.86 (m, 1H), 3.98 (t, J=7.3 Hz, 4H), 5.19 (s, 1H), 5.42-5.81 (m, 3H), 7.30 (d, J=5.7 Hz, 1H), 7.50-7.70 (m, 2H), 8.46 (s, 1H)

Synthesis of 4-(2-(5-(azetidin-1-yl)-7-(4-(methylsulfonyl)piperazin-1-yl)pyrazolo-[1,5-a]pyrimidin-2-yl)piperidin-1-yl)-5-methylquinazoline P55 using dichloromethane and methanol as eluent to yield compound P55 71% pure. This was further purified by HPLC to yield (28 mg, 5%) of compound P55 as a white solid.

m/z=562 (M+H)$^+$ $^1$H NMR (400 MHz, DMSO-d6) δ ppm 1.58 (br. s., 1H), 1.65-1.77 (m, 2H), 1.78-1.94 (m, 1H), 2.20-2.27 (m, 2H), 2.27-2.38 (m, 2H), 2.87 (s, 3H), 2.91 (s, 3H), 3.22-3.35 (m, 4H), 3.44-3.68 (m, 6H), 4.02 (t, J=7.4 Hz, 4H), 5.26 (s, 1H), 5.49 (br. s., 1H), 5.67 (br. s., 1H), 7.30-7.36 (m, 1H), 7.58-7.67 (m, 2H), 8.49 (s, 1H)

Synthesis of 7-(2-(5-(azetidin-1-yl)-7-morpholinopyrazolo[1,5-a]pyrimidin-2-yl)-piperidin-1-yl)-2-methyloxazolo[5,4-d]pyrimidine P56

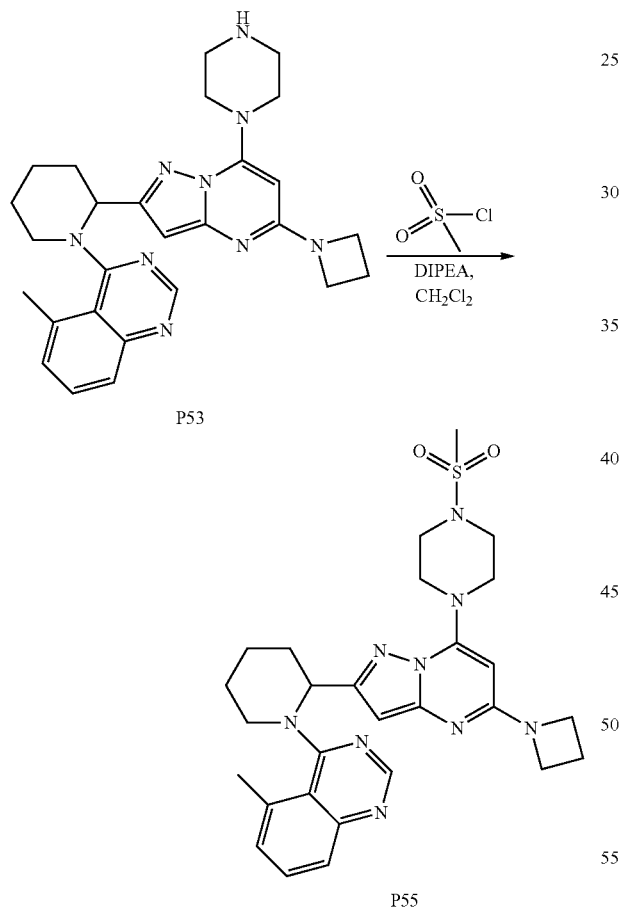

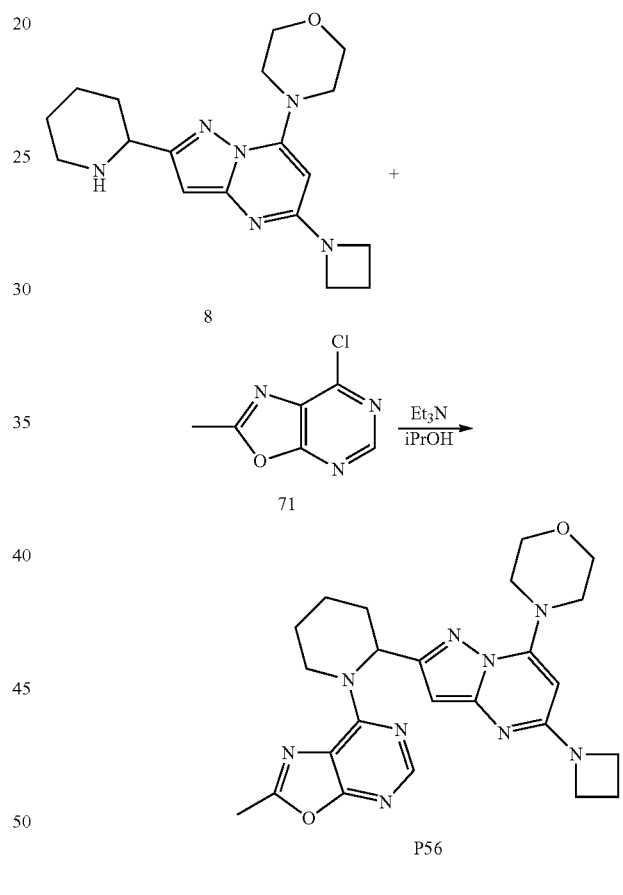

Synthesis of 7-chloro-2-methyloxazolo[5,4-d]pyrimidine 71

Compound P53 (500 mg, 1.03 mmol) was dissolved in dichloromethane (25 mL) and diisopropylethyl amine (0.445 mL, 2.58 mmol) was added. The resulting mixture was stirred at room temperate for 10 minutes then methanesulfonyl chloride (0.2 mL, 1.55 mmol) was added. The resulting mixture was stirred at room temperature overnight. The resulting mixture was poured in water, extracted with dichloromethane, dried over MgSO4 and concentrated. The resulting residue was purified by column chromatography

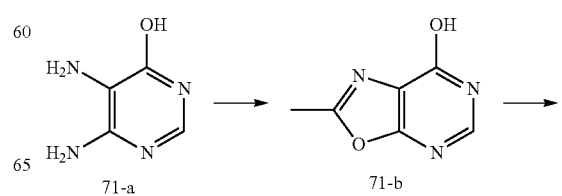

87
-continued

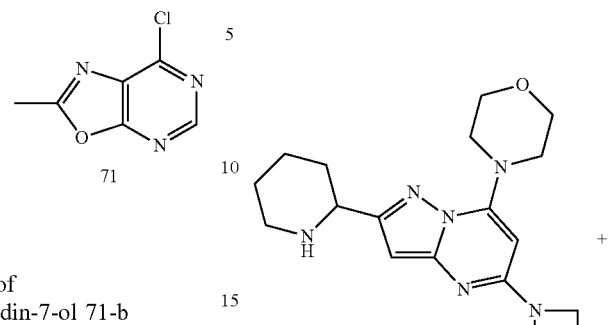

Step 1: synthesis of 2-methyloxazolo[5,4-d]pyrimidin-7-ol 71-b

A solution of 5-aminopyrimidine-4,6-diol 71-a (5 g, 39 mmol) in acetic anhydride (80 mL) was heated at 120° C. for 16 hours. The solution was then cooled and the solid filtered off and triturated with $Et_2O$. After filtration the solid was dried in the oven to yield the intermediate 71-b (4 g, 68%).

m/z=152 (M+H)⁺

¹H NMR (400 MHz, DMSO-$d_6$) δ ppm 2.54 (s, 3H) 8.18 (s, 1H) 12.84 (br. s., 1H)

Step 2: synthesis of 7-chloro-2-methyloxazolo[5,4-d]pyrimidine 71

The intermediate 71-b (100 mg, 0.66 mmol) was dissolved in acetonitrile (20 mL) under inert atmosphere. DIPEA (0.28 mL, 2.5 eq.) and $POCl_3$ (0.15 mL, 2.5 eq.) were added dropwise and the mixture was heated to 70° C. After 3 hours, the solution was concentrated in vacuo, extracted with ethyl acetate and washed with saturated $NaHCO_3$ solution. The combined organic layers were dried over $MgSO_4$, filtered and used as such into the next step.

LCMS m/z=170 (M+H)

Synthesis of 7-(2-(5-(azetidin-1-yl)-7-morpholinopyrazolo[1,5-a]pyrimidin-2-yl)-piperidin-1-yl)-2-methyloxazolo[5,4-d]pyrimidine P56

To a solution of intermediate 71 (20 mg, 0.12 mmol) in iPrOH (2 mL) was added triethyl amine (0.05 mL, 0.35 mmol, 3 eq.) and intermediate 8 (40 mg, 0.12 mmol, 1 eq.). The solution underwent microwave irradiation during 3 hours at 120° C. The resulting solution was concentrated in vacuo and purified by Prep HPLC to yield the title compound P56 (21 mg, 37%) as a white solid.

m/z=476 (M+H)⁺

¹H NMR (400 MHz, DMSO-$d_6$) δ ppm 1.49-1.79 (m, 4H) 1.84-2.02 (m, 1H) 2.20-2.34 (m, 2H) 2.40 (br. s., 1H) 2.53 (s, 3H) 3.15-3.27 (m, 1H) 3.36-3.54 (m, 4H) 3.55-3.69 (m, 4H) 3.99 (t, J=7.70 Hz, 4H) 4.99 (d, J=13.32 Hz, 1H) 5.22 (s, 1H) 5.73 (s, 1H) 6.53 (d, J=5.65 Hz, 1H) 8.24 (s, 1H)

88

Synthesis of 4-(5-(azetidin-1-yl)-2-(1-(6-methyl-2-(methylthio)quinazolin-4-yl)-piperidin-2-yl)pyrazolo[1,5-a]pyrimidin-7-yl)morpholine P57

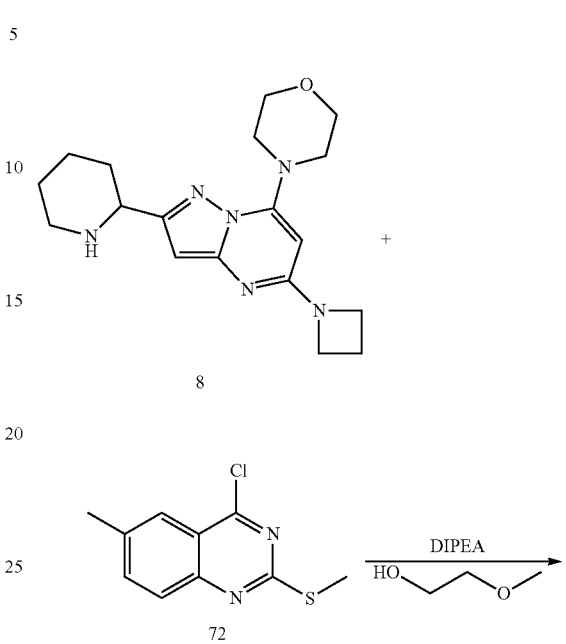

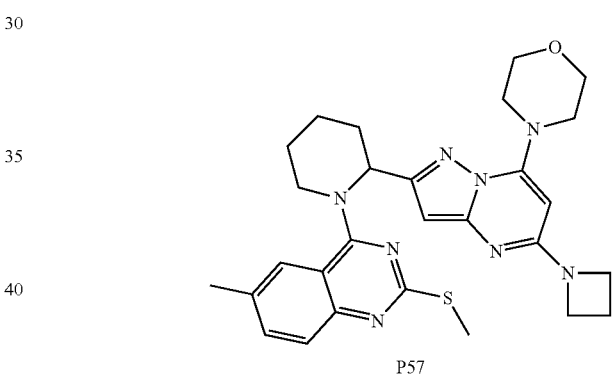

Intermediate 8 (1000 mg, 2.41 mmol), 4-chloro-6-methyl-2-(methylthio)quinazoline 72 (649.2 mg, 2.89 mmol) and DIPEA (0.83 ml, 4.8 mmol) were mixed in 2-methoxyethanol (30 ml) and heated at 50° C. for 16 hours. The reaction mixture was allowed to cool down to room temperature and poured in iced watered solution. A solid was formed this was filter off. The solid was dissolved in dichloromethane and the solution obtained was successively dried over MgSO4 and concentrated. The residue was purified by column chromatography to yield P57 (1.2 g, 78% pure).

m/z=531 (M+H)⁺

¹H NMR (400 MHz, DMSO-$d_6$) δ ppm 1.69 (br. s., 4H), 2.04 (dd, J=13.1, 5.2 Hz, 1H), 2.24-2.38 (m, 3H), 2.40 (s, 3H), 2.48 (s, 3H), 3.37-3.41 (m, 1H), 3.49 (t, J=4.5 Hz, 4H), 3.62-3.76 (m, 4H), 4.00 (t, J=7.5 Hz, 4H), 4.13 (d, J=13.2 Hz, 1H), 5.30 (s, 1H), 5.82 (d, J=2.2 Hz, 1H), 5.93 (s, 1H), 7.76 (s, 1H)

Synthesis of 4-(5-(azetidin-1-yl)-2-(1-(5-ethylquinazolin-4-yl)piperidin-2-yl)-pyrazolo[1,5-a]pyrimidin-7-yl)morpholine P58

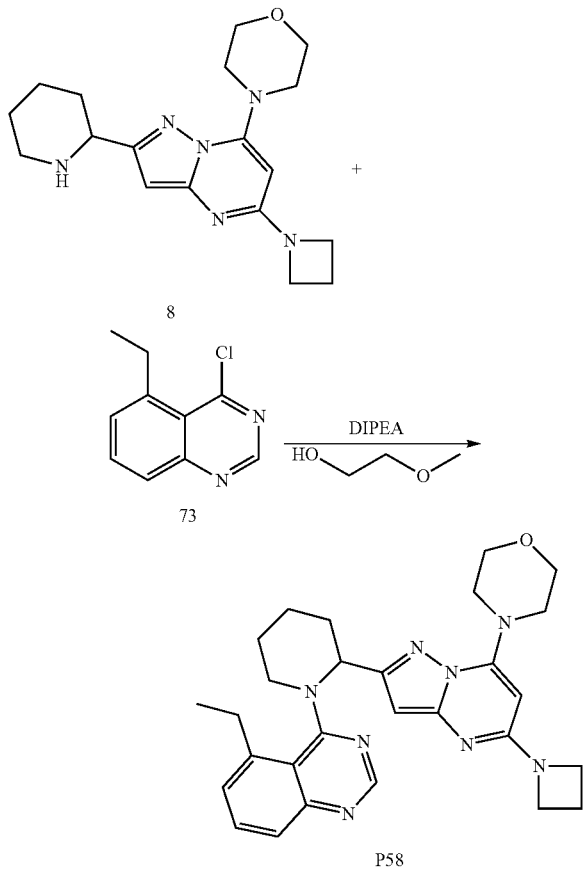

Synthesis of 4-chloro-5-ethylquinazoline 73

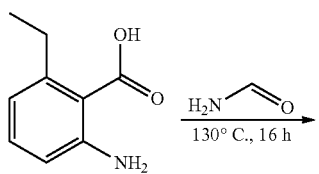

Step 1: synthesis of 5-ethylquinazolin-4-ol 73-b

A mixture of 2-amino-6-ethylbenzoic acid 73-a (18.0 g, 109 mmol) in formamide (200 ml) was stirred at 130° C. for 16 hours. The mixture was cooled to room temperature. The precipitate was filtered off and washed with water. The filter cake was dried in vacuum at 45° C. for 1 hour. The resulting solid intermediate 73-b was recovered (8.5 g, purity: 90%, yield: 40.3%).

Step 2: synthesis of 4-chloro-5-ethylquinazoline 73

Triethylamine (19.51 ml, 140.0 mmol) was added to a mixture of 5-ethylquinazolin-4 ol 73-b (7.0 g, 40 mmol) in phosphorus oxychloride (100 ml) at 0° C. The resulting mixture was refluxed for 3 hours. The solvent was evaporated under vacuum. The residue was dissolved in toluene (100 ml) and the mixture was added dropwise into ice (100 g). The organic layer was washed successively with water (2×100 ml), 10% sodium bicarbonate solution (2×100 ml), water (2×100 ml) and brine (1×100 ml). The organic layer was dried (Na$_2$SO$_4$), filtered and the filtrate was concentrated under vacuum. The residue was purified by flash column chromatography over silica gel (eluent: petroleum ether/ethyl acetate 10/1 to give intermediate 73 (3.313 g, purity: 96%, yield: 41.37%).

$^1$H NMR (400 MHz, CDCl$_3$) δ ppm 1.39 (t, J=7.46 Hz, 3H) 3.48 (q, J=7.34 Hz, 2H) 7.56 (d, J=7.34 Hz, 1H) 7.84 (t, J=7.83 Hz, 1H) 7.95 (d, J=8.31 Hz, 1H) 8.96 (s, 1H)

Step 3: synthesis of 4-(5-(azetidin-1-yl)-2-(1-(5-ethylquinazolin-4-yl)piperidin-2-yl)-pyrazolo[1,5-a]pyrimidin-7-yl)morpholine P58

The mixture of intermediate 8 HCl salt (500 mg, 1.2 mmol) and intermediate 73 (348 mg, 1.5 mmol) was dissolved in 2-methoxyethanol (15 ml) and triethyl amine (0.415 ml, 2.4 mmol) was added. The resulting mixture was stirred at 50° C. for 16 hours. The reaction mixture was allowed to cool down to room temperature and poured in iced watered solution. The resulting mixture was stirred until the ice melt then filtered off and the solid was washed with water. The solid was dissolved in dichloromethane, dried over MgSO4 and concentrated. The solid was purified by column chromatography using dichloromethane and methanol to yield P58 as a white powder (400 mg, 63%).

m/z=499 (M+H)$^+$ $^1$H NMR (400 MHz, DMSO-d6) δ ppm 1.05-1.23 (m, 3H), 1.42-1.57 (m, 1H), 1.66 (d, J=8.1 Hz, 2H), 1.73-1.91 (m, 1H), 2.06-2.35 (m, 4H), 3.10-3.41 (m, 3H), 3.40-3.55 (m, 5H), 3.58-3.78 (m, 5H), 3.89-4.06 (m, 4H), 5.18 (s, 1H), 5.35-5.66 (m, 2H), 7.37 (d, J=7.0 Hz, 1H), 7.50-7.68 (m, 2H), 8.43 (s, 1H)

Synthesis of 4-(5-(azetidin-1-yl)-2-(1-(5,7-dimethylquinazolin-4-yl)piperidin-2-yl)-pyrazolo[1,5-a]pyrimidin-7-yl)morpholine P59

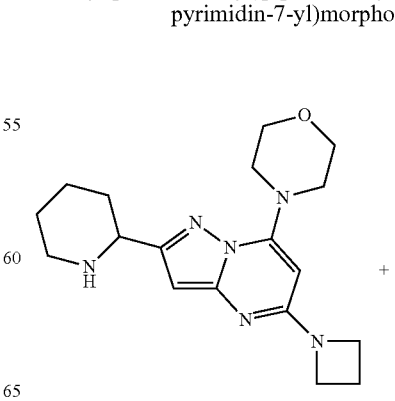

-continued

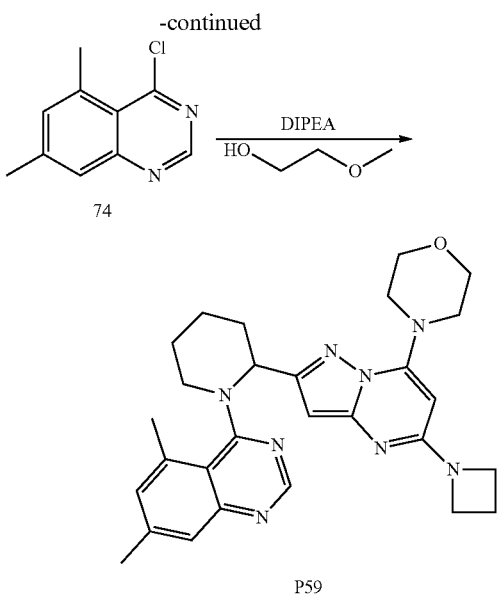

Synthesis of 4-chloro-5,7-dimethylquinazoline 74

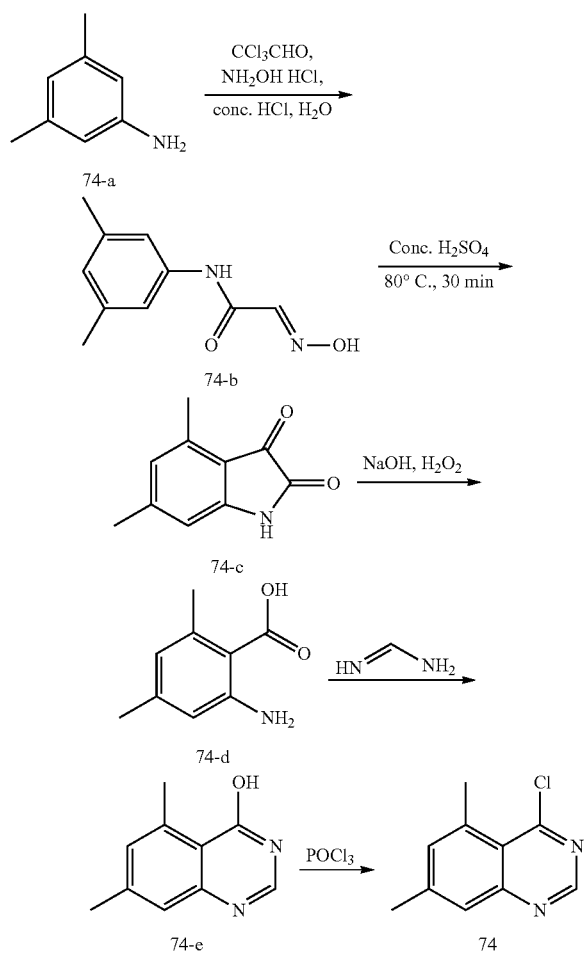

Step 1: synthesis of (E)-N-(3,5-dimethylphenyl)-2-(hydroxyimino)acetamide 74-b

Sodium sulfate (390.7 g, 2.750 mol) was added into a solution of chloral hydrate (76.5 g, 0.520 mol) in water (1500 mL) at room temperature. Then, a suspension of hydroxylamine hydrochloride (91.8 g, 1.32 mol), 3,5-dimethylaniline 74-a (50 g, 0.41 mol) and concentrated hydrochloric acid (36.5%, 50 mL) was added. The mixture was heated at 45° C. for 1.5 hours, then 75° C. for 1 hour. The reaction mixture was cooled to room temperature. The precipitated brown solid was filtered and washed with cold water and hexane. The crude compound was dried under vacuum to give intermediate 74-b (70 g, yield: 83.78%).

Step 2: synthesis of 4,6-dimethylindoline-2,3-dione 74-c

Intermediate 74-b (15.00 g, 78.04 mmol) was dissolved in concentrated sulfuric acid (75 ml). The mixture was stirred at 80° C. for 30 minutes. Then the mixture was cooled to room temperature and poured into ice water. Intermediate 75-c was precipitated, filtered and washed with water (8.50 g, 49.74%).

Step 3: synthesis of 2-amino-4,6-dimethylbenzoic acid 74-d $H_2O_2$ (123.7 g, 1200 mmol) was added to a mixture of intermediate 74-C (35.00 g, 199.8 mmol) in NaOH solution (1225 mL, 0.33 g/mL) at 70° C., over 5 minutes. The mixture was heated for another 15 minutes, then cooled to 15° C. Ice was added to the mixture. The resulting mixture was extracted with ethyl acetate (300 mL×2). The pH of the solution was adjusted to 8 with addition of concentrated HCl at 0° C. and acidified to pH ~6 with acetic acid. The mixture was extracted with ethyl acetate (300 mL×2). The organic layers were combined, washed with brine, dried over $MgSO_4$ and filtered. The filtrate was concentrated to give intermediate 74-d (17 g, yield: 41.20%).

Step 4: synthesis of 5,7-dimethylquinazolin-4-ol 74-e

A mixture of intermediate 74-d (15.0 g, 90.8 mmol) and formamidine acetate (94.5 g, 908 mmol) was stirred for 5 hours at 150° C. $H_2O$ was added to the mixture and the mixture was stirred 10 minutes at room temperature. The precipitate was filtered off and washed with water. The filter cake was dried under vacuum to give intermediate 74-e (17.5 g, yield: 39.83%).

Step 5: synthesis of 4-chloro-5,7-dimethylquinazoline 74

Triethylamine (30.50 ml, 301.4 mmol) was added to a mixture of intermediate 74-e (17.50 g, 100.5 mmol) in $POCl_3$ (300 g, 1.96 mol) at 0° C. The resulting mixture was refluxed for 3 hours then was poured into ice water. The resulting mixture was extracted with ethyl acetate. The organic layer was washed with $NaHCO_3$ solution (1%) and brine, dried over $MgSO_4$ and filtered. The filtrate was concentrated. The crude product was purified by chromatography over silica gel (eluent: hexanes/ethyl acetate from 0/1 to 1:1). The desired fractions were collected and concentrated to give intermediate 74 (4.806 g, 23.69%).

$^1$H NMR (400 MHz, CDCl$_3$) δ ppm 2.53 (s, 3H) 3.00 (s, 3H) 7.34 (s, 1H) 7.71 (s, 1H) 8.90 (s, 1H)

Synthesis of 4-(5-(azetidin-1-yl)-2-(1-(5,7-dimethylquinazolin-4-yl)piperidin-2-yl)-pyrazolo[1,5-a]pyrimidin-7-yl)morpholine P59

The mixture of intermediate 8 TFA salt (300 mg, 0.66 mmol) and intermediate 74 (177 mg, 0.92 mmol) was dissolved in 2-methoxyethanol (15 ml) and triethyl amine (0.34 ml, 1.97 mmol) was added. The resulting mixture was stirred at 50° C. for 16 hours. The reaction mixture was allowed to cool down to room temperature and poured in iced watered solution. The resulting mixture was stirred until the ice melt then filtered off and the solid was washed with water. The solid was dissolved in dichloromethane dried over MgSO4 and concentrated. The solid was purified by column chromatography using dichloromethane and methanol to yield P59 as a white powder (212 mg, 64%).

m/z=499 (M+H)$^+$ $^1$H NMR (400 MHz, DMSO-d$_6$) δ ppm 1.52 (br. s., 1H), 1.65 (d, J=5.1 Hz, 2H), 1.74-1.90 (m, 1H), 2.17 (br. s., 2H), 2.28 (quin, J=7.3 Hz, 2H), 2.41 (s, 3H), 2.80 (s, 3H), 3.35-3.58 (m, 6H), 3.60-3.77 (m, 4H), 3.98 (t, J=7.3 Hz, 4H), 5.17 (s, 1H), 5.41 (br. s., 1H), 5.53-5.73 (m, 1H), 7.14 (s, 1H), 7.38 (s, 1H), 8.42 (s, 1H)

Synthesis of 4-(5-(azetidin-1-yl)-2-(1-(5-fluoroquinazolin-4-yl)piperidin-2-yl)-pyrazolo[1,5-a]pyrimidin-7-yl)morpholine P60

The mixture of intermediate 8 TFA salt (400 mg, 0.87 mmol) and 4-chloro-5-fluoro-quinazoline 75 (208 mg, 1.14 mmol) was dissolved in 2-methoxyethanol (20 ml) and triethyl amine (0.604 ml, 3.5 mmol) was added. The resulting mixture was stirred at 50° C. for 2 hours. The reaction mixture was allowed to cool down to room temperature and poured in iced watered solution. The resulting mixture was stirred until the ice melt then filtered off and the solid was washed with water. The solid was dissolved in dichloromethane, dried over MgSO4 and concentrated to yield a white solid P60 (145 mg, 34%).

m/z=489 (M+H)$^+$ $^1$H NMR (400 MHz, DMSO-d$_6$) δ ppm 1.57-1.90 (m, 4H), 2.06-2.20 (m, 1H), 2.26-2.43 (m, 3H), 3.38-3.51 (m, 1H), 3.54 (br. s., 4H), 3.65-3.79 (m, 4H), 3.92 (d, J=12.8 Hz, 1H), 4.02 (t, J=7.4 Hz, 4H), 5.23 (s, 1H), 5.75 (s, 1H), 5.80 (br. s., 1H), 7.23 (dd, J=11.7, 7.9 Hz, 1H), 7.61 (d, J=8.4 Hz, 1H), 7.68-7.79 (m, 1H), 8.51 (s, 1H)

Synthesis of 4-(5-(azetidin-1-yl)-2-(1-(5-ethoxyquinazolin-4-yl)piperidin-2-yl)-pyrazolo[1,5-a]pyrimidin-7-yl)morpholine P61

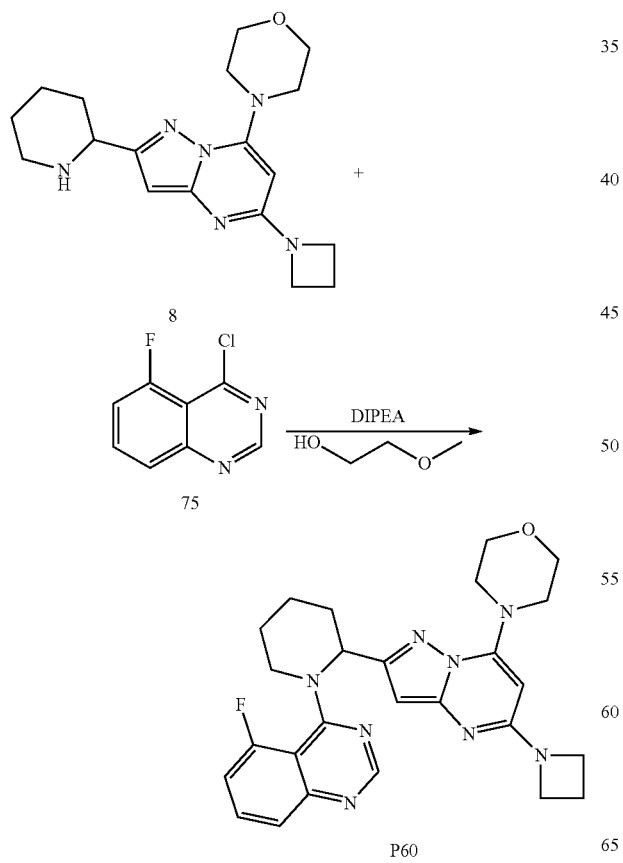

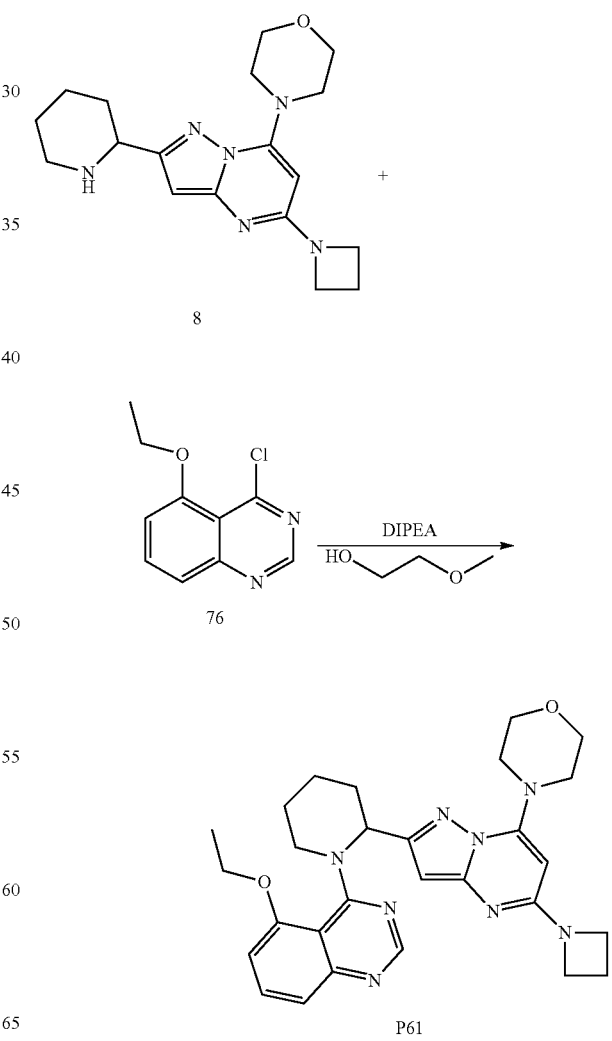

Synthesis of 4-chloro-5-ethoxyquinazoline 76

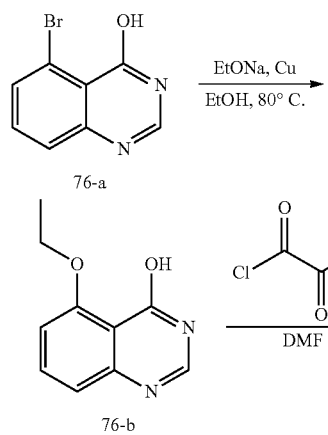

Step 1: synthesis of 5-ethoxyquinazolin-4-ol 76-b

Sodium hydride (8.00 g, 200 mmol, 60% in mineral oil) was added to ethanol (300 ml) at 0° C. After stirred for 30 min at 0° C. 5-bromoquinazolin-4-ol 76-a (15.00 g, 66.65 mmol) and cupper (1.70 g, 26.7 mmol) were added. The reaction mixture was stirred at 80° C. for 18 h and then cooled to room temperature. The mixture was filtered through a pad of Celite. The filtrate was concentrated in vacuum. The residue was taken up in water and the pH was adjusted to 8 by addition of a solution of hydrochloric acid 37%. The solution was extracted with $CH_2Cl_2$. The organic phase was dried over $Na_2SO_4$, filtered and evaporated in vacuum. The residue was purified by column chromatography over silica gel (eluent: petroleum ether/ethyl acetate 2/1) to afford intermediate 76-b (5 g, yield: 35%).

Step 2: synthesis of 4-chloro-5-ethoxyquinazoline 76

Oxalyl chloride (12.5 mmol) was added dropwise to a solution of intermediate 76-b (5.00 g, 26.3 mmol) and DMF (2.5 ml) in $CH_3Cl$ (100 ml). The solution was refluxed overnight. The reaction solution was concentrated under vacuum. The residue was purified over silica gel on a glass filter (eluent: $CH_2Cl_2$/ethyl acetate 1/1). The desired fractions were collected and the solvent was evaporated to afford intermediate 77 (2.81 g, yield: 49%).

$^1$H NMR (400 MHz, DMSO-$d_6$) δ ppm 1.34-1.48 (m, 3H) 4.14-4.23 (m, 2H) 7.15-7.23 (m, 1H) 7.27-7.36 (m, 1H) 7.77-7.87 (m, 1H) 8.90 (s, 1H) The mixture of intermediate 8 TFA salt (500 mg, 1.1 mmol) and 4-chloro-5-ethoxyquinazoline 76 (320 mg, 1.5 mmol) was dissolved in 2-methoxyethanol (20 ml) and triethyl amine (0.566 ml, 3.3 mmol) was added. The resulting mixture was stirred at 50° C. for 4 days. The reaction mixture was allowed to cool down to room temperature and poured in iced watered solution. The resulting mixture was stirred until the ice melt then filtered off and the solid was washed with water. The solid was dissolved in dichloromethane dried over MgSO4 and concentrated to yield a residue that was purified by preparative HPLC to yield P61 as a white solid (76 mg, 13%).

m/z=515 (M+H)$^+$ $^1$H NMR (400 MHz, DMSO-$d_6$) δ ppm 1.33-1.49 (m, 3H), 1.51-1.92 (m, 4H), 2.08-2.24 (m, 1H), 2.25-2.43 (m, 3H), 3.27-3.47 (m, 1H), 3.48-3.63 (m, 4H), 3.65-3.82 (m, 4H), 3.87-4.10 (m, 5H), 4.15-4.35 (m, 2H), 5.22 (s, 1H), 5.67 (br. s., 1H), 5.83 (br. s., 1H), 6.98 (d, J=7.7 Hz, 1H), 7.31 (d, J=8.1 Hz, 1H), 7.55-7.69 (m, 1H), 8.38 (br. s., 1H)

Synthesis of 4-(5-(azetidin-1-yl)-2-(1-(5-(trifluoromethyl)quinazolin-4-yl)piperidin-2-yl)pyrazolo[1,5-a]pyrimidin-7-yl)morpholine P62

Synthesis of 4-chloro-5-(trifluoromethyl)quinazoline 77

Step 1: synthesis of 5-(trifluoromethyl)quinazolin-4(3H)-one 77-b

A mixture of 2-amino-6-(trifluoromethyl)benzoic acid 77-a (9.00 g, 43.9 mmol) and formamidine acetate (22.84 g, 219.4 mmol) in n-butanol (180 ml) was stirred at 100° C. for 5 hours. The solvent was evaporated under vacuum. The residue was washed with ethanol (2×50 ml) and then dried in vacuum at 45° C. for 1 hour to give intermediate 77-b (9 g, yield: 91%).

Step 2: synthesis of 4-chloro-5-(trifluoromethyl)quinazoline 77

Triethyl amine (29.3 ml, 210 mmol) was added to a mixture of intermediate 77-b (8.00 g, 37.4 mmol) in phosphorus oxychloride (331 g, 2.16 mol) at 0° C. The mixture was refluxed for 2 hours. The solvent was evaporated under vacuum. The residue was dissolved in ethyl acetate (200 ml) and the mixture was added to ice (200 g). The separated organic layer was washed successively with water (1×100 ml), 10% sodium bicarbonate aqueous solution (2×100 ml), water (1×100 ml) and brine (1×100 ml). The separated organic layer was dried over sodium sulfate, filtered and concentrated under vacuum. The residue was purified by column chromatography over silica gel (eluent: petroleum ether/ethyl acetate 1/0 to 1/1) to give intermediate 77 (7.97 g, 91.38%).

$^1$H NMR (400 MHz, CDCl$_3$) δ ppm 7.89-8.06 (m, 1H) 8.22 (d, J=7.50 Hz, 1H) 8.31 (d, J=8.38 Hz, 1H) 9.11 (s, 1H)

Synthesis of 4-(5-(azetidin-1-yl)-2-(1-(5-(trifluoromethyl)quinazolin-4-yl)piperidin-2-yl)pyrazolo[1,5-a]pyrimidin-7-yl)morpholine P62

The mixture of intermediate 8 TFA salt (300 mg, 0.65 mmol), intermediate 77 (183 mg, 0.78 mmol) was dissolved in 2-methoxyethanol (20 mL) then diisopropylethyl amine (0.45 mL, 2.6 mmol) was added. The resulting mixture was stirred at 50° C. overnight. The mixture was allowed to cool down to room temperature and poured in iced watered solution. The resulting mixture was stirred until all the ice is melt then the resulting solid was filtered off. The solid was successively washed with water, dissolved in dichloromethane, dried over MgSO4 and concentrated to yield P62 (250 mg, 70%) as a white light solid.

m/z=539 (M+H)$^+$ $^1$H NMR (400 MHz, DMSO-d$_6$) δ ppm 1.37-1.60 (m, 1H), 1.69 (br. s., 2H), 1.82 (d, J=11.9 Hz, 1H), 2.07-2.40 (m, 4H), 3.32-3.59 (m, 5H), 3.62-3.80 (m, 5H), 4.02 (t, J=7.4 Hz, 4H), 5.20 (s, 1H), 5.46-5.70 (m, 2H), 7.81-7.91 (m, 2H), 7.94-8.01 (m, 1H), 8.49 (s, 1H)

Synthesis of 4-(5-(azetidin-1-yl)-2-(1-(6-ethyl-5-methylquinazolin-4-yl)piperidin-2-yl)pyrazolo[1,5-a]pyrimidin-7-yl)morpholine P63

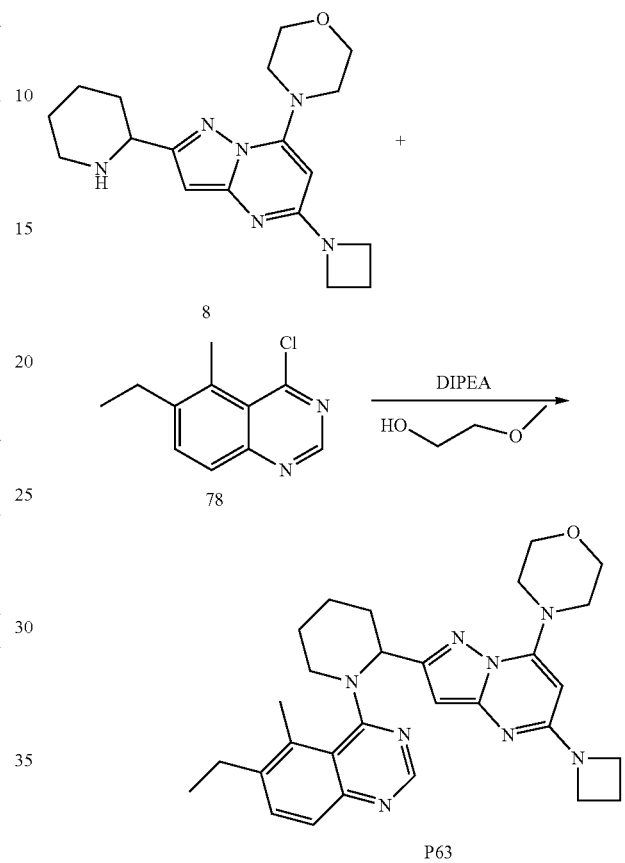

Synthesis of 4-chloro-6-ethyl-5-methylquinazoline 78

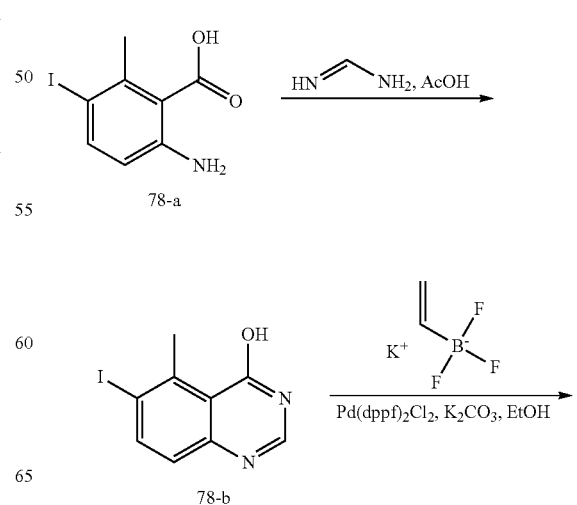

-continued

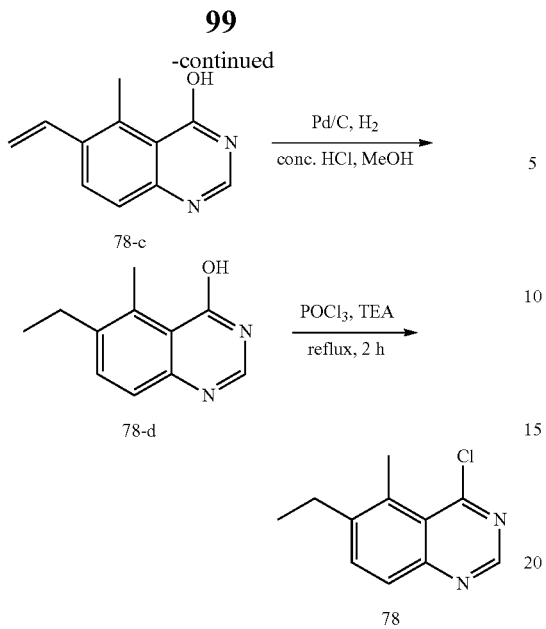

Step 1: synthesis of 6-iodo-5-methylquinazolin-4-ol 78-b

A solution of 6-amino-3-iodo-2-methylbenzoic acid 78-a (35.0 g, 126 mmol) and formamidine acetate (59.0 g, 567 mmol) in EtOH (500 ml) was refluxed overnight. The precipitate was filtered off and washed with ethanol to afford intermediate 78-b (21 g, yield 52%).

Step 2: synthesis of 5-methyl-6-vinylquinazolin-4-ol 78-c

A solution of intermediate 78-b (15.0 g, 52.4 mmol), potassium trifluoro(vinyl)borate (10.6 g, 79.0 mmol), Pd(dppf)$_2$Cl$_2$ (1.7 g, 2.6 mmol) and K$_2$CO$_3$ (21.74 g, 157.3 mmol) in EtOH (150 ml) was refluxed overnight. The solvent was evaporated under vacuum. The residue was treated with H$_2$O and CH$_2$Cl$_2$. The separated organic layer was dried over MgSO4, filtrated and evaporated under vacuum. The residue was purified by high-performance liquid chromatography over SYNERGI (eluent: TFA water/acetonitrile 30/70 v/v). The product fractions were collected and the organic solvent was evaporated. The pH was adjusted to 7 with saturated NaHCO$_3$. The aqueous concentrate was extracted with CH$_2$Cl$_2$. The separated organic layer was concentrated under vacuum to afford intermediate 78-c (3 g, yield 29%).

Step 3: synthesis of 6-ethyl-5-methylquinazolin-4-ol 78-d

A solution of intermediate 78-c (3.0 g, 16 mmol) and HCl (11.5 ml) in MeOH (30 ml) was hydrogenated at room temperature (50 psi) with Pd/C (0.6 g) as a catalyst for 15 hours. After uptake of H$_2$ (32.50 mg, 16.11 mmol), the catalyst was filtered off and washed with methanol. The solvent was evaporated under vacuum to afford intermediate 78-d (2.1 g, yield 66%).

Step 4: synthesis of 4-chloro-6-ethyl-5-methylquinazoline 78

A mixture of intermediate 78-d (1.80 g, 9.56 mmol), triethylamine (2.220 ml, 15.95 mmol) and phosphorus oxychloride (60 ml) was refluxed for 2 hours. The solvent was evaporated under vacuum. The residue was dissolved in ethyl acetate (200 ml) and the mixture was added drop wise into ice (200 g). The separated organic layer was washed successively with water (1×100 ml), 10% sodium bicarbonate aqueous solution (2×100 ml), water (1×100 ml) and brine (1×100 ml). The organic layer was dried (MgSO$_4$), filtered and the filtrate was concentrated under vacuum. The residue was purified by column chromatography over silica gel (eluent: petroleum ether/ethyl acetate 1/0 to 5/1) to give intermediate 78 (1.434 g, 68.94%).

$^1$H NMR (400 MHz, CDCl$_3$) δ ppm 1.27 (t, J=7.65 Hz, 3H) 2.88 (q, J=7.53 Hz, 2H) 2.94 (s, 3H) 7.75 (d, J=8.53 Hz, 1H) 7.87 (d, J=8.53 Hz, 1H) 8.89 (s, 1H)

Step 5: synthesis of 4-(5-(azetidin-1-yl)-2-(1-(6-ethyl-5-methylquinazolin-4-yl)-piperidin-2-yl)pyrazolo[1,5-a]pyrimidin-7-yl)morpholine P63

The mixture of intermediate 8 TFA salt (400 mg, 0.87 mmol), intermediate 78 (235 mg, 1.14 mmol) was dissolved in 2-methoxyethanol (20 mL) then diisopropylethyl amine (0.604 mL, 3.5 mmol) was added. The resulting mixture was stirred at 50° C. for 4 days. The mixture was allowed to cool down to room temperature and poured in iced watered solution. The resulting mixture was stirred until all the ice is melt then the resulting solid was filtered off. The solid was successively washed with water, dissolved in dichloromethane, dried over MgSO4 and concentrated the residue was purified by preparative HPLC to yield P63 (198 mg, 44%) as a white light solid.

m/z=513 (M+H)$^+$ $^1$H NMR (400 MHz, DMSO-d$_6$) δ ppm 1.26 (t, J=7.5 Hz, 3H), 1.37-1.58 (m, 1H), 1.67 (br. s., 2H), 1.77-1.94 (m, 1H), 2.12-2.39 (m, 6H), 2.75-2.89 (m, 6H), 3.52 (br. s., 5H), 3.65-3.80 (m, 4H), 4.02 (t, J=7.4 Hz, 4H), 5.21 (s, 1H), 5.61 (s, 2H), 7.49-7.63 (m, 2H), 8.40 (s, 1H)

Synthesis of 4-(5-(azetidin-1-yl)-2-(1-(5,6-dimethylquinazolin-4-yl)piperidin-2-yl)-pyrazolo[1,5-a]pyrimidin-7-yl)morpholine P64

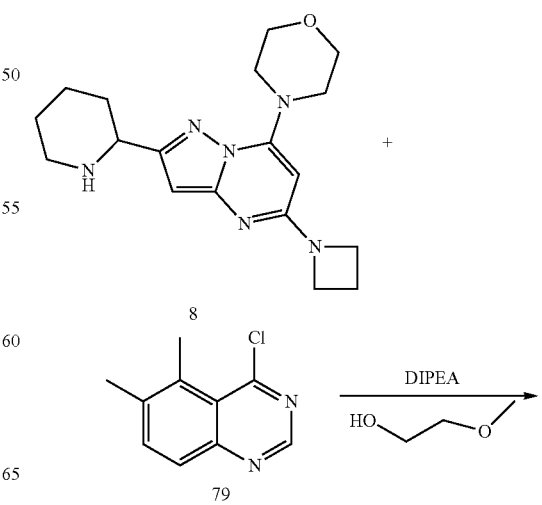

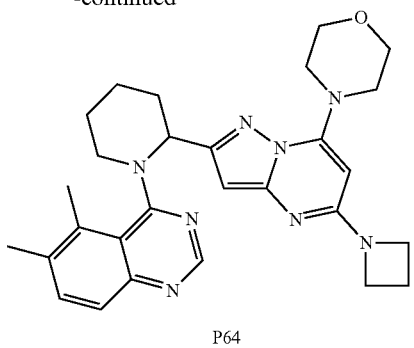

P64

Synthesis of 4-chloro-5,6-dimethylquinazoline 79

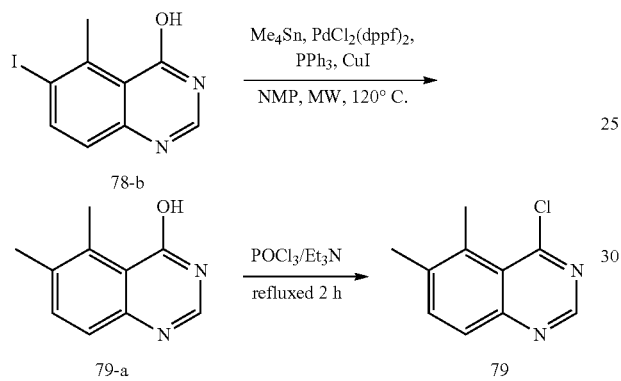

Step 1: synthesis of 5,6-dimethylquinazolin-4-ol 79-a

PdCl$_2$(dppf)$_2$ (114 mg, 0.180 mmol) and PPh$_3$ (183 mg, 0.700 mmol) were added to a mixture of intermediate 78-b (1.0 g, 3.5 mmol), Me$_4$Sn (940 mg, 5.20 mmol) and CuI (67 mg, 0.35 mmol) in NMP (15 ml) under N$_2$. The mixture was stirred under microwave at 150° C. for 0.5 hours. The resulting mixture was poured into water. The precipitate was filtered off and concentrated under vacuum. The residue was purified by column chromatography over silica gel (eluent: methanol/ethyl acetate 1/10) to afford intermediate 79-a (0.7 g, yield: 27%).

Step 2: synthesis of 4-chloro-5,6-dimethylquinazoline 79

A mixture of intermediate 79-a (700 mg, 4.02 mmol), phosphorus oxychloride (20 ml) and triethylamine (2.80 ml, 20.1 mmol) was refluxed for 2 hours. The solvent was evaporated under vacuum. The residue was dissolved in ethyl acetate (50 ml) and the mixture was added to ice (20 g). The separated organic layer was successively washed with water (1×20 ml), 10% sodium bicarbonate aqueous solution (2×20 ml), water (1×20 ml) and brine (1×20 ml). The organic layer was dried over magnesium sulfate, filtered, concentrated under vacuum. The residue was purified by column chromatography over silica gel (eluent: petroleum ether/ethyl acetate 1/0 to 10/1) to give intermediate 79 (598.30 mg, 73%).

$^1$H NMR (400 MHz, CDCl$_3$) δ ppm 2.53 (s, 3H) 2.92 (s, 3H) 7.68-7.78 (m, 1H) 7.80-7.89 (m, 1H) 8.89 (s, 1H).

Step 3: synthesis of 4-(5-(azetidin-1-yl)-2-(1-(5,6-dimethylquinazolin-4-yl)piperidin-2-yl)pyrazolo[1,5-a]pyrimidin-7-yl)morpholine P64

The mixture of intermediate 8 TFA salt (300 mg, 0.65 mmol), intermediate 79 (183 mg, 0.95 mmol) was dissolved in 2-methoxyethanol (15 mL) then diisopropylethyl amine (0.45 mL, 2.6 mmol) was added. The resulting mixture was stirred at 50° C. for three days. The mixture was allowed to cool down to room temperature and poured in iced watered solution. The resulting mixture was stirred until all the ice is melt then the resulting solid was filtered off. The solid was successively washed with water, dissolved in dichloromethane, dried over MgSO4 and concentrated to yield compound P64 (150 mg, 45%) as a white light solid.

m/z=499 (M+H)$^+$ $^1$H NMR (400 MHz, DMSO-d$_6$) δ ppm 1.67 (br. s., 3H), 1.82 (d, J=11.7 Hz, 1H), 2.09-2.37 (m, 4H), 2.41 (s, 3H), 2.67-2.86 (m, 4H), 3.52 (br. s., 5H), 3.65-3.83 (m, 4 H), 4.02 (t, J=7.4 Hz, 4H), 5.21 (s, 1H), 5.40-5.90 (m, 2H), 7.48-7.59 (m, 2H), 8.40 (s, 1H)

Synthesis of 7-(2-(5-(azetidin-1-yl)-7-morpholinopyrazolo[1,5-a]pyrimidin-2-yl)-piperidin-1-yl)-2-methyloxazolo[5,4-d]pyrimidine P65

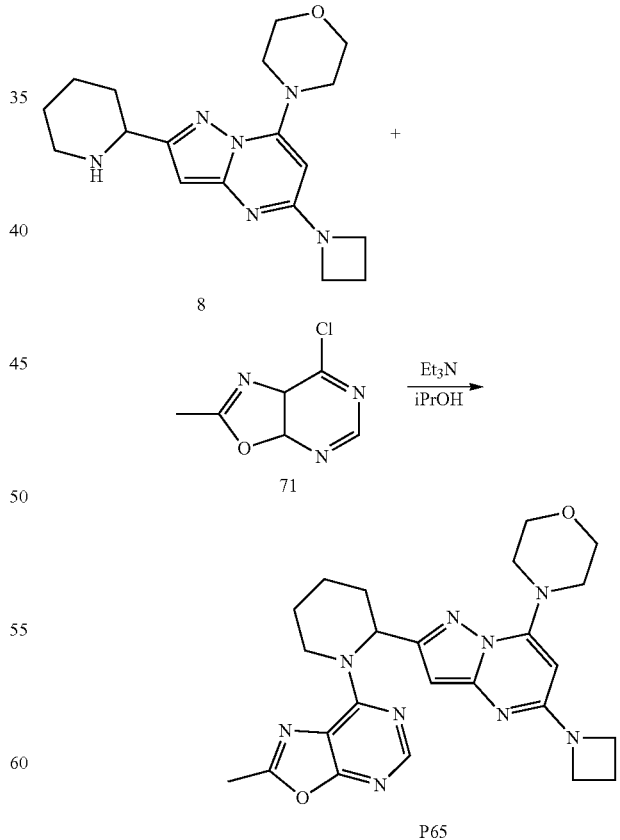

To a solution of intermediate 71 (20 mg, 0.12 mmol) in iPrOH (2 mL) was added triethyl amine (0.05 mL, 0.35 mmol, 3 eq.) and intermediate 8 (40 mg, 0.12 mmol, 1 eq.).

The solution underwent microwave irradiation during 3 hours at 120° C. The resulting solution was concentrated in vacuum and purified by Prep HPLC to yield the title compound P65 (21 mg, 37%) as a white solid.

m/z=476 (M+H)+

¹H NMR (400 MHz, DMSO-d₆) δ ppm 1.49-1.79 (m, 4H) 1.84-2.02 (m, 1H) 2.20-2.34 (m, 2H) 2.40 (br. s., 1H) 2.53 (s, 3H) 3.15-3.27 (m, 1H) 3.36-3.54 (m, 4H) 3.55-3.69 (m, 4H) 3.99 (t, J=7.70 Hz, 4H) 4.99 (d, J=13.32 Hz, 1H) 5.22 (s, 1H) 5.73 (s, 1H) 6.53 (d, J=5.65 Hz, 1H) 8.24 (s, 1H)

Synthesis of 4-(5-(azetidin-1-yl)-2-(1-(5,8-dimethylquinazolin-4-yl)piperidin-2-yl)-pyrazolo[1,5-a]pyrimidin-7-yl)morpholine P66

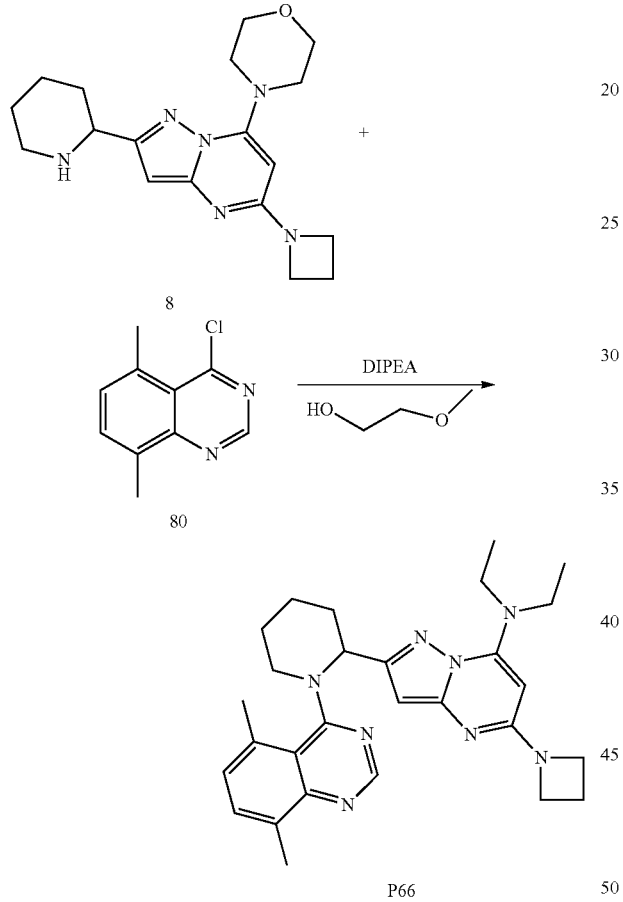

The mixture of intermediate 8 TFA salt (300 mg, 0.65 mmol), 4-chloro-5,8-dimethyl-quinazoline 80 (175 mg, 0.9 mmol) was dissolved in 2-methoxyethanol (15 mL) then diisopropylethyl amine (0.45 mL, 2.6 mmol) was added. The resulting mixture was stirred at 50° C. for three days. The mixture was allowed to cool down to room temperature and poured in iced watered solution. The resulting mixture was stirred until all the ice is melt then the resulting solid was filtered off. The solid wasn't pure it was dissolved in dichloromethane the water layer was extracted with dichloromethane all the organics were combined and dried over MgSO4.

The solvent was removed and the residue was purified by column chromatography using dichloromethane and methanol. The compound P66 was isolated as a white solid (150 mg, 46%).

m/z=499 (M+H)+

¹H NMR (400 MHz, DMSO-d₆) δ ppm 1.51 (br. s., 1H), 1.64 (d, J=7.7 Hz, 2H), 1.82 (d, J=7.9 Hz, 1H), 2.18 (br. s., 2H), 2.28 (quin, J=7.4 Hz, 2H), 2.56 (s, 3H), 2.78 (s, 3H), 3.35-3.56 (m, 6H), 3.61-3.74 (m, 4H), 3.98 (t, J=7.4 Hz, 4H), 5.17 (s, 1H), 5.46 (br. s., 1H), 5.62 (br. s., 1H), 7.18 (d, J=7.3 Hz, 1H), 7.46 (d, J=7.3 Hz, 1H), 8.50 (s, 1H)

Synthesis of methyl 4-(2-(5-(azetidin-1-yl)-7-morpholinopyrazolo[1,5-a]pyrimidin-2-yl)piperidin-1-yl)-5-methylquinazoline-2-carboxylate P67

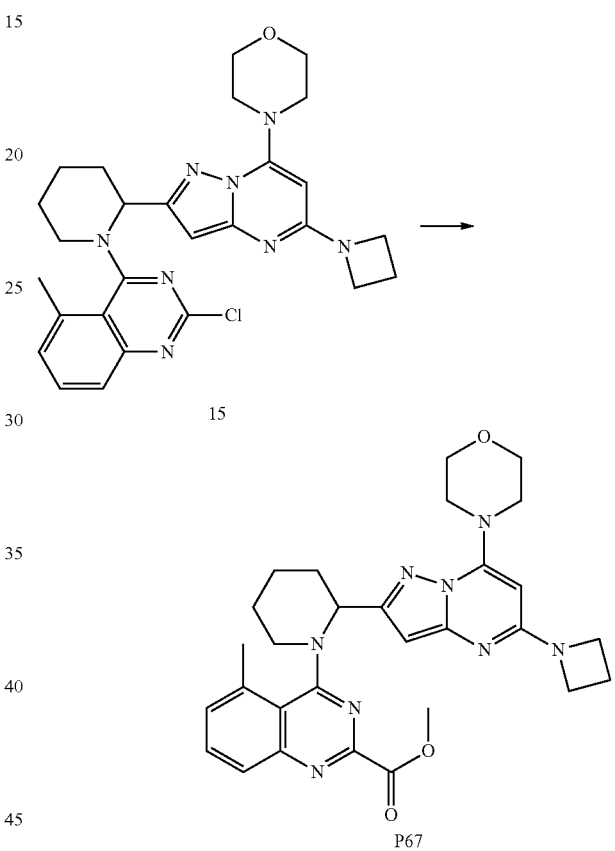

Intermediate 15 (100 mg, 0.13 mmol) was dissolved in 30 mL THF/MeOH (3/1) in an autoclave. Potassium acetate (20 mg, 0.20 mmol, 1.5 eq.), Pd(OAc)₂ (3 mg, 0.013 mmol, 0.1 eq.) and 1,3-bis(diphenylphosphino)propane (11 mg, 0.027 mmol, 0.2 eq.) were added. The autoclave was heated to 120° C. under 50 bar carbon monoxide pressure during 8 hours. After cooling to room temperature the solution was concentrated in vacuum and diluted with DCM then washed with saturated solution of NaHCO₃. The combined organics were dried with MgSO₄, filtered off and concentrated in vacuum. The crude was further purified on HPLC giving methyl compound P67 (43 mg, 60%).

m/z=543 (M+H)+

¹H NMR (400 MHz, 420 K, DMSO-d₆) δ ppm 1.42-1.59 (m, 1H) 1.62-1.70 (m, 2H) 1.77-1.88 (m, 1H) 2.14-2.33 (m, 4H) 2.80 (s, 3H) 3.43-3.55 (m, 5H) 3.64-3.74 (m, 5H) 3.85 (s, 3H) 3.99 (t, J=7.41 Hz, 4H) 5.18 (s, 1H) 5.61 (m, J=3.98 Hz, 1H) 5.66 (s, 1H) 7.39 (t, J=4.22 Hz, 1H) 7.66 (d, J=4.30 Hz, 2H)

Synthesis of 4-(2-(5-(azetidin-1-yl)-7-morpholinopyrazolo[1,5-a]pyrimidin-2-yl)-piperidin-1-yl)-5-methylquinazoline-2-carboxylic acid P68

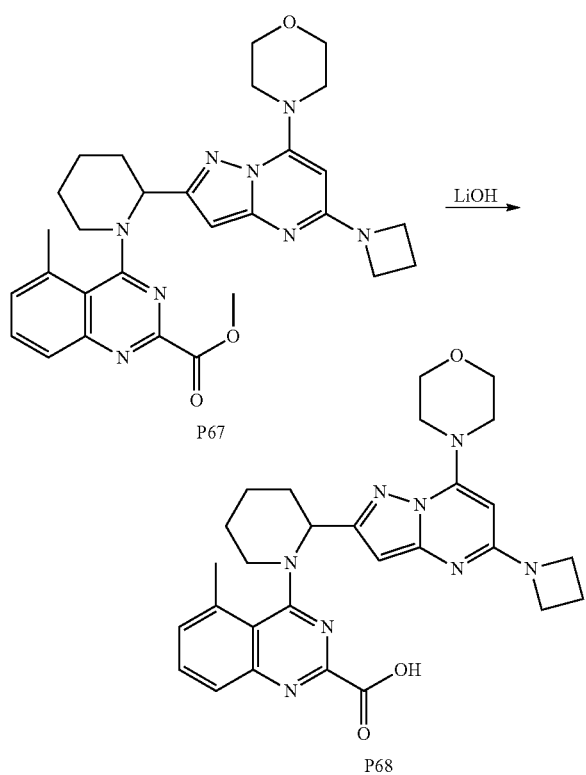

To a solution of compound P67 (300 mg, 0.38 mmol) in 30 mL THF/water (3/1) was added LiOH (28 mg, 1.16 mmol, 3 eq.). The reaction mixture was stirred for 2 days at room temperature. The reaction mixture was then adjusted to pH=6 with HCl (1M in water) and concentrated in vacuum. The crude was purified on HPLC to give compound P68 (110 mg, 53%).

m/z=529 (M+H)$^+$ $^1$H NMR (400 MHz, DMSO-d$_6$) δ ppm 1.44-1.62 (m, 1H) 1.64-1.76 (m, 2H) 1.78-1.91 (m, 1H) 2.16-2.37 (m, 4H) 3.24 (s, 3H) 3.46-3.59 (m, 5H) 3.68-3.77 (m, 5H) 4.02 (t, J=7.37 Hz, 4H) 5.22 (s, 1H) 5.54-5.88 (m, 2H) 7.39-7.44 (m, 1H) 7.68-7.73 (m, 2H)

Synthesis of 4-(2-(5-(azetidin-1-yl)-7-morpholinopyrazolo[1,5-a]pyrimidin-2-yl)-piperidin-1-yl)-5-methyl-N-(methylsulfonyl)quinazoline-2-carboxamide P69

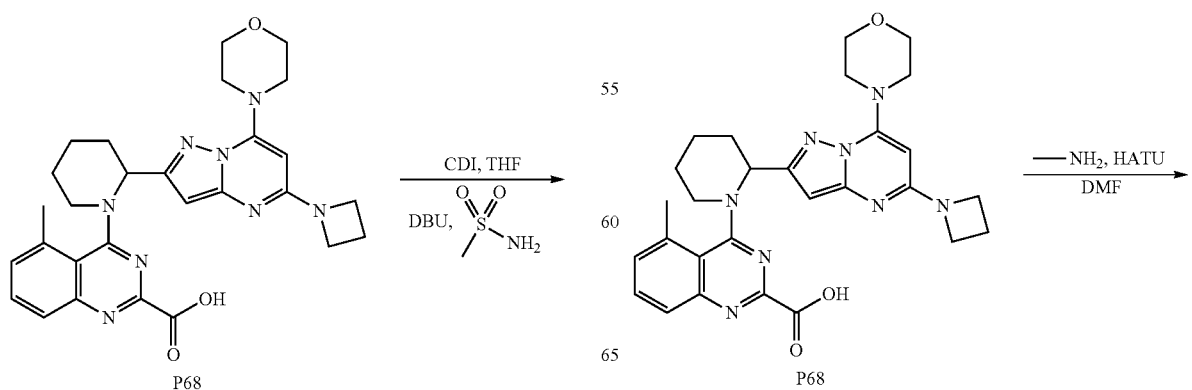

Compound P68 (150 mg, 0.28 mmol) was dissolved in 10 mL THF and CDI (92 mg, 0.56 mmol, 2 eq.) was added. The mixture was heated to 50° C. and after one hour stirring, DBU (0.08 mL, 0.56 mmol, 2 eq.) and methyl sulfonamide (70 mg, 0.74 mmol, 2.6 eq.) were added to the solution. After 1 hour stirring at 50° C. the solution was concentrated in vacuum and purified by column chromatography eluting with a gradient starting from 0% to 10% MeOH in DCM giving compound P69 (65 mg, 38%).

m/z=606 (M+H)$^+$ $^1$H NMR (400 MHz, DMSO-d$_6$) δ ppm 1.46-1.60 (m, 1H) 1.62-1.73 (m, 2H) 1.77-1.89 (m, 1H) 2.15-2.38 (m, 4H) 2.80 (s, 3H) 3.27 (s, 3H) 3.42-3.60 (m, 5H) 3.64-3.77 (m, 5H) 4.00 (t, J=7.42 Hz, 4H) 5.20 (s, 1H) 5.68-5.77 (m, 2H) 7.38-7.47 (m, 1H) 7.65-7.76 (m, 2H)

Synthesis of 4-(2-(5-(azetidin-1-yl)-7-morpholinopyrazolo[1,5-a]pyrimidin-2-yl)-piperidin-1-yl)-N,5-dimethylquinazoline-2-carboxamide P70

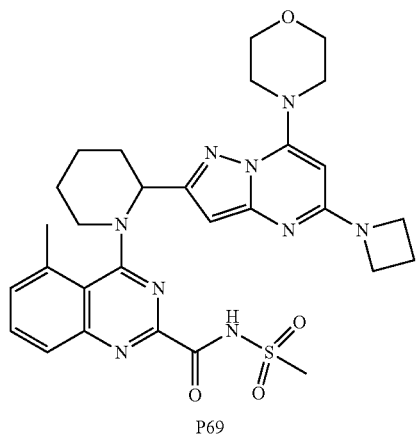

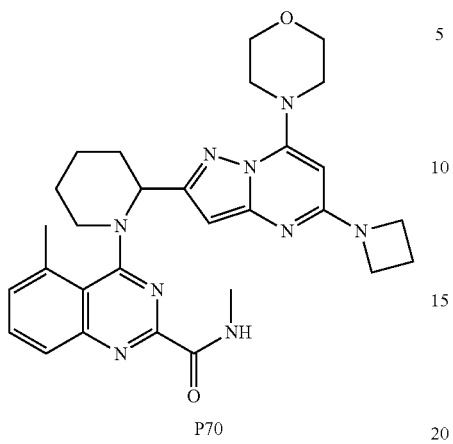

P70

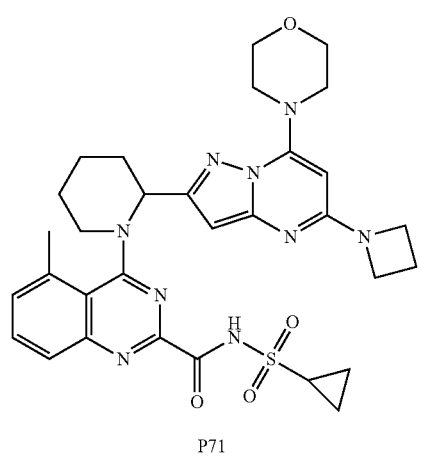

P71

To a solution of compound P68 (240 mg, 0.45 mmol) in DMF (5 mL) was added DIPEA (0.23 mL, 1.36 mmol, 3 eq.), methyl amine (0.08 mL, 0.90 mmol, 2 eq.) and HATU (431.5 mg, 1.135 mmol, 2.5 eq.). The resulting solution was stirred for 1 hour at room temperature. Water (5 mL) was added and the solution was concentrated in vacuum and purified on HPLC to give compound P70 (87 mg, 36%).

m/z=542 (M+H)$^+$ $^1$H NMR (400 MHz, DMSO-d$_6$) δ ppm 1.45-1.60 (m, 1H) 1.67 (br. s., 2H) 1.76-1.90 (m, 1H) 2.10-2.24 (m, 2H) 2.28 (quin, J=7.37 Hz, 2H) 2.79-2.87 (m, 6H) 3.35-3.62 (m, 6H) 3.61-3.75 (m, 4H) 3.98 (t, J=7.37 Hz, 4H) 5.19 (s, 1H) 5.54 (br. s., 1H) 5.68 (br. s., 1H) 7.29-7.42 (m, 1H) 7.58-7.72 (m, 2H) 8.04 (br. s., 1H)

Synthesis of 4-(2-(5-(azetidin-1-yl)-7-morpholin-opyrazolo[1,5-a]pyrimidin-2-yl)-piperidin-1-yl)-N-(cyclopropylsulfonyl)-5-methylquinazoline-2-carboxamide P71

Compound P68 (150 mg, 0.28 mmol) was dissolved in 10 mL THF and CDI (92 mg, 0.56 mmol, 2 eq.) was added. The mixture was heated to 50° C. and after one hour stirring, DBU (0.12 mL, 0.85 mmol, 3 eq.) and cyclopropyl sulfonamide (85 mg, 0.709 mmol, 2.5 eq.) were added to the solution. After 1 hour stirring at 50° C. the solution was concentrated in vacuum and purified by column chromatography eluting with a gradient starting from 0% to 10% MeOH in DCM and further purified on HPLC giving compound P71 (65 mg, 44%).

m/z=632 (M+H)$^+$ $^1$H NMR (400 MHz, DMSO-d$_6$) δ ppm 0.99-1.10 (m, 2H) 1.13-1.26 (m, 2H) 1.44-1.93 (m, 4H) 2.12-2.35 (m, 4H) 2.81 (s, 3H) 2.95-3.02 (m, 1H) 3.41-3.60 (m, 5H) 3.63-3.75 (m, 5H) 3.99 (t, J=7.42 Hz, 4H) 5.19 (s, 1H) 5.65-5.77 (m, 2H) 7.42 (d, J=6.67 Hz, 1H) 7.67-7.75 (m, 2H)

Synthesis of 4-(5-(azetidin-1-yl)-2-(1-(2-(isoxazol-4-yl)-5-methylquinazolin-4-yl)-piperidin-2-yl)pyrazolo[1,5-a]pyrimidin-7-yl)morpholine P72

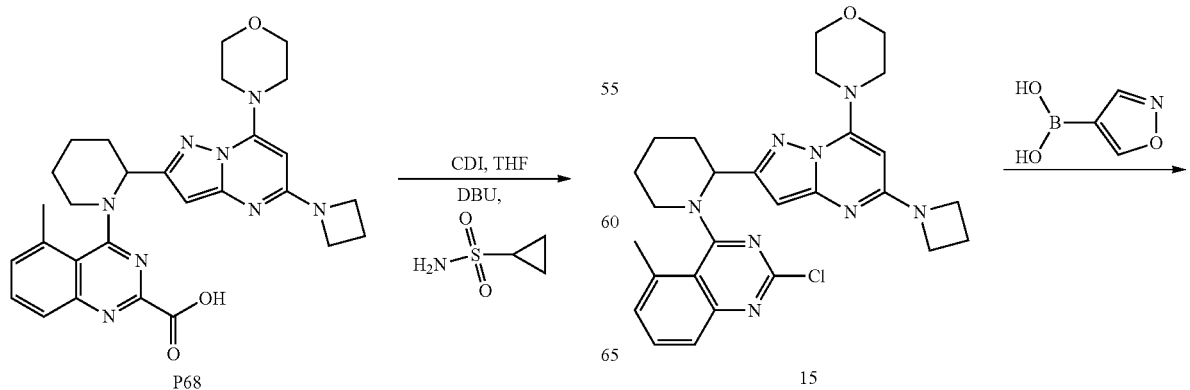

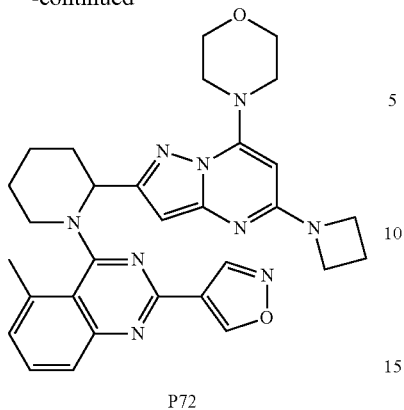

P72

Intermediate 15 (200 mg, 0.369 mmol), isoxazol-4-ylboronic acid (cas=1008139-25-0, 83 mg, 0.738 mmol) and K₂CO₃ (cas=584-08-7, 102 mg, 0.738 mmol) were dissolved in 1,4-dioxane (3 ml) and water (0.3 ml). The solution was degazed by N₂ for 5 minutes. The reaction tube was sealed and the mixture was heated at 120° C. for 30 minutes in a microwave oven. Then the solution was diluted with DCM and water. The product was extracted 2 times with DMC. The organic layers were dried over Na₂SO₄, filtered and evaporated to dryness and the crude was purified by column chromatography eluting with a gradient of MeOH in DCM, starting with 0% to 5% MeOH. After evaporation of the concerning fractions we get a brown solid. The solid was triturated in hot DIPE. After cooling to room temperature, the precipitate was filtered. Because the product was still not pure, the brown solid was triturated once again with hot DIPE. After cooling the title compound P72 was obtained by filtration (21 mg, 10%).

m/z=552.3 (M+H).

¹H NMR (400 MHz, DMSO-d₆) δ ppm 1.25-2.46 (m, 8H) 2.66 (s, 3H) 3.24-4.72 (m, 14H) 5.09-9.25 (m, 8H)

Synthesis of 4-(5-(azetidin-1-yl)-2-(1-(2-(1,4-dimethyl-1H-1,2,3-triazol-5-yl)-5-methylquinazolin-4-yl)piperidin-2-yl)pyrazolo[1,5-a]pyrimidin-7-yl)morpholine P73

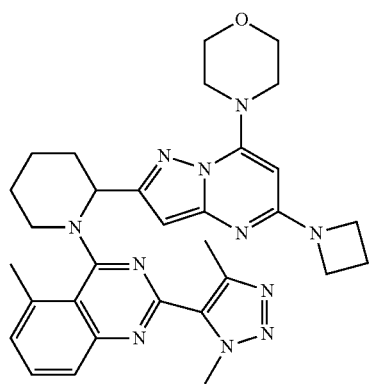

P73

Compound P73 was prepared in the same manner as compound P72 using intermediate 15 and 1,4-dimethyl-5-(4,4,5,5-tetramethyl-1,3,2-dioxaborolan-2-yl)-1H-1,2,3-triazole as starting material.

m/z=580 (M+H).

MP: 238.91° C.

¹H NMR (400 MHz, CDCl₃) δ ppm 1.29-2.05 (m, 4H) 2.12-2.49 (m, 4H) 2.55-2.76 (m, 3H) 2.82-3.00 (m, 3H) 3.13-4.16 (m, 14H) 4.30-4.49 (m, 3H) 4.93-6.11 (m, 3H) 7.27-7.34 (m, 1H) 7.53-7.79 (m, 2H)

Synthesis of 4-(5-(azetidin-1-yl)-2-(1-(5-methoxyquinazolin-4-yl)piperidin-2-yl)-pyrazolo[1,5-a]pyrimidin-7-yl)morpholine P74

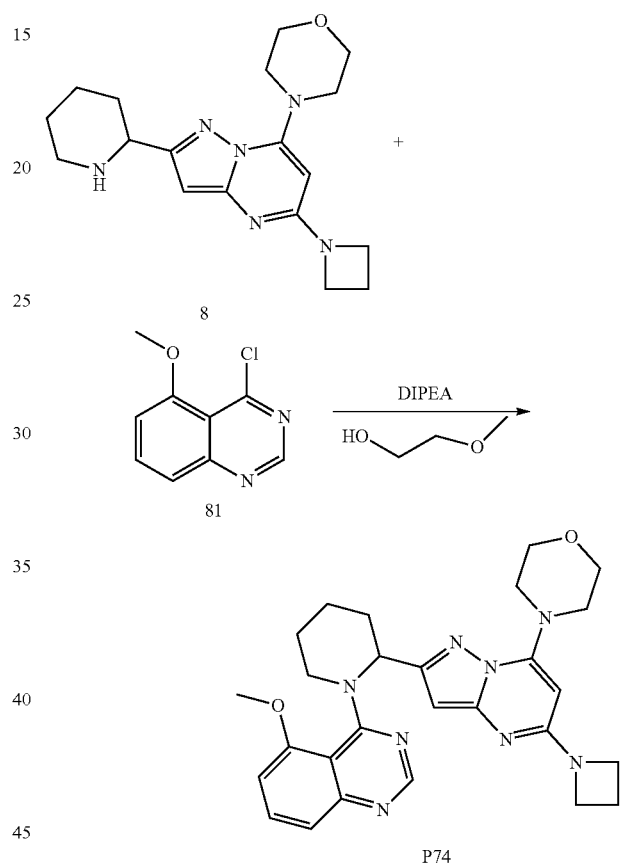

P74

The mixture of intermediate 8 TFA salt (300 mg, 0.65 mmol), 4-chloro-5-methoxy-quinazoline 81 (153 mg, 0.78 mmol) was dissolved in 2-methoxyethanol (15 mL) then diisopropylethyl amine (0.45 mL, 2.6 mmol) was added. The resulting mixture was stirred at 50° C. overnight. The mixture was allowed to cool down to room temperature and poured in iced watered solution. The resulting mixture was stirred until all the ice is melt then the resulting solid was filtered off. The solid was successively washed with water, dissolved in dichloromethane, dried over MgSO4 and concentrated to yield compound P74 (267 mg, 81%) as a white light solid.

m/z=501 (M+H).

¹H NMR (400 MHz, DMSO-d₆) δ ppm 1.58-1.82 (m, 4H), 2.02-2.14 (m, 1H), 2.22-2.39 (m, 3H), 3.28-3.41 (m, 1H), 3.45-3.56 (m, 4H), 3.66-3.75 (m, 4H), 3.92 (s, 3H), 3.99 (t, J=7.5 Hz, 5H), 5.18 (s, 1H), 5.63 (s, 1H), 5.68 (br. s., 1H), 6.95 (d, J=7.5 Hz, 1H), 7.28 (d, J=8.4 Hz, 1H), 7.59 (t, J=8.1 Hz, 1H), 8.35 (s, 1H).

B. Pharmacological Examples

B.1 Antiviral Activity

Black 384-well clear-bottom microtiter plates (Corning, Amsterdam, The Netherlands) were filled via acoustic drop ejection using the echo liquid handler (Labcyte, Sunnyvale, Calif.). 200 nL of compound stock solutions (100% DMSO) were transferred to the assay plates. 9 serial 4-fold dilutions of compound were made, creating per quadrant the same compound concentration. The assay was initiated by adding 10 µL of culture medium to each well (RPMI medium without phenol red, 10% FBS-heat inactivated, 0.04% gentamycin (50 mg/mL). All addition steps are done by using a multidrop dispenser (Thermo Scientific, Erembodegem, Belgium). Next, rgRSV224 virus (MOI=1) diluted in culture medium was added to the plates. rgRSV224 virus is an engineered virus that includes an additional GFP gene (Hallak L K, Spillmann D, Collins P L, Peeples M E. Glycosaminoglycan sulfation requirements for respiratory syncytial virus infection; Journal of virology (2000), 74(22), 10508-13) and was in-licensed from the NIH (Bethesda, Md., USA). Finally, 20 µL of a HeLa cell suspension (3,000 cells/well) were plated. Medium, virus- and mock-infected controls were included in each test. The wells contain 0.05% DMSO per volume. Cells were incubated at 37° C. in a 5% CO2 atmosphere. Three days post-virus exposure, viral replication was quantified by measuring GFP expression in the cells by an in house developed MSM laser microscope (Tibotec, Beerse, Belgium). The EC50 was defined as the 50% inhibitory concentration for GFP expression. In parallel, compounds were incubated for three days in a set of white 384-well microtiter plates (Corning) and the cytotoxicity of compounds in HeLa cells was determined by measuring the ATP content of the cells using the ATPlite kit (Perkin Elmer, Zaventem, Belgium) according to the manufacturer's instructions. The $CC_{50}$ was defined as the 50% concentration for cytotoxicity.

TABLE B-1 antiviral data and selectivity index

| Co. No. | RSV HELA $pEC_{50}$ | SI TOX HELA |
|---|---|---|
| P1 | 6.1 | 4.4 |
| P2 | 6.5 | 4.4 |
| P3 | 5.4 | 4.6 |
| P4 | 6.8 | <4 |
| P5 | 6.6 | <5 |
| P6 | 8.3 | <4.0 |
| P7 | 5.7 | <4 |
| P8 | 8.1 | <4 |
| P9 | 8.3 | <4.6 |
| P10 | 6.2 | <4.3 |
| P11 | 6.9 | <4.6 |
| P12 | 6.7 | <4 |
| P13 | 6.4 | 4.3 |
| P14 | 6.1 | <4 |
| P15 | 6.6 | 4.0 |
| P16 | 7.1 | 4.3 |
| P17 | 8.4 | 4.4 |
| P18 | <6 | <4.3 |
| P19 | 8.0 | <4.3 |
| P20 | 6.2 | 5.4 |
| P21 | 6.4 | <4.6 |
| P22 | 7.1 | 4.5 |
| P23 | 7.8 | <4.6 |
| P24 | <4.6 | <4.6 |
| P25 | 7.5 | <4.6 |
| P26 | 7.6 | 4.3 |
| P27 | 6.2 | 4.5 |
| P28 | 6.1 | <4 |
| P29 | 6.4 | 4.5 |
| P30 | 6.2 | 4.6 |
| P31 | 6.8 | 4.8 |
| P32 | 7.3 | <4 |
| P33 | 7.88 | 4.2 |
| P34 | 6.2 | 4.3 |
| P35 | 7.2 | 4.4 |
| P36 | 6.3 | <4 |
| P37 | 6.5 | 4.3 |
| P40 | 6.8 | 4.7 |
| P41 | 7.1 | <4 |
| P42 | 5.6 | <4.6 |
| P43 | 4.8 | 4.2 |
| P44 | 6.1 | 4.2 |
| P45 | 6.7 | 4.2 |
| P46 | 6.5 | 4.3 |
| P47 | 6.3 | 4.6 |
| P48 | 7.9 | 4.5 |
| P49 | 6.1 | 4.3 |
| P50 | 6.2 | 4.3 |
| P51 | 6.5 | 4.3 |
| P52 | 7.1 | 4.7 |
| P53 | 7.3 | 4.6 |
| P54 | 7.6 | 4.5 |
| P55 | 7.8 | 4.3 |
| P57 | 6.2 | 4.5 |
| P58 | 6.3 | <4 |
| P59 | 6.4 | 4.3 |
| P60 | 6.9 | 4.3 |
| P61 | 7.5 | <4 |
| P62 | 7.0 | 4.3 |
| P63 | 6.4 | 4.4 |
| P64 | 7.8 | <4.6 |
| P65 | 7.8 | <4.6 |
| P66 | 7.0 | — |
| P67 | 6.9 | <4.3 |
| P68 | 6.5 | <4.6 |
| P69 | 6.5 | <4 |
| P70 | 6.2 | 4.3 |
| P71 | 6.4 | <4 |
| P72 | 7.6 | 4.5 |
| P73 | 6.9 | 4.8 |
| P74 | 7.8 | <4.6 |

C. Prophetic Composition Examples

"Active ingredient" as used throughout these examples relates to a final compound of Formula (I), the pharmaceutically acceptable salts thereof, the solvates and the stereochemically isomeric forms and the tautomers thereof.

Typical examples of recipes for the formulation of the invention are as follows:

C.1. Tablets

| | |
|---|---|
| Active ingredient | 5 to 50 mg |
| Di calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

C.2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

C.3. Injectable

A parenteral composition is prepared by stirring 1.5% by weight of active ingredient of the invention in 10% by volume propylene glycol in water.

C.4. Ointment

| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound of formula (I), wherein

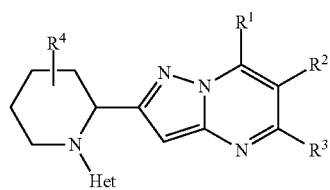

(I)

$R^1$ is selected from the group consisting of: hydrogen, hydroxy, $C_{1-4}$alkyl, mono- or di($C_{1-4}$ alkyl)amino, and Heterocyclyl$^1$;

$R^2$ is hydrogen or $C_{1-4}$alkyl;

$R^3$ is selected from the group consisting of: $C_{1-4}$alkyl, halo, $C_{3-6}$cycloalkyl, mono- or di($C_{1-4}$alkyl)amino, and Heterocyclyl$^2$;

$R^4$ is selected from the group consisting of: hydrogen, $C_{1-6}$alkyl, hydroxy, and halo;

Heterocyclyl$^1$ is selected from the group consisting of: azetidinyl, pyrrolidinyl, piperidinyl, piperazinyl, and morpholinyl; wherein each azetidinyl, pyrrolidinyl, piperidinyl, piperazinyl, and morpholinyl is optionally substituted with one or two substituents each independently selected from the group consisting of: $C_{1-4}$alkyl, hydroxy, halo, polyhalo$C_{1-4}$alkyl, $C_{1-4}$alkyloxycarbonyl, amino, $C_{1-4}$alkylaminocarbonyl, and $C_{1-4}$alkylsulfonyl;

Heterocyclyl$^2$ is selected from the group consisting of: azetidinyl, pyrrolidinyl, piperidinyl, piperazinyl, and morpholinyl; wherein each azetidinyl, pyrrolidinyl, piperidinyl, piperazinyl, and morpholinyl is optionally substituted with one or two substituents each independently selected from the group consisting of: $C_{1-4}$alkyl, hydroxy, halo, polyhalo$C_{1-4}$alkyl, $C_{1-4}$alkyloxycarbonyl, amino, $C_{1-4}$alkyloxycarbonylamino, and $C_{1-4}$alkylsulfonyl; and Het is selected from the group consisting of: furanyl, thiophenyl, pyrazolyl, oxazolyl, thiazolyl, pyridyl, pyridazinyl, pyrimidinyl, pyrazinyl, quinolyl, isoquinolyl, cinnolinyl, quinazolinyl, quinoxalinyl, 1,5-naphthyridinyl, 1,6-naphthyridinyl, 1,7-naphthyridinyl, 1,8-naphthyridinyl, pyrido[2,3-d]pyrimidinyl, pyrido[3,2-d]pyrimidinyl, 9H-purinyl, thiazolo[5,4-d]pyrimidinyl, 7H-pyrrolo[2,3-d]pyrimidinyl, oxazolo[5,4-d]pyrimidinyl, thieno[2,3-d]-pyrimidinyl, and thieno[3,2-d]pyrimidinyl; wherein each furanyl, thiophenyl, pyrazolyl, pyridyl, pyridazinyl, pyrimidinyl, pyrazinyl, quinolyl, isoquinolyl, cinnolinyl, quinazolinyl, quinoxalinyl, 1,5-naphthyridinyl, 1,6-naphthyridinyl, 1,7-naphthyridinyl, 1,8-naphthyridinyl, pyrido[2,3-d]pyrimidinyl, pyrido[3,2-d]pyrimidinyl, 9H-purinyl, thiazolo[5,4-d]pyrimidinyl, 7H-pyrrolo[2,3-d]pyrimidinyl, oxazolo[5,4-d]pyrimidinyl, thieno[2,3-d]-pyrimidinyl, and thieno[3,2-d]pyrimidinyl is optionally substituted with one, two or three substituents each independently selected from the group consisting of: halo, $C_{1-4}$alkyl, $C_{1-4}$alkyloxy, $C_{1-4}$alkylthio, hydroxy, amino, mono- or di($C_{1-4}$ alkyl)amino, hydroxycarbonyl, $C_{1-4}$alkyloxycarbonyl, $C_{1-4}$alkylsulfonylamino, aminocarbonyl, trifluoromethyl, $C_{1-4}$alkyloxycarbonylamino, di($C_{1-4}$alkyloxycarbonyl)amino, $C_{1-4}$alkylsulfonylaminocarbonyl, $C_{1-4}$alkylaminocarbonyl, $C_{1-4}$alkyloxyC$_{1-6}$alkyloxycarbonylamino, di($C_{1-4}$alkyl)aminosulfonyl-aminocarbonyl, $C_{3-6}$cycloalkylsulfonylaminocarbonyl, and HO—NH—(C=NH)—; and oxazolyl or triazolyl; wherein each oxazolyl or triazolyl is optionally substituted with one or two $C_{1-4}$alkyl;

and pharmaceutically acceptable salts thereof.

2. The compound as claimed in claim 1 wherein $R^1$ is hydrogen, $C_{1-4}$alkyl, mono- or di($C_{1-4}$alkyl)amino, or Heterocyclyl$^1$;

$R^2$ is hydrogen or $C_{1-4}$alkyl;

$R^3$ is $C_{3-6}$cycloalkyl or Heterocyclyl$^2$;

$R^4$ is hydrogen;

Heterocyclyl$^1$ is piperazinyl or morpholinyl; wherein each piperazinyl or morpholinyl is optionally substituted with one substituent selected from $C_{1-4}$alkyloxycarbonyl, $C_{1-4}$alkylaminocarbonyl, or $C_{1-4}$alkylsulfonyl;

Heterocyclyl$^2$ is azetidinyl, or pyrrolidinyl; wherein each azetidinyl, or pyrrolidinyl is optionally substituted with one substituent selected from hydroxy or amino; and Het is selected from quinazolinyl, pyrido[2,3-d]pyrimidinyl, thiazolo[5,4-d]-pyrimidinyl, 7H-pyrrolo[2,3-d]pyrimidinyl, oxazolo[5,4-d]pyrimidinyl, or thieno[2,3-d]pyrimidinyl; wherein each quinazolinyl, pyrido[2,3-d]pyrimidinyl, thiazolo[5,4-d]-pyrimidinyl, 7H-pyrrolo[2,3-d]pyrimidinyl, oxazolo[5,4-d]pyrimidinyl, or thieno[2,3-d]pyrimidinyl is optionally substituted with one, two or three substituents each independently selected from halo, $C_{1-4}$alkyl, $C_{1-4}$alkyloxy, $C_{1-4}$alkylthio, hydroxy, hydroxycarbonyl, $C_{1-4}$alkyloxycarbonyl, $C_{1-4}$alkylsulfonylamino, aminocarbonyl, trifluoromethyl, $C_{1-4}$alkyloxy-carbonylamino, di($C_{1-4}$alkyloxycarbonyl)amino, $C_{1-4}$alkylsulfonylaminocarbonyl, $C_{1-4}$alkylaminocarbonyl, $C_{1-4}$alkyloxyC$_{1-6}$alkyloxycarbonylamino, di($C_{1-4}$alkyl)aminosulfonylaminocarbonyl, $C_{3-6}$cycloalkylsulfonylamino-carbonyl, and HO—NH—(C=NH)—; and oxazolyl or triazolyl; wherein each oxazolyl or triazolyl is optionally substituted with one or two $C_{1-4}$alkyl.

3. The compound as claimed in claim 1 wherein $R^1$ is Heterocyclyl$^1$, $R^2$ is hydrogen, and $R^3$ is Heterocyclyl$^2$.

4. The compound as claimed in claim 1 wherein $R^1$ is hydrogen, $R^2$ is $C_{1-4}$alkyl, and $R^3$ is Heterocyclyl$^2$.

5. The compound as claimed in claim 1 wherein $R^1$ is hydrogen, $R^2$ is hydrogen, and $R^3$ is Heterocyclyl².

6. The compound as claimed in claim 1 wherein $R^1$ is $C_{1-4}$alkyl, $R^2$ is hydrogen, and $R^3$ is Heterocyclyl².

7. The compound as claimed in claim 1 wherein $R^1$ is hydrogen, $R^2$ is hydrogen, and $R^3$ is $C_{1-4}$alkyl.

8. The compound as claimed in claim 1 wherein $R^1$ is hydrogen, $R^2$ is hydrogen, and $R^3$ is $C_{3-6}$cycloalkyl.

9. The compound as claimed in claim 1 wherein Het is quinazolinyl.

10. A compound selected from the group consisting of:
- 4-(5-(Azetidin-1-yl)-2-(1-(6-chloroquinazolin-4-yl)piperidin-2-yl)-pyrazolo[1,5-a]pyrimidin-7-yl)morpholine;
- (S)-4-(5-(Azetidin-1-yl)-2-(1-(6-chloroquinazolin-4-yl)piperidin-2-yl)-pyrazolo[1,5-a]pyrimidin-7-yl)morpholine;
- (R)-4-(5-(Azetidin-1-yl)-2-(1-(6-chloroquinazolin-4-yl)piperidin-2-yl)pyrazolo[1,5-a]pyrimidin-7-yl)morpholine;
- 4-(5-(Azetidin-1-yl)-2-(1-(6-methylquinazolin-4-yl)piperidin-2-yl)-pyrazolo[1,5-a]pyrimidin-7-yl)morpholine;
- 4-(5-(Azetidin-1-yl)-2-(1-(2-chloro-6-methylquinazolin-4-yl)piperidin-2-yl)pyrazolo[1,5-a]pyrimidin-7-yl)morpholine;
- N-(4-(2-(5-(Azetidin-1-yl)-7-morpholinopyrazolo[1,5-a]pyrimidin-2 yl)-piperidin-1-yl)-6-methylquinazolin-2-yl)methanesulfonamide;
- (R)—N-(4-(2-(5-(Azetidin-1-yl)-7-morpholinopyrazolo[1,5-a]pyrimidin-2-yl)-piperidin-1-yl)-6-methylquinazolin-2-yl)methanesulfonamide;
- (S)—N-(4-(2-(5-(Azetidin-1-yl)-7-morpholinopyrazolo[1,5-a]pyrimidin-2-yl)piperidin-1-yl)-6-methylquinazolin-2-yl)methanesulfonamide;
- N-(4-(2-(5-(Azetidin-1-yl)-7-morpholinopyrazolo[1,5-a]pyrimidin-2 yl)piperidin-1-yl)-5-methylquinazolin-2-yl)methanesulfonamide;
- N-(4-(2-(5-(Azetidin-1-yl)-7-morpholinopyrazolo[1,5-a]pyrimidin-2 yl)piperidin-1-yl)quinazolin-2-yl)methanesulfonamide;
- 4-(2-(5-(Azetidin-1-yl)-6-methylpyrazolo[1,5-a]pyrimidin-2-yl)-piperidin-1-yl)-6-methylquinazoline;
- 1-(6-Methyl-2-(1-(6-methylquinazolin-4-yl)piperidin-2-yl)pyrazolo-[1,5-a]pyrimidin-5-yl)azetidin-3-ol;
- 1-(6-Methyl-2-(1-(6-methylquinazolin-4-yl)piperidin-2-yl)pyrazolo-[1,5-a]pyrimidin-5-yl)azetidin-3-amine;
- 2-Methoxyethyl 4-(2-(5-(azetidin-1-yl)-7-morpholinopyrazolo[1,5-a]-pyrimidin-2-yl)piperidin-1-yl)-6-morpholinoquinazolin-2-ylcarbamate;
- 4-(5-(Azetidin-1-yl)-2-(1-(2-methyl-7H-pyrrolo[2,3-d]pyrimidin-4-yl)-piperidin-2-yl)pyrazolo[1,5-a]pyrimidin-7-yl)morpholine;
- 4-(5-(Azetidin-1-yl)-2-(1-(2-ethoxypyrido[2,3-d]pyrimidin-4-yl)-piperidin-2-yl)pyrazolo[1,5-a]pyrimidin-7-yl)morpholine;
- 4-(5-(Azetidin-1-yl)-2-(1-(5-methylquinazolin-4-yl)piperidin-2-yl)-pyrazolo[1,5-a]pyrimidin-7-yl)morpholine;
- (R)-4-(5-(Azetidin-1-yl)-2-(1-(5-methylquinazolin-4-yl)piperidin-2-yl)-pyrazolo[1,5-a]pyrimidin-7-yl)morpholine;
- (S)-4-(5-(Azetidin-1-yl)-2-(1-(5 methylquinazolin-4-yl)piperidin-2-yl)-pyrazolo[1,5-a]pyrimidin-7-yl)morpholine;
- 4-(5-(Azetidin-1-yl)-2-(1-(2-methylthiazolo[5,4-d]pyrimidin-7-yl)-piperidin-2-yl)pyrazolo[1,5-a]pyrimidin-7-yl)morpholine;
- 4-(2-(5-(Azetidin-1-yl)-7-methylpyrazolo[1,5-a]pyrimidin-2-yl)-piperidin-1-yl)-6-methylquinazoline;
- 4-(2-(5-(Azetidin-1-yl)-6-methyl-7-(piperidin-1-yl)pyrazolo[1,5-a]-pyrimidin-2-yl)piperidin-1-yl)-6-methylquinazoline;
- 1-(6-Methyl-2-(1-(5-methylquinazolin-4-yl)piperidin-2-yl)pyrazolo-[1,5-a]pyrimidin-5-yl)azetidin-3-ol;
- (R)-1-(6-Methyl-2-(1-(5-methylquinazolin-4-yl)piperidin-2-yl)pyrazolo[1,5-a]-pyrimidin-5-yl)azetidin-3-ol;
- (S)-1-(6-Methyl-2-(1-(5-methylquinazolin-4-yl)-piperidin-2-yl)pyrazolo[1,5-a]-pyrimidin-5-yl)azetidin-3-ol;
- 1-(6-Methyl-2-(1-(5-methylquinazolin-4-yl)piperidin-2-yl)pyrazolo-[1,5-a]pyrimidin-5-yl)azetidin-3-amine;
- 1-(2-(1-(2,5-Dimethylquinazolin-4-yl)piperidin-2-yl)-6-methyl-pyrazolo[1,5-a]pyrimidin-5-yl)azetidin-3-amine;
- Dimethyl (4-{2-[5-(azetidin-1-yl)-7-(morpholin-4-yl)pyrazolo[1,5-a]-pyrimidin-2-yl]piperidin-1-yl}-5-methylquinazolin-2-yl)imidodicarbonate;
- Methyl (4-(2-(5-(azetidin-1-yl)-7-morpholinopyrazolo[1,5-a]-pyrimidin-2-yl)piperidin-1-yl)-5-methylquinazolin-2-yl)carbamate;
- 4-(2-(5-(Azetidin-1-yl)-7-morpholinopyrazolo[1,5-a]pyrimidin-2-yl)-piperidin-1-yl)-N-hydroxy-5-methylquinazoline-2-carboximidamide;
- 4-(5-(Azetidin-1-yl)-2-(1-(2-ethoxy-5-methylquinazolin-4-yl)piperidin-2-yl)pyrazolo[1,5-a]pyrimidin-7-yl)morpholine;
- (S)—N-(4-(2-(5-(Azetidin-1-yl)-7-morpholinopyrazolo[1,5-a]-pyrimidin-2-yl)piperidin-1-yl)-6-chloroquinazolin-2-yl)methanesulfonamide;
- (S)—N-(4-(2-(5-(Azetidin-1-yl)-7-morpholinopyrazolo[1,5-a]-pyrimidin-2-yl)piperidin-1-yl)-6-chloroquinazolin-2-yl)methanesulfonamide;
- (R)—N-(4-(2-(5-(Azetidin-1-yl)-7-morpholinopyrazolo[1,5-a]-pyrimidin-2-yl)piperidin-1-yl)-6-chloroquinazolin-2-yl)methanesulfonamide;
- 4-(5-(Azetidin-1-yl)-2-(1-(5-chloroquinazolin-4-yl)piperidin-2-yl)-pyrazolo[1,5-a]pyrimidin-7-yl)morpholine;
- 4-(2-(5-(Azetidin-1-yl)-7-morpholinopyrazolo[1,5-a]pyrimidin-2-yl)-piperidin-1-yl)-N—(N,N-dimethyl sulfamoyl)quinazoline-2-carboxamide;
- 1-(2-(1-(2,5-Dimethylquinazolin-4-yl)piperidin-2-yl)-6-methyl-pyrazolo[1,5-a]pyrimidin-5-yl)azetidin-3-ol;
- (S)-1-(2-(1-(2,5-Dimethylquinazolin-4-yl)piperidin-2-yl)-6-methyl-pyrazolo[1,5-a]pyrimidin-5-yl)azetidin-3-ol;
- (R)-1-(2-(1-(2, 5-Dimethylquinazolin-4-yl)piperidin-2-yl)-6-methyl-pyrazolo[1,5-a]pyrimidin-5-yl)azetidin-3-ol;
- 1-(2-(1-(2-Chloro-5-methylquinazolin-4-yl)piperidin-2-yl)-6-methylpyrazolo[1,5-a]pyrimidin-5-yl)azetidin-3-ol;
- N-(4-(2-(5-(3-Hydroxyazetidin-1-yl)-6-methylpyrazolo[1,5-a]-pyrimidin-2-yl)piperidin-1-yl)-5-methylquinazolin-2-yl)methanesulfonamide;
- 1-(2-(1-(2,6-Dimethylquinazolin-4-yl)piperidin-2-yl)-6-methyl-pyrazolo[1,5-a]pyrimidin-5-yl)azetidin-3-ol;
- (S)-1-(2-(1-(2,6-Dimethylquinazolin-4-yl)piperidin-2-yl)-6-methyl-pyrazolo[1,5-a]pyrimidin-5-yl)azetidin-3-ol;

(R)-1-(2-(1-(2,6-Dimethyl-quinazolin-4-yl)piperidin-2-yl)-6-methylpyrazolo[1,5-a]pyrimidin-5-yl)azetidin-3-ol;

4-(2-(5-(Azetidin-1-yl)-7-morpholinopyrazolo[1,5-a]pyrimidin-2-yl)-piperidin-1-yl)-5-methylquinazolin-2-ol;

4-(2-(5-(Azetidin-1-yl)-7-morpholinopyrazolo[1,5-a]pyrimidin-2-yl)-piperidin-1-yl)-5-methylquinazoline-2-carboxamide;

4-(5-Cyclopropyl-6-methyl-2-(1-(5-methylquinazolin-4-yl)piperidin-2 yl)-pyrazolo[1,5-a]pyrimidin-7-yl)morpholine;

(3 S)-1-(6-Methyl-2-(1-(5-methylquinazolin-4-yl)piperidin-2-yl)-pyrazolo[1,5-a]pyrimidin-5-yl)pyrrolidin-3-amine;

(3 S)-1-(2-(1-(6-Methylquinazolin-4-yl)piperidin-2-yl) pyrazolo[1,5-a]pyrimidin-5-yl)pyrrolidin-3-amine;

(S)-1-(2-((R)-1-(6-Methylquinazolin-4-yl)piperidin-2-yl) pyrazolo-[1,5 a]-pyrimidin-5-yl)pyrrolidin-3-amine;

(S)-1-(2-((S)-1-(6-Methylquinazolin-4-yl)piperidin-2-yl) pyrazolo-[1,5 a]-pyrimidin-5-yl)pyrrolidin-3-amine;

tert-Butyl 4-(5-(azetidin-1-yl)-2-(1-(5-methylquinazolin-4-yl)piperidin-2-yl)pyrazolo[1,5-a]pyrimidin-7-yl)piperazine-1-carboxylate;

4-(2-(5-(Azetidin-1-yl)-7-(piperazin-1-yl)pyrazolo[1,5-a]pyrimidin-2 yl)-piperidin-1-yl)-5-methylquinazoline;

4-(5-(Azetidin-1-yl)-2-(1-(5-methylquinazolin-4-yl)piperidin-2-yl)-pyrazolo[1,5-a]pyrimidin-7-yl)-N-isopropylpiperazine-1-carboxamide;

4-(2-(5-(Azetidin-1-yl)-7-(4-(methylsulfonyl)piperazin-1-yl)pyrazolo-[1,5-a]pyrimidin-2-yl)piperidin-1-yl)-5-methylquinazoline;

7-(2-(5-(Azetidin-1-yl)-7-morpholinopyrazolo[1,5-a]pyrimidin-2-yl)-piperidin-1-yl)-2-methyloxazolo[5,4-d]pyrimidine;

4-(5-(Azetidin-1-yl)-2-(1-(6-methyl-2-(methylthio)quinazolin-4-yl)-piperidin-2-yl)pyrazolo[1,5-a]pyrimidin-7-yl)morpholine;

4-(5-(Azetidin-1-yl)-2-(1-(5-ethylquinazolin-4-yl)piperidin-2-yl)-pyrazolo[1,5-a]pyrimidin-7-yl)morpholine;

4-(5-(Azetidin-1-yl)-2-(1-(5,7-dimethylquinazolin-4-yl) piperidin-2-yl)-pyrazolo[1,5-a]pyrimidin-7-yl)morpholine;

4-(5-(Azetidin-1-yl)-2-(1-(5-fluoroquinazolin-4-yl)piperidin-2-yl)-pyrazolo[1,5-a]pyrimidin-7-yl)morpholine;

4-(5-(Azetidin-1-yl)-2-(1-(5-ethoxyquinazolin-4-yl)piperidin-2-yl)-pyrazolo[1,5-a]pyrimidin-7-yl)morpholine;

4-(5-(Azetidin-1-yl)-2-(1-(5-(trifluoromethyl)quinazolin-4-yl)piperidin-2-yl)pyrazolo[1,5-a]pyrimidin-7-yl)morpholine;

4-(5-(Azetidin-1-yl)-2-(1-(6-ethyl-5-methylquinazolin-4-yl)piperidin-2 yl)-pyrazolo[1,5-a]pyrimidin-7-yl)morpholine;

4-(5-(Azetidin-1-yl)-2-(1-(5,6-dimethylquinazolin-4-yl) piperidin-2-yl)-pyrazolo[1,5-a]pyrimidin-7-yl)morpholine;

7-(2-(5-(Azetidin-1-yl)-7-morpholinopyrazolo[1,5-a]pyrimidin-2-yl)-piperidin-1-yl)-2-methyloxazolo[5,4-d]pyrimidine;

4-(5-(Azetidin-1-yl)-2-(1-(5,8-dimethylquinazolin-4-yl) piperidin-2-yl)-pyrazolo[1,5-a]pyrimidin-7-yl)morpholine;

Methyl 4-(2-(5-(azetidin-1-yl)-7-morpholinopyrazolo[1,5-a]pyrimidin-2-yl)piperidin-1-yl)-5-methylquinazoline-2-carboxylate;

4-(2-(5-(Azetidin-1-yl)-7-morpholinopyrazolo[1,5-a]pyrimidin-2-yl)-piperidin-1-yl)-5-methylquinazoline-2-carboxylic acid;

4-(2-(5-(Azetidin-1-yl)-7-morpholinopyrazolo[1,5-a]pyrimidin-2-yl)-piperidin-1-yl)-5-methyl-N-(methyl sulfonyl)quinazoline-2-carboxamide;

4-(2-(5-(Azetidin-1-yl)-7-morpholinopyrazolo[1,5-a]pyrimidin-2-yl)-piperidin-1-yl)-N,5-dimethylquinazoline-2-carboxamide;

4-(2-(5-(Azetidin-1-yl)-7-morpholinopyrazolo[1,5-a]pyrimidin-2-yl)-piperidin-1-yl)-N-(cyclopropyl sulfonyl)-5-methylquinazoline-2-carboxamide;

4-(5-(Azetidin-1-yl)-2-(1-(2-(isoxazol-4-yl)-5-methylquinazolin-4-yl)-piperidin-2-yl)pyrazolo[1,5-a]pyrimidin-7-yl)morpholine;

4-(5-(Azetidin-1-yl)-2-(1-(2-(1,4-dimethyl-1H-1,2,3-triazol-5-yl)-5-methyl-quinazolin-4-yl)piperidin-2-yl) pyrazolo[1,5-a]pyrimidin-7-yl)morpholine; and 4-(5-(Azetidin-1-yl)-2-(1-(5-methoxyquinazolin-4-yl)piperidin-2-yl)-pyrazolo[1,5-a]pyrimidin-7-yl)morpholine;

and pharmaceutically acceptable salts thereof.

11. A pharmaceutical composition comprising a pharmaceutically acceptable carrier and a therapeutically active amount of a compound as claimed in claim 1 or a pharmaceutically acceptable salt thereof.

12. A pharmaceutical composition, comprising (a) a therapeutically active amount of at least one compound of claim 10 or a pharmaceutically acceptable salt thereof; and (b) at least one pharmaceutically acceptable carrier.

13. A process for preparing a pharmaceutical composition comprising a pharmaceutically acceptable carrier and a therapeutically active amount of the compound of claim 1, wherein the therapeutically active amount of said compound or a pharmaceutically acceptable salt thereof is mixed with the pharmaceutically acceptable carrier.

14. A method of treating a respiratory syncytial virus infection in a patient, comprising administering the compound as claimed in claim 1 or a pharmaceutically acceptable salt thereof to said patient.

15. A method of treatment of a subject suffering from a respiratory syncytial virus infection, comprising administering to the subject a therapeutically active amount of a compound as claimed in claim 10 or a pharmaceutically acceptable salt thereof.

* * * * *